(12) United States Patent
Bin et al.

(10) Patent No.: US 8,940,409 B2
(45) Date of Patent: Jan. 27, 2015

(54) ORGANIC LIGHT EMITTING MATERIAL AND ORGANIC LIGHT EMITTING DEVICE USING THE SAME

(75) Inventors: Jong-Kwan Bin, Gyeonggi-Do (KR); Soon-Wook Cha, Gyeonggi-Do (KR); Seung-Jae Lee, Gyeonggi-Do (KR); In-Bum Song, Gyeonggi-Do (KR); Jung-Keun Kim, Seoul (KR); Do-Han Kim, Gyeonggi-Do (KR); Chun-Gun Park, Gyeonggi-Do (KR); Nam-Sung Cho, Gyeonggi-Do (KR)

(73) Assignee: LG Display Co., Ltd., Seoul (KR)

( * ) Notice: Subject to any disclaimer, the term of this patent is extended or adjusted under 35 U.S.C. 154(b) by 733 days.

(21) Appl. No.: 12/654,602

(22) Filed: Dec. 24, 2009

(65) Prior Publication Data

US 2010/0164374 A1 Jul. 1, 2010

(30) Foreign Application Priority Data

Dec. 30, 2008 (KR) ........................ 10-2008-0137517

(51) Int. Cl.
| | | |
|---|---|---|
| *C09K 11/06* | (2006.01) | |
| *H01L 51/54* | (2006.01) | |
| *C07C 255/51* | (2006.01) | |
| *C07C 15/62* | (2006.01) | |
| *C07C 43/205* | (2006.01) | |
| *C07C 43/225* | (2006.01) | |
| *C07C 255/54* | (2006.01) | |
| *C07F 7/08* | (2006.01) | |
| *C09B 23/14* | (2006.01) | |
| *C09B 57/00* | (2006.01) | |
| *C09B 57/10* | (2006.01) | |
| *H01L 51/00* | (2006.01) | |
| *H05B 33/14* | (2006.01) | |
| *H01L 51/50* | (2006.01) | |

(52) U.S. Cl.
CPC ............... *C07C 255/51* (2013.01); *C07C 15/62* (2013.01); *C07C 43/2055* (2013.01); *C07C 43/225* (2013.01); *C07C 255/54* (2013.01); *C07F 7/0809* (2013.01); *C07F 7/0818* (2013.01); *C09B 23/148* (2013.01); *C09B 57/001* (2013.01); *C09B 57/008* (2013.01); *C09B 57/10* (2013.01); *C09K 11/06* (2013.01); *H01L 51/0054* (2013.01); *H05B 33/14* (2013.01); *C07C 2103/50* (2013.01); *C09K 2211/1011* (2013.01); *H01L 51/5016* (2013.01); *Y10S 428/917* (2013.01)
USPC ........... 428/690; 428/917; 313/504; 313/506; 252/301.16; 257/40; 257/101; 257/102; 257/103; 257/E51.049

(58) Field of Classification Search
CPC ............ C07C 2101/16; C07C 2103/24; C07C 2103/26; C07C 2103/50; C07C 15/38; C07C 15/62; C07C 25/13; C07C 255/50; C07C 255/51; H01L 51/0054; H01L 51/5012; C09K 11/06; C09K 2211/1011
USPC ..................................................... 257/E51.049
See application file for complete search history.

(56) References Cited

U.S. PATENT DOCUMENTS

| | | | |
|---|---|---|---|
| 2005/0156164 A1* | 7/2005 | Sotoyama | 257/40 |
| 2005/0238910 A1 | 10/2005 | Ionkin et al. | |
| 2005/0238920 A1* | 10/2005 | Sotoyama et al. | 428/690 |
| 2006/0154107 A1* | 7/2006 | Kubota et al. | 428/690 |
| 2007/0167626 A1 | 7/2007 | Kim et al. | |

FOREIGN PATENT DOCUMENTS

| | | | |
|---|---|---|---|
| CN | 1960957 | 5/2007 | |
| CN | 1977301 | 6/2007 | |
| CN | 101003508 | 7/2007 | |
| CN | 101080376 | 11/2007 | |
| JP | 2009/035516 A * | 2/2009 | ............. C07C 15/38 |
| WO | WO 2006/057326 | 6/2006 | |

OTHER PUBLICATIONS

English language machine translation of JP 2009/035516 A, 2009.*
"Charge-Charge Injection Characteristics At Organic/Organic Heterojunction Interfaces in Organic Light-Emitting Diodes"; Matsushima, et al.; Chemical Physics Letters; 435 (4-6), 2007, 327-330.

* cited by examiner

*Primary Examiner* — Michael H Wilson
(74) *Attorney, Agent, or Firm* — McKenna, Long & Aldridge LLP

(57) ABSTRACT

Disclosed is an organic light emitting material having the following chemical formula, for improving luminous efficiency,

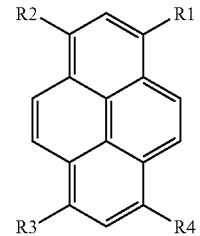

where R1, R2, R3 and R4 denote materials selected from an aromatic group with 6-24 carbon atoms (C6-C24), the group being independently substituted or unsubstituted, preferably, an aromatic group with 6-24 carbon atoms (C6-C24), the group consisting of trimethylsilane (TMS), CN, halogen (F, Cl, Br) alkyl groups with 1-4 carbon atoms (C1-C4).

3 Claims, 1 Drawing Sheet

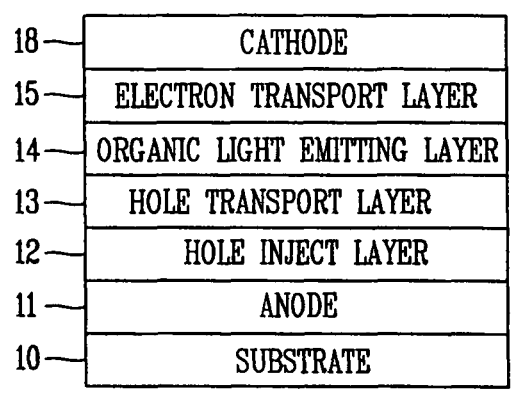

ORGANIC LIGHT EMITTING MATERIAL AND ORGANIC LIGHT EMITTING DEVICE USING THE SAME

CROSS-REFERENCE TO RELATED APPLICATION

Pursuant to 35 U.S.C. §119(a), this application claims the benefit of earlier filing date and right of priority to Korean Application No. 10-2008-0137517, filed on Dec. 30, 2008, the contents of which are incorporated by reference herein in its entirety.

BACKGROUND OF THE INVENTION

1. Field of the Invention

The present invention relates to an organic light emitting material and an organic light emitting device using the same, and particularly, to an organic light emitting material capable of enhancing luminous efficiency (light emitting efficiency) of an organic light emitting device and lowering a driving voltage, and an organic light emitting device using the same.

2. Background of the Invention

Recently, since an organic light emitting device using poly (p-phenylenevinylene) (PPV) as one of conjugated polymers was developed, studies on organic substance, such as the conjugated polymers, with conductivity have been actively conducted. Also, studies on applying those organic materials to thin film transistors, sensors, lasers, photoelectric devices and the like are undergoing. Among others, a study on an organic light emitting device is being conducted most actively.

For an electroluminescent device formed of a phosphorous inorganic substance, more than 200V of AC driving voltage is needed and a fabrication process of the device is executed by vacuum plating. Accordingly, it has several disadvantages on high fabrication cost as well as difficulty in implementing a larger device, particularly, difficulty in blue light emission. However, the light emitting device formed of organic substance is spotlighted as a next generation display device in terms of enabling development of flexible light emitting device in addition to excellent luminous efficiency, facilitation of fabricating a larger device, simplified process, particularly, facilitation of blue light emission and the like.

In the related art, a compound having amine branching at biphenyl, as expressed in Chemical Formula 1, was developed as an organic light emitting material for the organic light emitting device, particularly, a blue organic light emitting device. In the organic light emitting device, high luminous efficiency of a material is ensured only for high internal quantum efficiency, but in this case, a problem has occurred that it is difficult to obtain blue color with high purity.

[Chemical Formula 1]

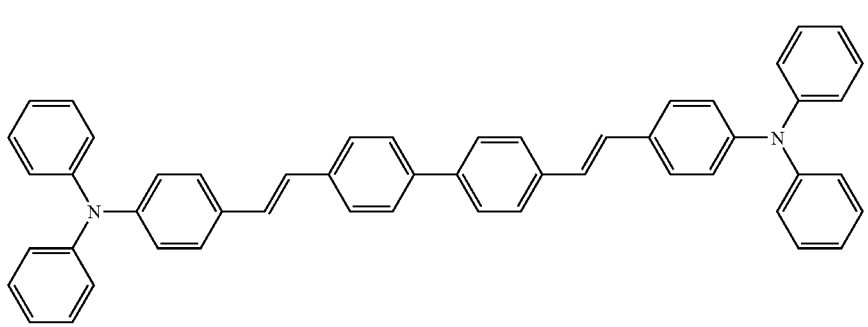

U.S. Pat. No. 6,455,720 discloses 2,3-(diaryl)vinylphosphine as the blue organic light emitting material. Korean Laid-open Application No. 2002-0070333 discloses blue light emitting compound having a central portion in a diphenylanthracene structure and aryl group substituted with a terminal.

However, even in case of using the blue light emitting compound, a problem of insufficient luminous efficiency and brightness has occurred. That is, for using the blue light emitting compound as a blue organic light emitting device, low blue purity makes it difficult to render dark blue color, which accordingly causes a difficulty in rendering full natural colors.

SUMMARY OF THE INVENTION

Therefore, an object of the present invention is to provide an organic light emitting material capable of implementing a novel dark blue color and rendering full colors, and an organic light emitting device using the same.

To achieve these and other advantages and in accordance with the purpose of the present invention, as embodied and broadly described herein, there is provided a chemical formula of an organic light emitting material is defined as follows,

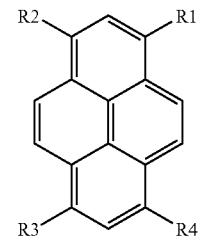

where R1, R2, R3 and R4 are materials selected from an aromatic group having 6 to 24 carbon atoms (C6-C24), the group being independently substituted or unsubstituted, R1=R3 and R2=R4 or R1=R2=R3=R4.

Here, the aromatic group may consist of phenyl, biphenyl, naphthyl, phenanthrene and terphenyl. When R1, R2, R3 and R4 are substituted, substituents of R1, R2, R3 and R4 may be selected from a group consisting of phenyl, biphenyl, naphthyl, phenanthrene, terphenyl and substituents of the of phenyl, biphenyl, naphthyl, phenanthrene and terphenyl.

In another aspect of the present invention, there is provided a chemical formula of an organic light emitting material as follows,

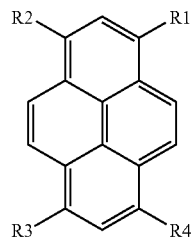

where R1 and R2 are selected from an aromatic group having 6 to 24 carbon atoms (C6-C24) being independently substituted or unsubstituted.

The present invention can enhance brightness and minimize a driving voltage by developing a novel dopant added to a host material.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 is a view showing a structure of an organic light emitting device in accordance with the present invention.

DETAILED DESCRIPTION OF THE INVENTION

The present invention provides a blue fluorescent dopant with high color purity and high efficiency. The dopant according to the present invention is added to a host material to form a blue organic light emitting layer.

FIG. 1 shows a schematic structure of an organic light emitting device having an organic light emitting layer having a dopant added thereto according to the present invention.

As shown in FIG. 1, an anode 11 composed of a metal with high work function and a cathode 18 composed of a metal with low work function are formed on a substrate 10 formed of a transparent material, such as glass, and an organic light emitting layer 14 is inserted between the anode 11 and the cathode 18. Accordingly, hole is injected from the anode 11 to the organic light emitting layer 14 and electron is injected from the cathode 18.

Upon hole and electron being injected into the organic light emitting layer 14, exciton is generated within the organic light emitting layer 14. As the exciton emits light and is decayed, light corresponding to an energy difference between lowest unoccupied molecular orbital (LUMO) and highest occupied molecular orbital (HOMO) of the organic light emitting layer 14 is generated.

A metallic oxide, such as transparent indium tin oxide (ITO), with high work function may be employed as the anode 11, and a metal, such as Ca or Mg, with low work function may be employed as the cathode 18. Here, since such metals are unstable, a stabilized Al may preferably be used. Here, an energy barrier formed of LiF may be formed between the organic light emitting layer 14 and the cathode 18 composed of Al, so as to lower a driving voltage of the organic light emitting device and facilitate an electron injection into the organic light emitting layer 14.

In order to improve luminous efficiency of the organic light emitting device having such structure, a hole inject layer 12 and a hole transport layer 13 are formed between the anode 11 and the organic light emitting layer 14, and an electron transport layer 15 is formed between the organic light emitting layer 14 and the cathode 18. Charge transport layers, such as the hole transport layer 13 and the electron transport layer 15, efficiently transport carriers to a light emitting material so as to increase the light coupling probability within a light emitting layer, thereby enhancing luminous efficiency of the organic light emitting layer. Further, since HOMO or LUMO level of a charge transport material and HOMO or LUMO level of the organic light emitting layer do not completely correspond to each other, the charge transport layers serve to block the movement of carriers. For instance, an electron transport layer blocks a hole flow at an interface with a light emitting layer so as to increase an electric field therein, whereby an electron injection from a cathode is improved, resulting in enhancement of luminous efficiency.

Copper phthalocyanine (CuPu) with a chemical structure as expressed in Chemical Formula 2 is used as the hole inject layer 12. 4,4'-bis[N-(1-naphthyl)-N-phenthylamino]-biphenyl (NPD) with a chemical structure as expressed in Chemical Formula 3 is used as the hole transport layer 13.

[Chemical Formula 2]

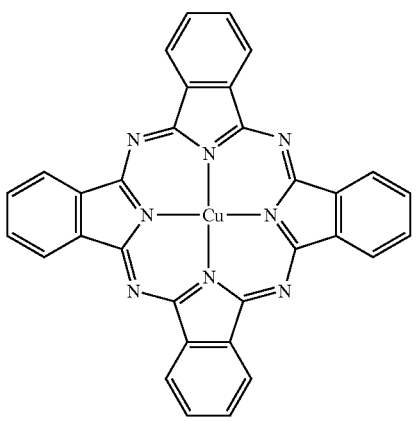

[Chemical Formula 3]

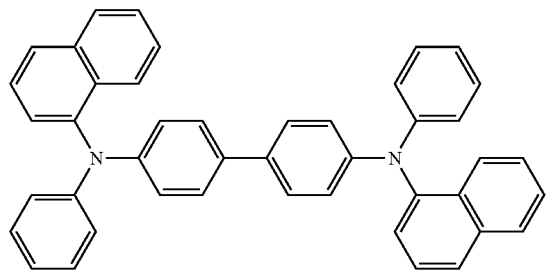

Tris(8-hydroxy-quinolatealuminum (Alq₃) with a chemical structure of Chemical Formula 4 is used as the electron transport layer 15. Here, an electron inject layer may be formed between the cathode 18 and the electron transport layer 15; however, in the structure of the present invention, since the electron is smoothly injected by the LiF energy barrier and the electron is also smoothly transported by the Alq₃, the electron inject layer has not been formed (alternatively, the electron inject layer may also be formed).

[Chemical Formula 4]

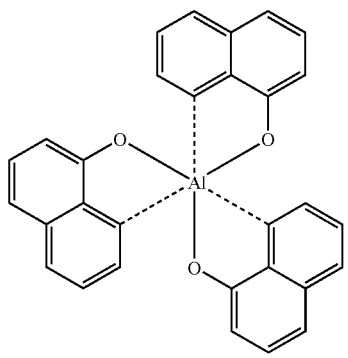

The organic light emitting layer 14 may be composed of host and dopant. Here, 4,4'-bis(2,2-diphenylvinyl-1,1'-iphenyl) (DPVBi) with a chemical structure as defined in Chemical Formula 5 is used as the host material.

[Chemical Formula 5]

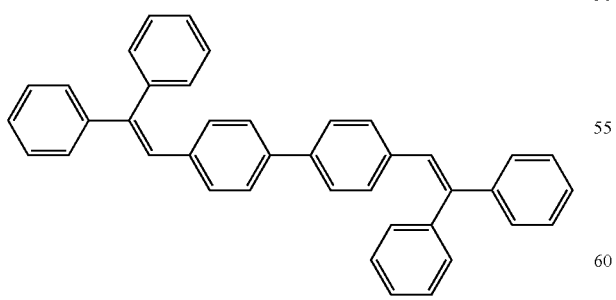

The organic light emitting layer 14 is obtained by adding a dopant to the structured host material. A chemical structure of the compound composing the dopant can be defined by Chemical Formula 6.

[Chemical Formula 6]

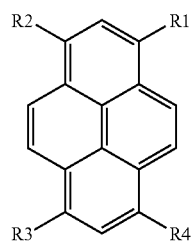

The compound defined by Chemical Formula 6 is a blue fluorescent compound for emitting blue light. Here, about 5% of the structured blue fluorescent compound in the above structure is added to the host DPVBi such that blue light with enhanced luminous efficiency can be emitted from the organic light emitting layer 14. Here, R1=R3 and R2=R4 or R1=R2=R3=R4.

In Chemical Formula 6, R1, R2, R3 and R4 may be selected from an aromatic group being independently substituted or unsubstituted, preferably, from an aromatic group with 6 to 24 carbon atoms (C6-C24), the group consisting of trimethylsilane (TMS), CN, halogen (F, Cl, Br), alkyl groups with 1 to 4 carbon atoms (C1-C4). Also, R1, R2, R3 and R4 may be materials selected from an aromatic group consisting of phenyl, biphenyl, naphthyl, phenanthrene and therphenyl.

Substituents of R1 and R3 and R2 and R4 which are substituted or unsubstituted at Chemical Formula 6 may be selected from phenyl, biphenyl, naphthyl, phenanthrene, therphenyl and substituents thereof.

A detailed example of compound according to the present invention having the structure defined by Chemical Formula 6 can be expressed by Chemical Formula 7 as follows.

[Chemical Formula 7]

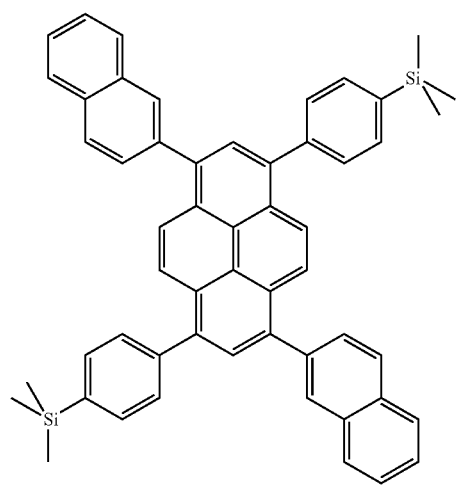

BD-1

BD-5
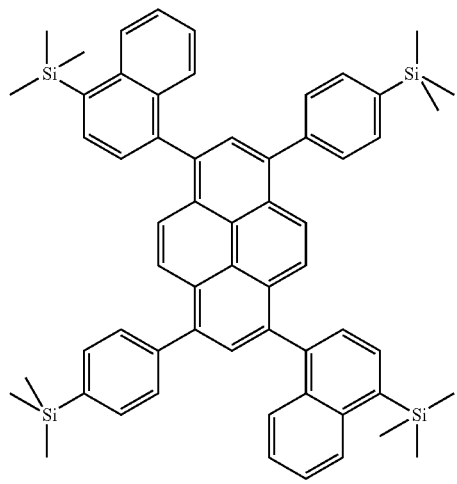
BD-24
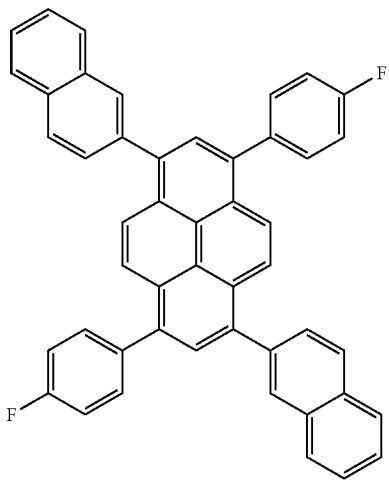
BD-34
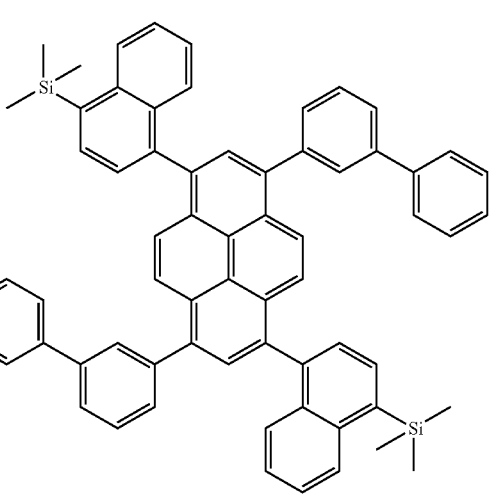
BD-23
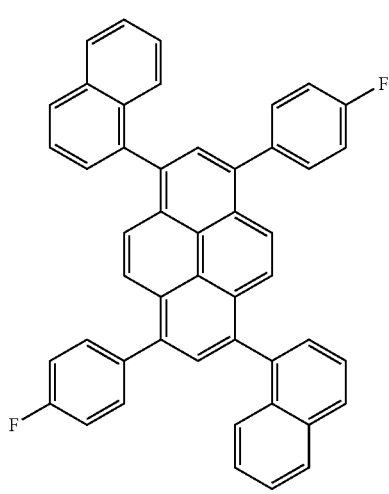
BD-35
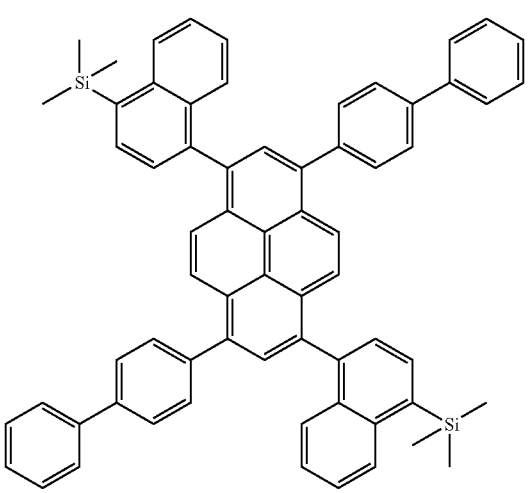

BD-37
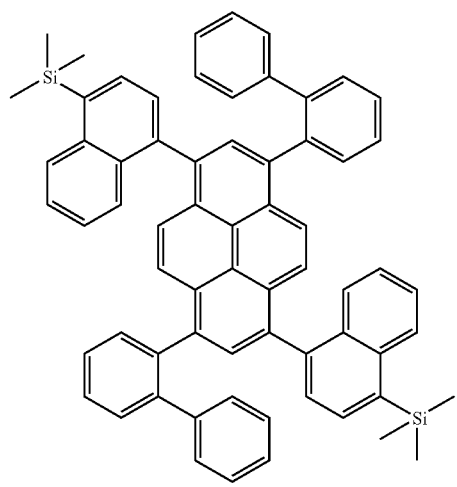
BD-38
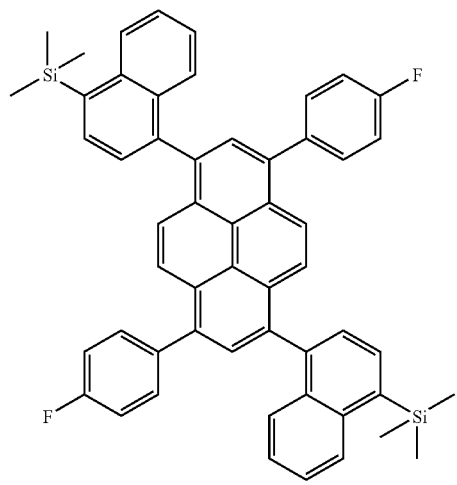
BD-39
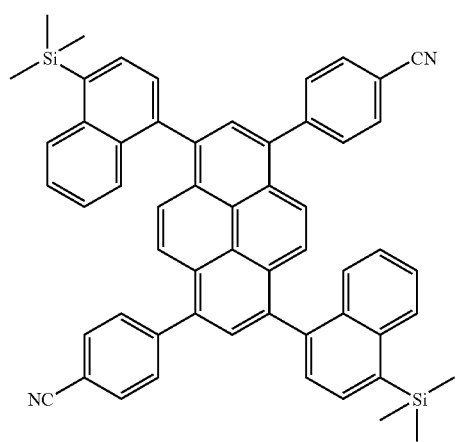
BD-40
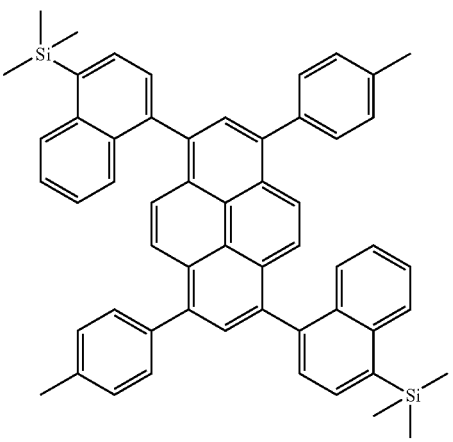
BD-41
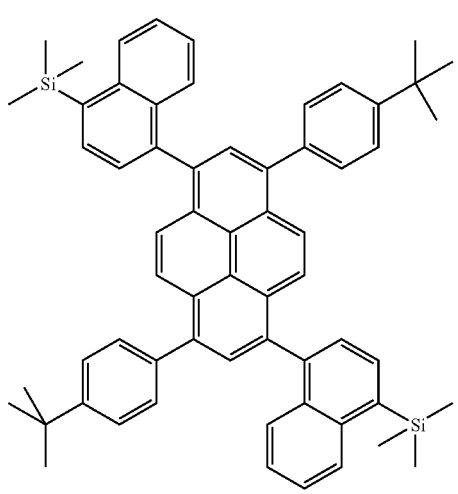
BD-42
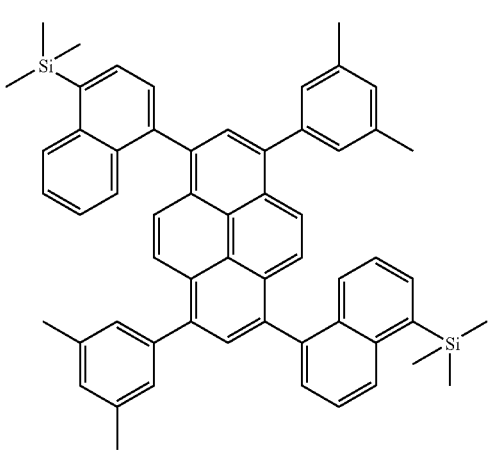

BD-43
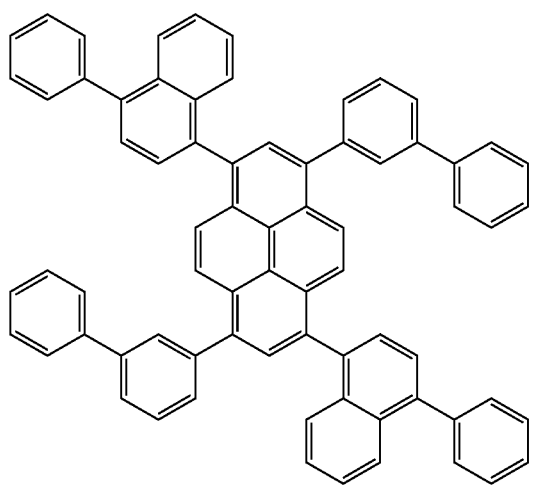
BD-47
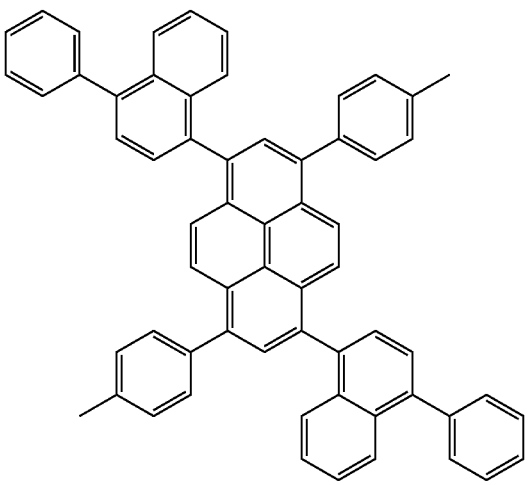
BD-44
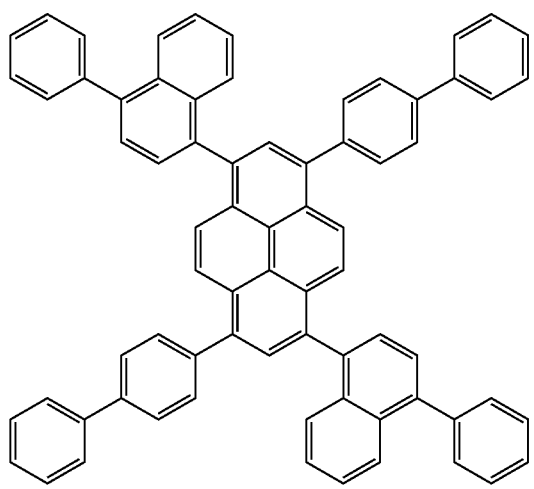
BD-48
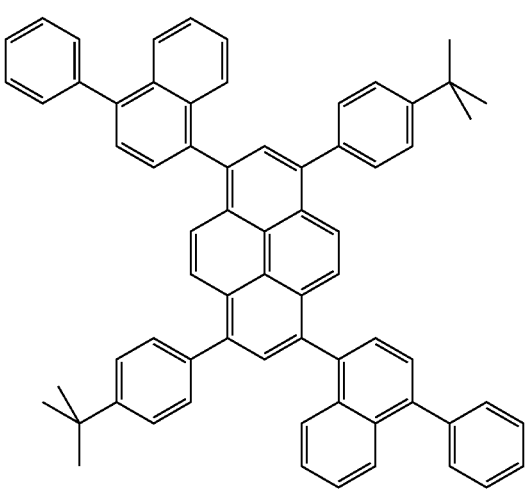
BD-46
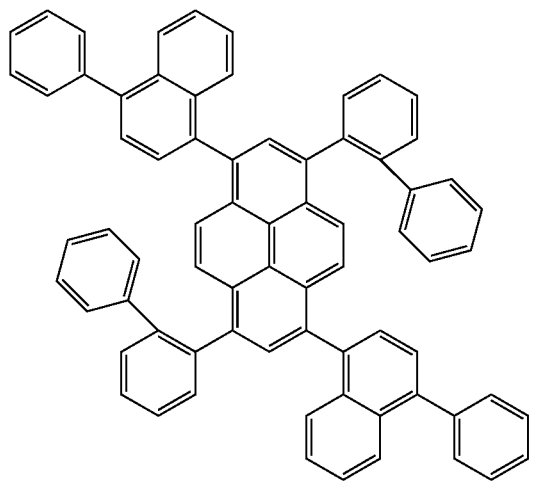
BD-49
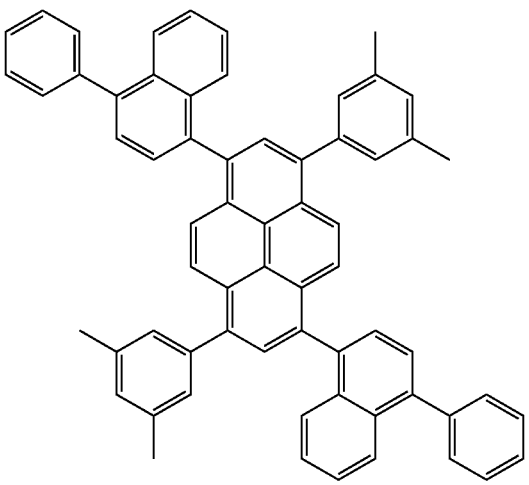

BD-50
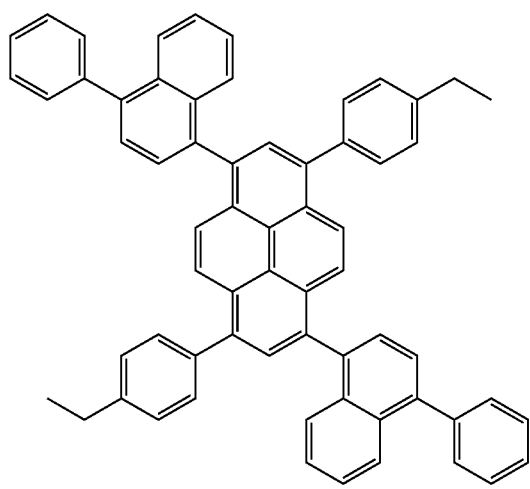
BD-54
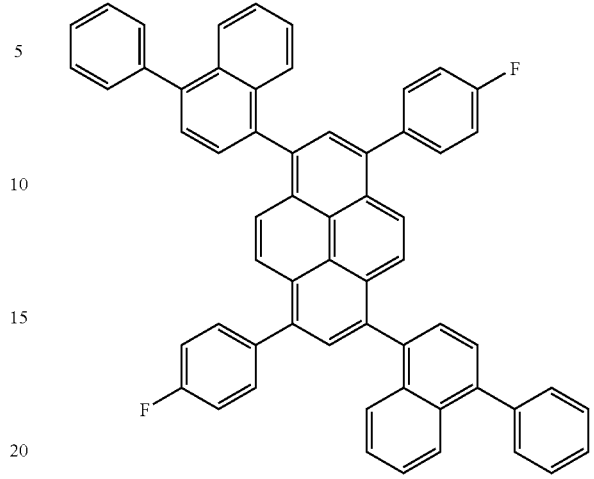
BD-52
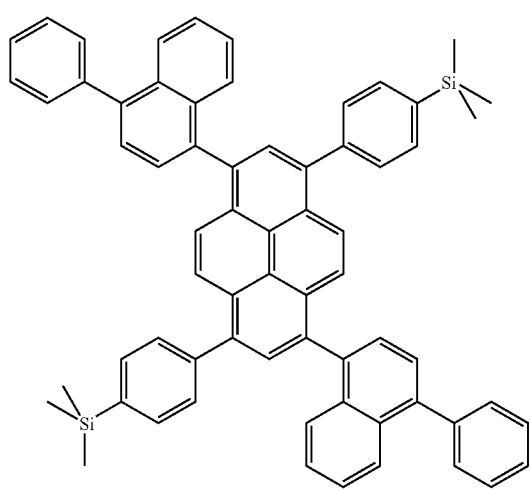
BD-60
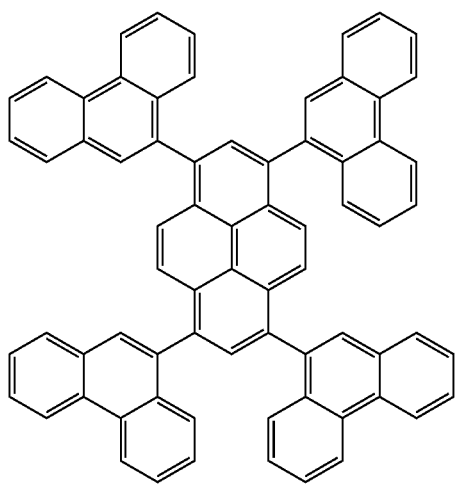
BD-53
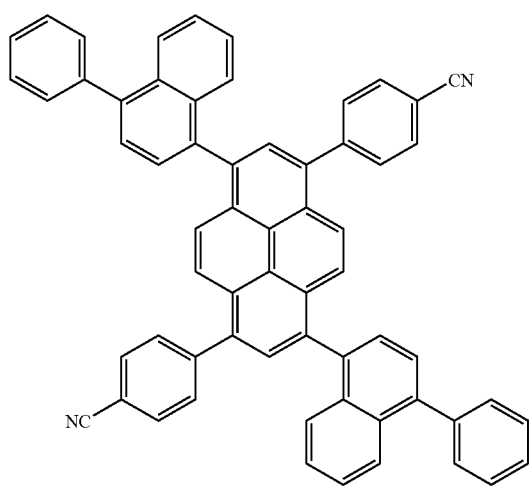
BD-62
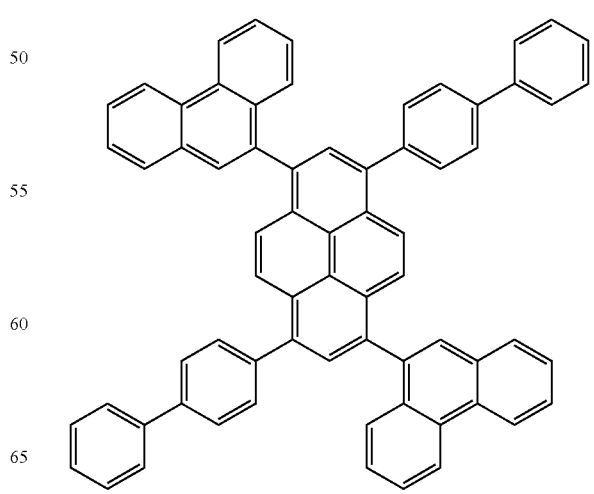

BD-63
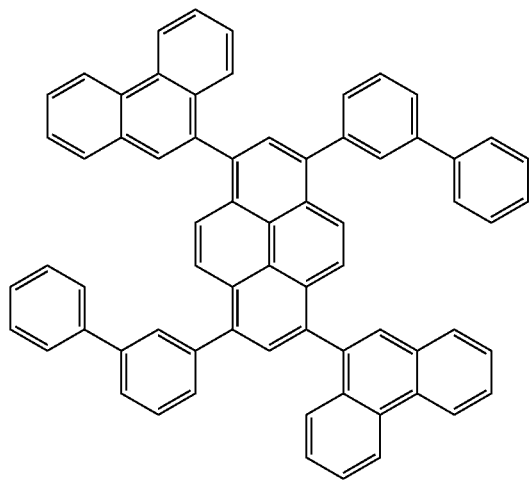
BD-64
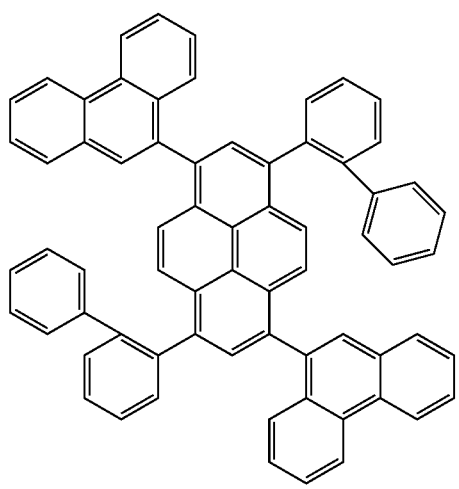
BD-65
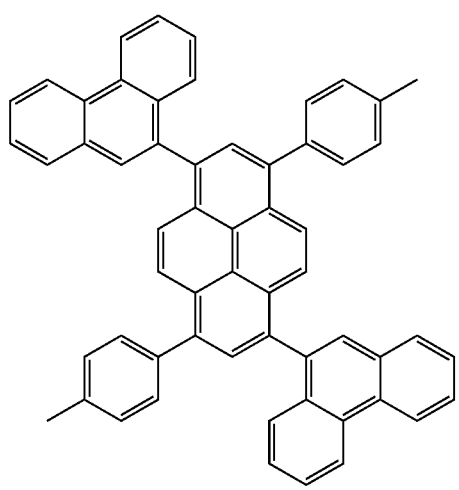
BD-66
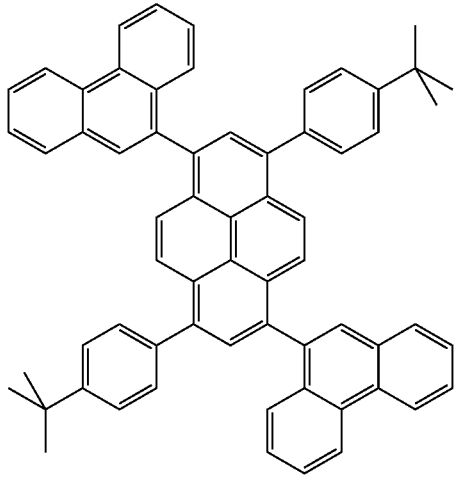
BD-67
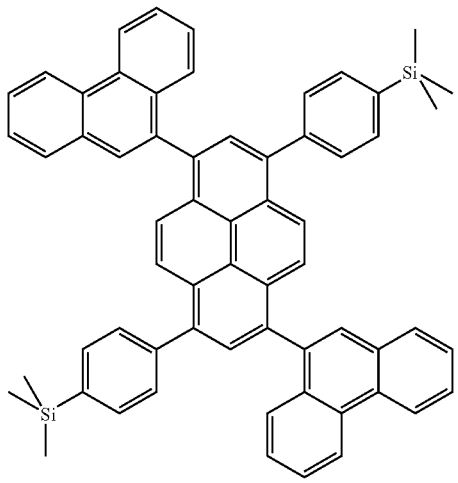
BD-68
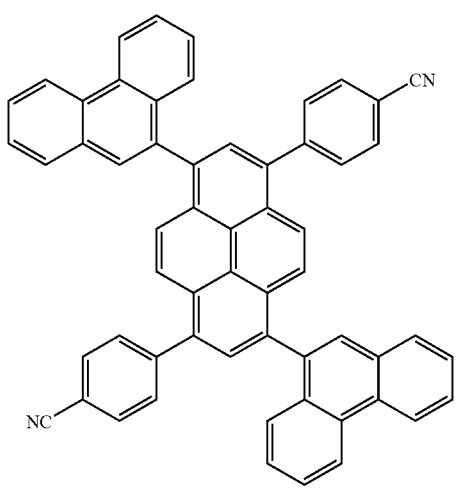

BD-69
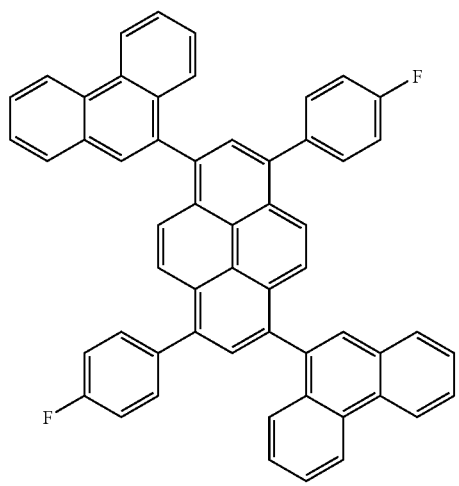
BD-71
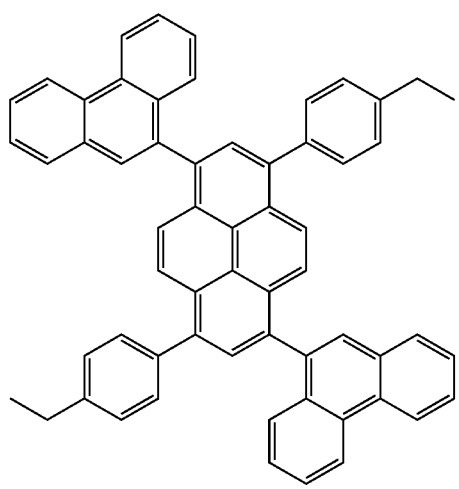
BD-72
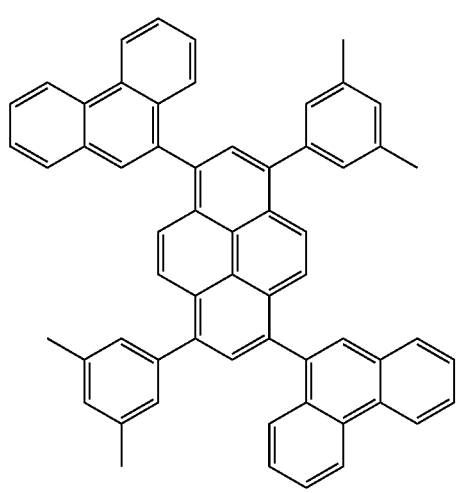
BD-73
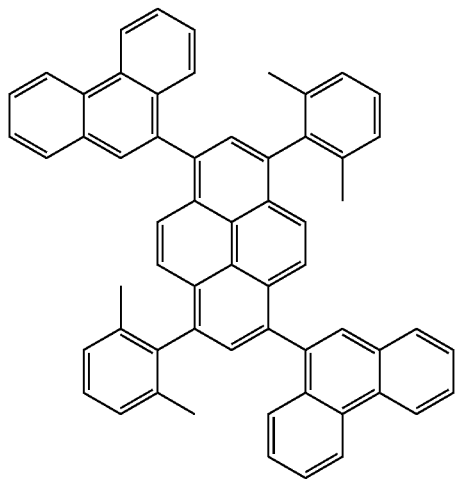
BD-87
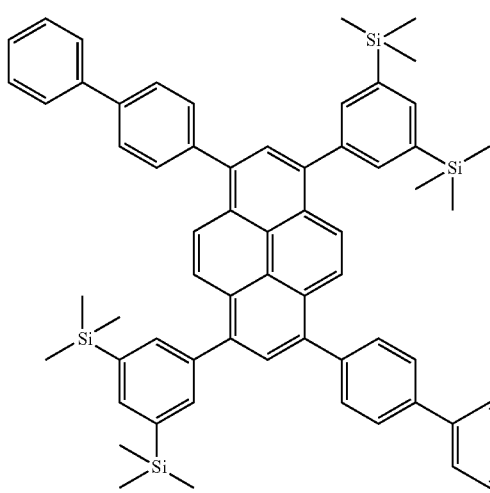
BD-94
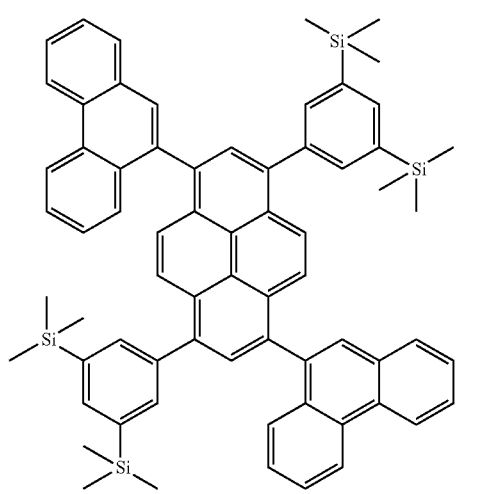
A compound having one of the above chemical structures is added to the host material composed of 4,4'-bis(2,2-diphenylvinyl)-1,1'-iphenyl) (DPVBi), thereby forming a blue organic light emitting layer.
In the meantime, a dopant in a different structure proposed in the present invention will be defined by Chemical Formula 8.

[Chemical Formula 8]

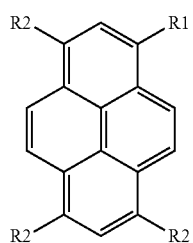

where R1 and R2 may be selected from an aromatic group with 6 to 24 carbon atoms (C6-C24) being independently substituted or unsubstituted, preferably, from an aromatic group having 6 to 24 carbon atoms (C6-C24), the group consisting of trimethylsilane (TMS), CN, halogen (F, Cl, Br), alkyl groups with 1 to 4 carbon atoms (C1-C4). Especially, in the present invention, R1 may be substituted with a material selected from an aromatic group with 6 to 24 carbon atoms (C6-C24), the group consisting of phenyl, biphenyl, naphthyl, phenanthrene and terphenyl. R2 may be a different material selected from the aromatic group with 6 to 24 carbon atoms (C6-C24), the group consisting of phenyl, biphenyl, naphthyl, phenanthrene and terphenyl, heterocyclic groups, aliphatic groups and pyrene series substituted with carbon.

In more detail, the substituents of R1 and R2 may be selected from a group consisting of phenyl, biphenyl, naphthyl, phenanthrene and terphenyl all of which are substituted or not substituted, and substituents of the of phenyl, biphenyl, naphthyl, phenanthrene and terphenyl.

Detailed examples of compounds according to the present invention defined by Chemical Formula 8 will be expressed by Chemical Formula 9.

[Chemical Formula 9]

BD-1

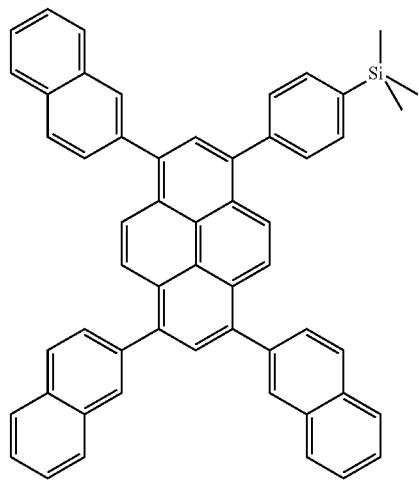

BD-5

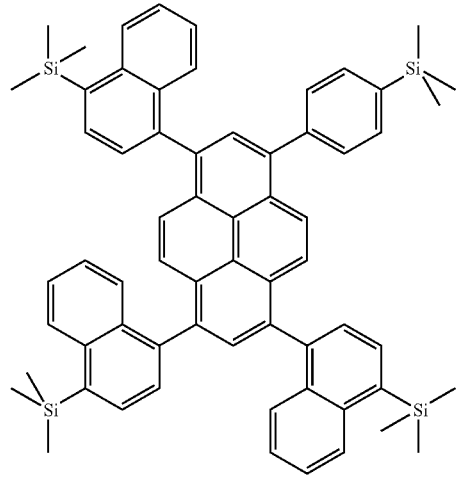

BD-23

BD-24

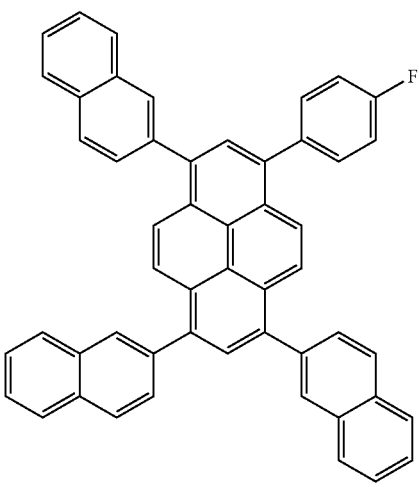

BD-34
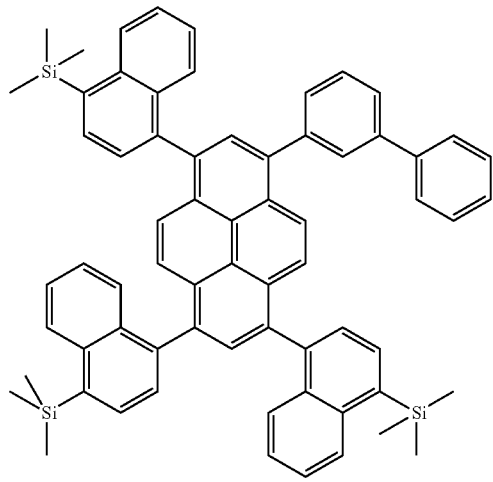
BD-38
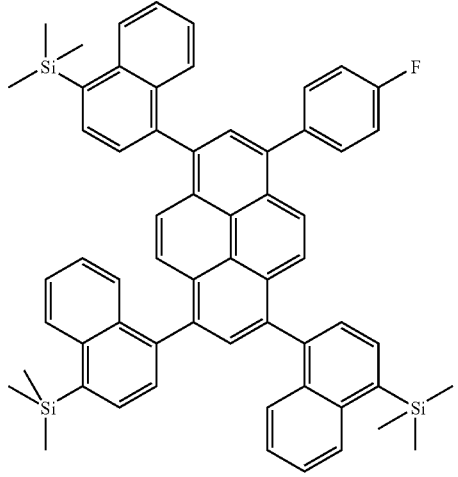
BD-35
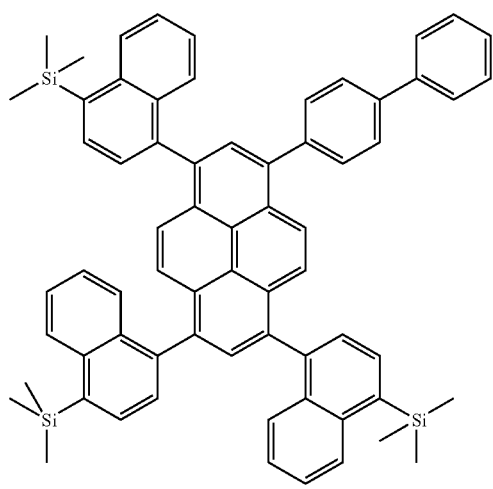
BD-39
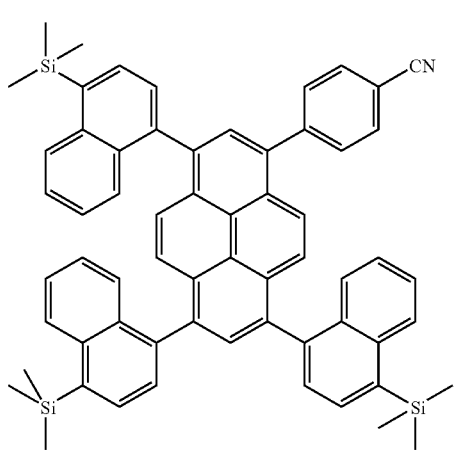
BD-37
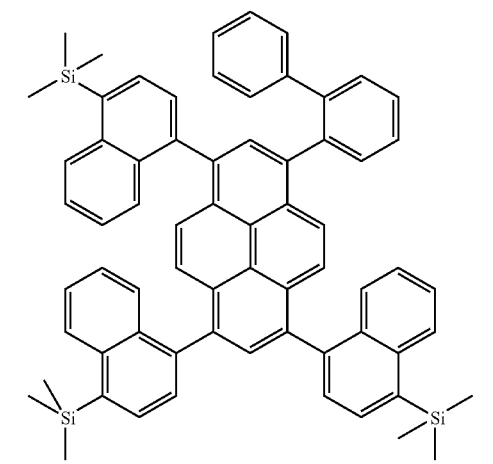
BD-40
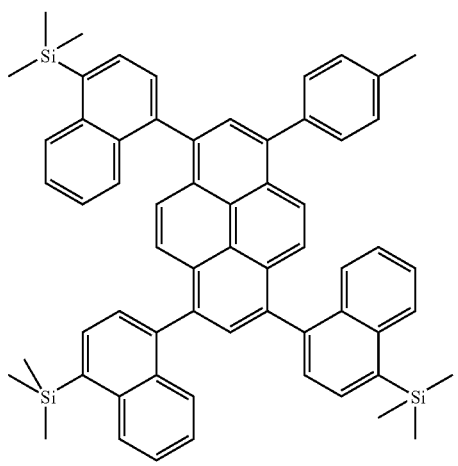

BD-41
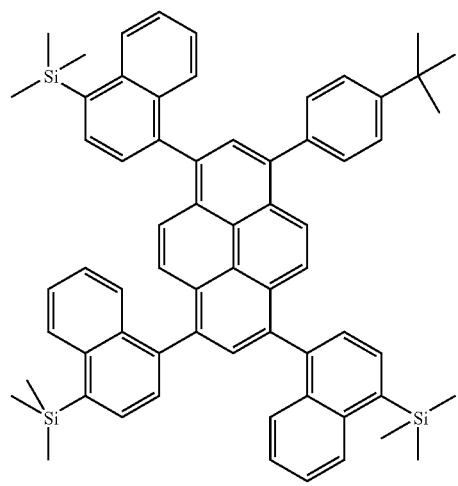
BD-42
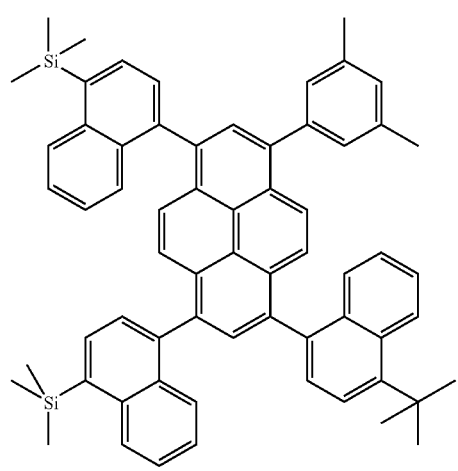
BD-43
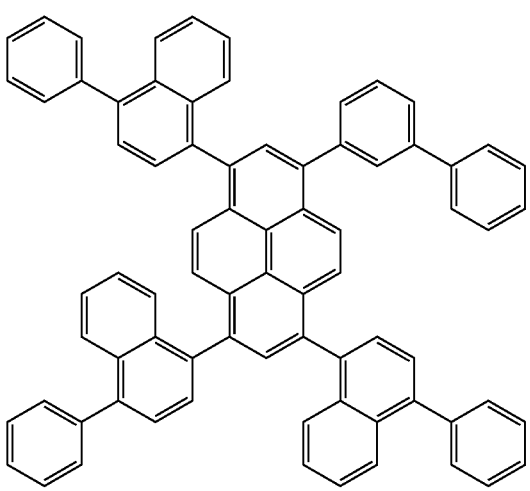
BD-44
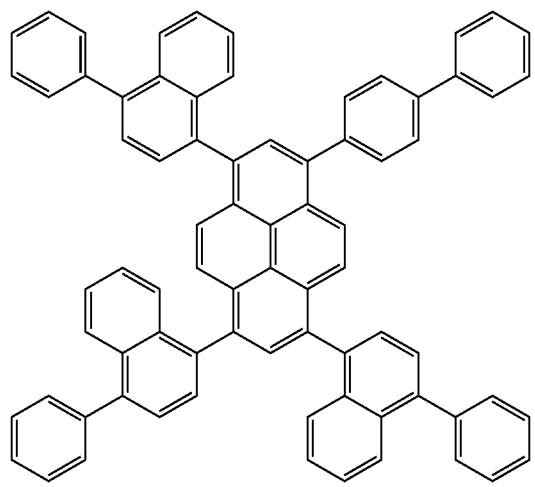
BD-46
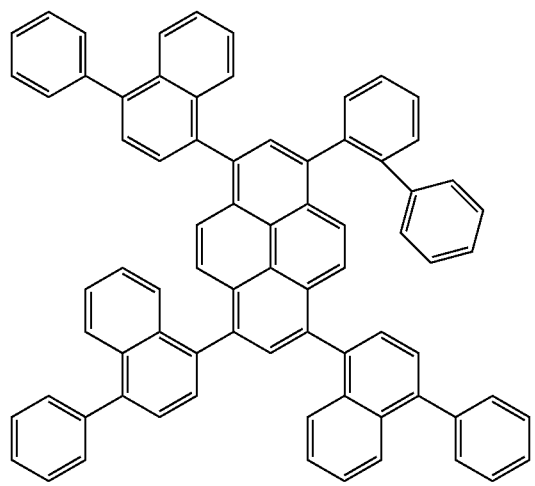
BD-47
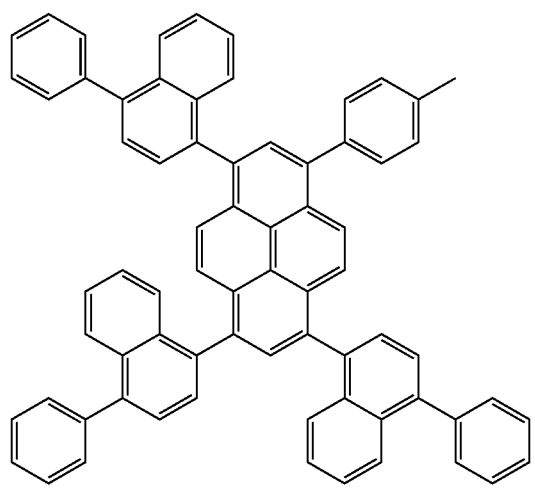

BD-48
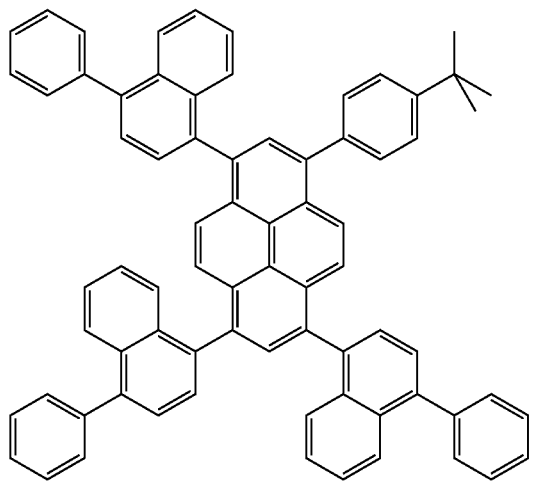
BD-52
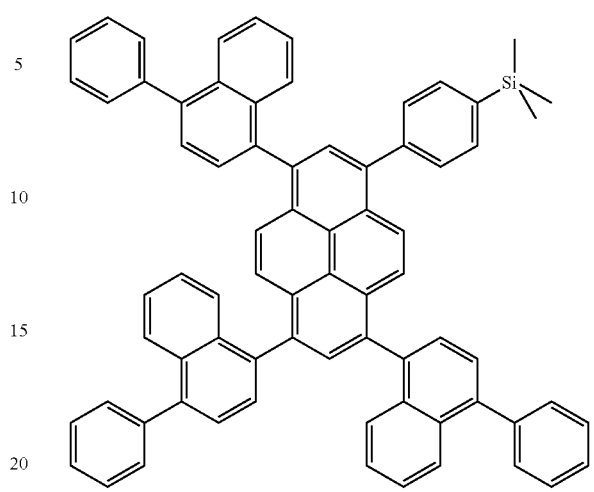
BD-49
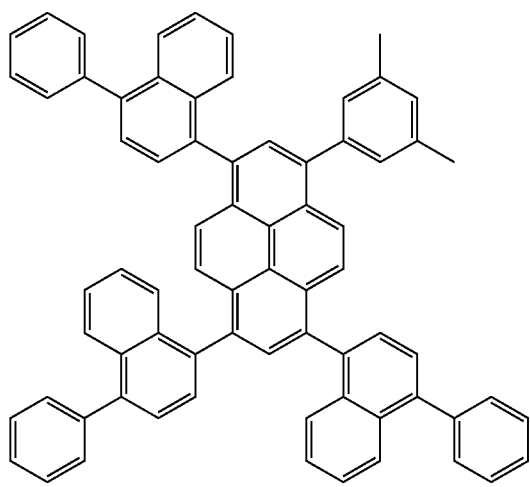
BD-53
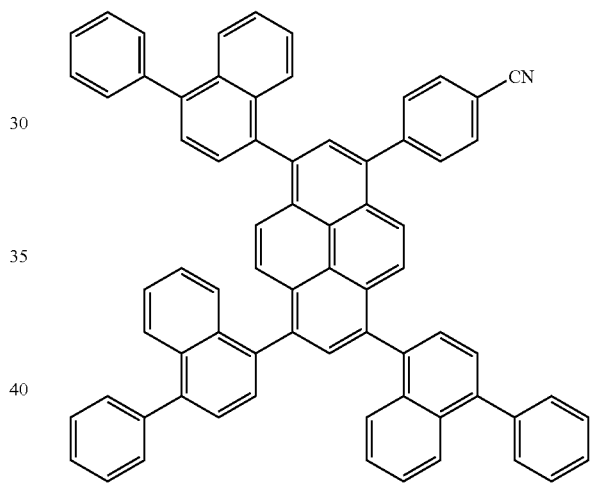
BD-50
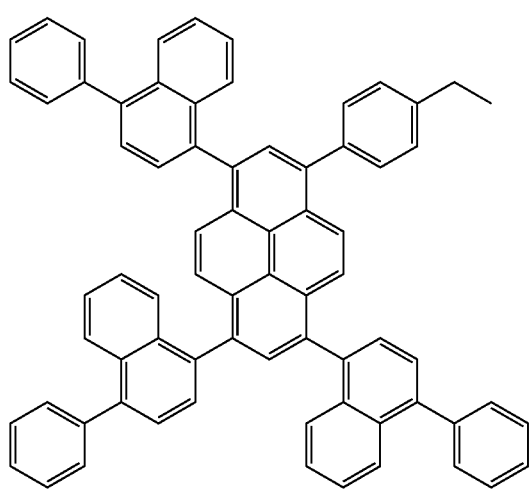
BD-54
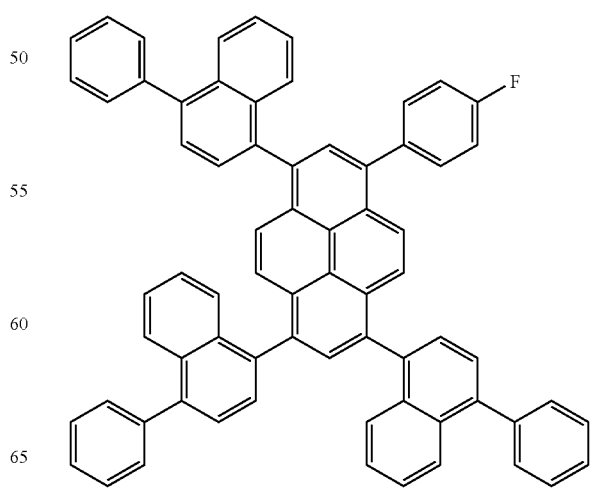

-continued
BD-62
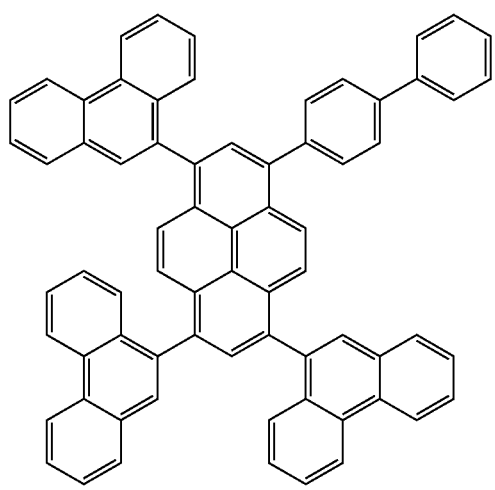
BD-65
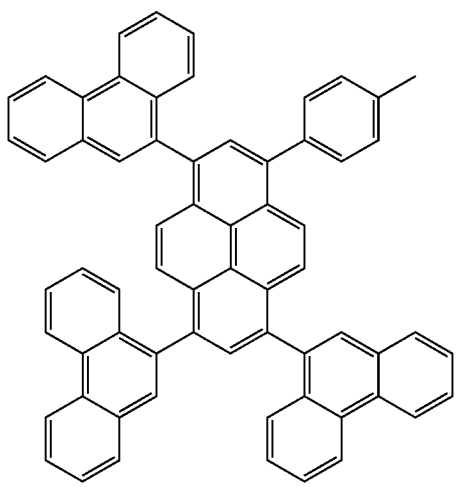
BD-63
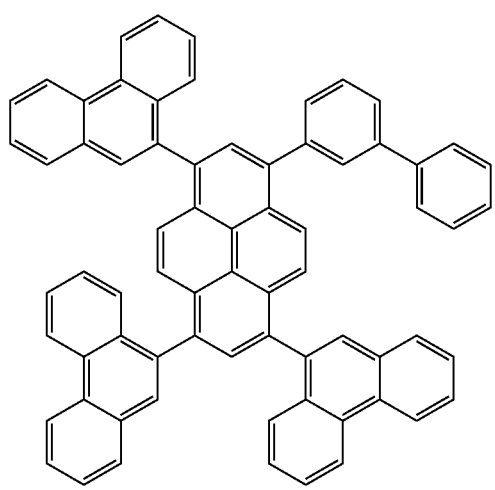
BD-66
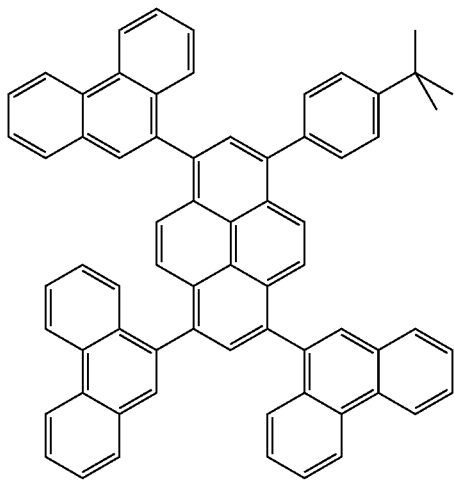
BD-64
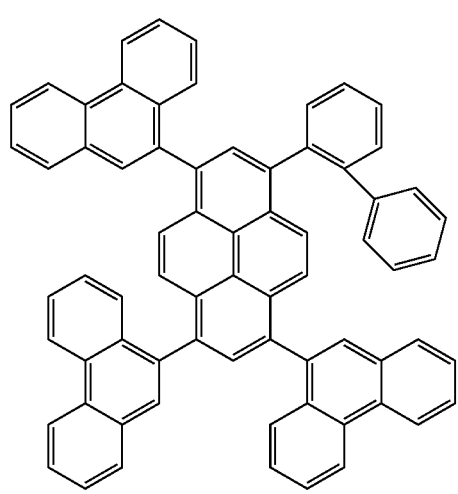
BD-67
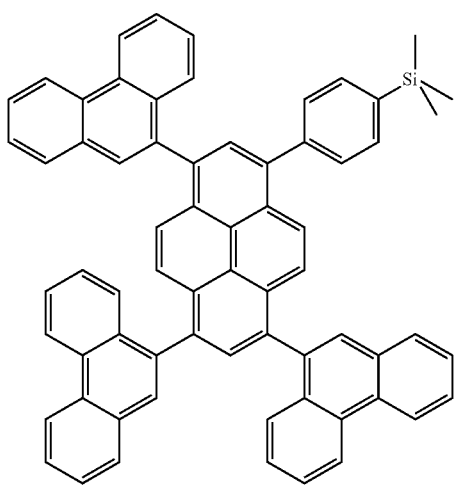

BD-68
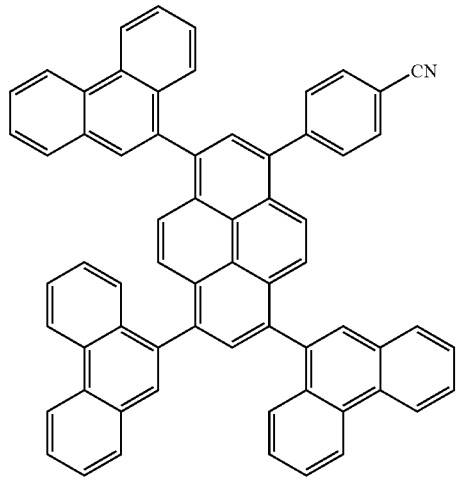
BD-72
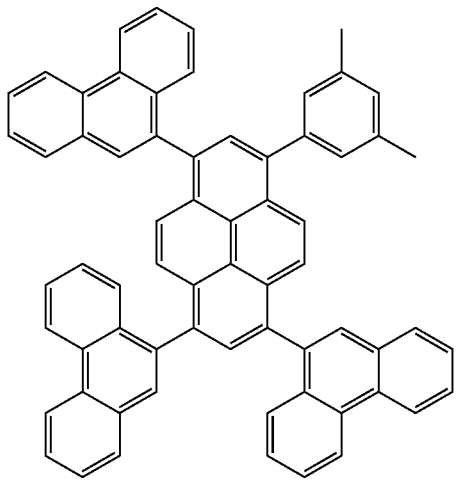
BD-69
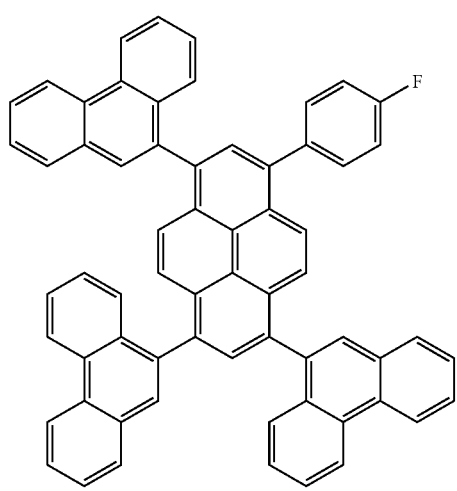
BD-73
BD-71
BD-86
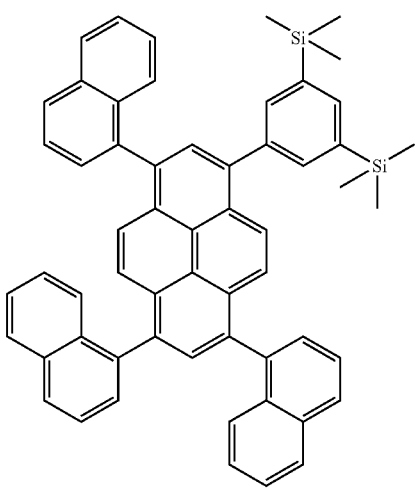

-continued

BD-85

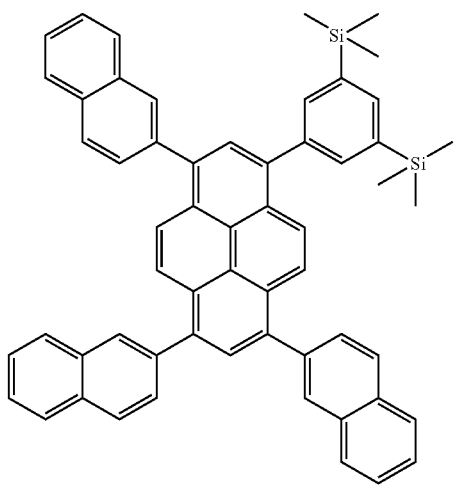

BD-94

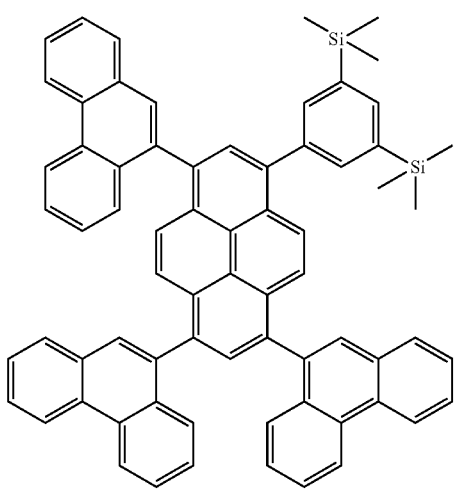

A compound having one of the above chemical structures is added to the host material composed of 4,4'-bis(2,2-diphenylvinyl)-1,1'-iphenyl) (DPVBi), thereby forming a blue organic light emitting layer.

Hereinafter, description will be given of a method for fabricating an organic light emitting device having a blue organic light emitting layer having a dopant added thereto according to the present invention. Here, the organic light emitting device has the structure shown in FIG. 1. However, the specific structure of the organic light emitting device and a specific fabrication method are merely illustrative, so they should not be construed to limit the present invention. An actually fabricated organic light emitting device has a more complicated structure than the structure shown in FIG. 1, but a relatively simple structure will be described for a clear explanation.

Hereinafter, Synthesis Examples of compounds created according to the present invention and Embodiments of fabricating an organic light emitting device using those compounds will be described. Here, for the sake of explanation, a material in a structure defined by Chemical Formula 6 and a material in the structure defined by Chemical Formula 8 will be independently described.

First, Synthesis Examples and Embodiments of the material expressed in Chemical Formula 6 will be described as follows.

Synthesis Examples and Embodiments of Compound of Chemical Formula 6

Synthesis Example 1

Fabrication of BD-101 of Chemical Formula 7

(1) Synthesis of 1,6-diphenylpyrene

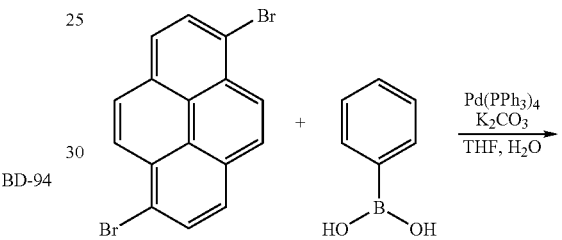

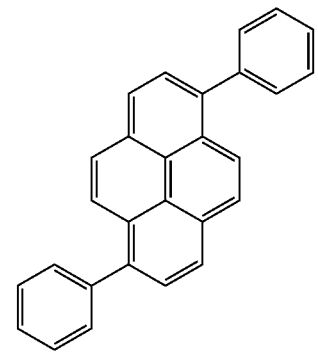

1,6-dibromopyrene (2 g, 5.56 mmol) and phenylboronic acid (1.40 g, 11.16 mmol) were put into a 2-neck round bottom flask filled with 80 ml of anhydrous tetrahydrofuran and stirred. Tetrakis(triphenylphosphine) palladium (0.30 g, 5 mol %), 20 g of potassium carbonate and 80 ml of distilled water were added into the same flask, which was then subjected to reflux at a temperature of 100° C. for 24 hours. After completion of the reaction, the tetrahydrofuran was removed and thusly generated solid was filtered. The filtered solid was recrystallized by dichloromethane and ethanol, thereby synthesizing 1,6-diphenylpyrene (1.81 g, 92%).

(2) Fabrication of 1,6-diphenyl-3,8-dibromopyrene

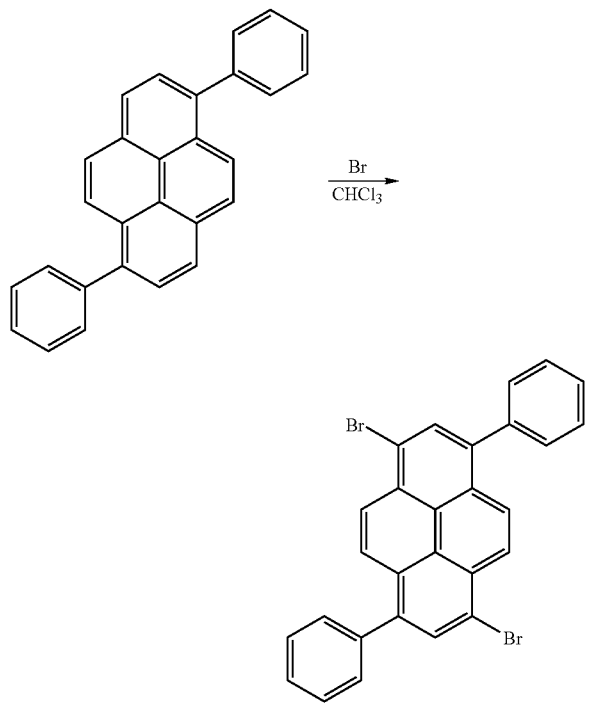

1,6-diphenylpyrene (2 g, 5.64 mmol) and 50 ml of chloroform were put into a 2-neck round bottom flask and stirred. Bromine (2.25 g, 14.10 mmol) was slowly dropped into the flask for 30 minutes and then refluxed at a temperature of 70° C. for 8 hours. After lowering the temperature down to room temperature, 100 ml of distilled water was poured into the refluxed mixture and then stirred. After filtering off generated solid, the filtered solid was washed with 50 ml of distilled water and 50 ml of ethanol, thereby fabricating 1,6-diphenyl-3,8-dibromopyrene (2.46 g, 85%).

(3) Fabrication of 1,6-di(4-biphenyl)-3,8-diphenylpyrene (BD-101)

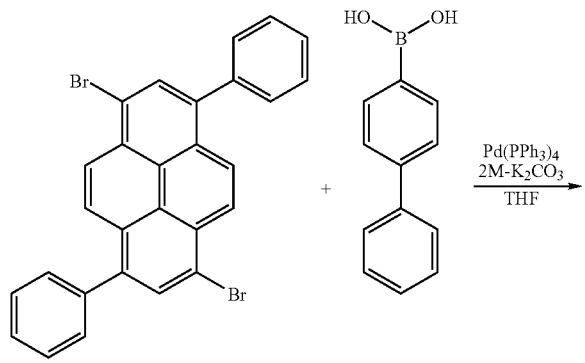

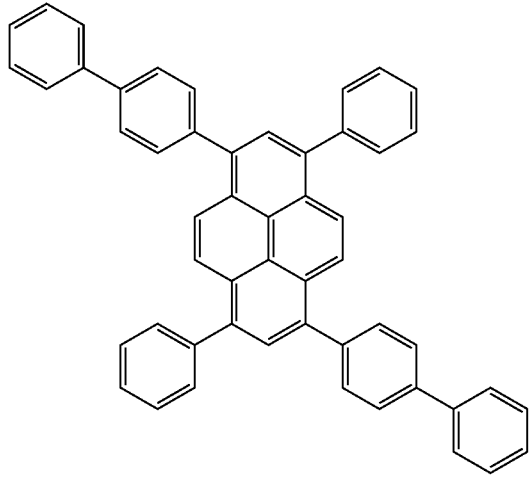

1,6-diphenyl-3,8-dibromopyrene (2 g, 3.90 mmol), 4-biphenylboronic acid (1.62 g, 8.20 mmol) and 80 ml of anhydrous tetrahydrofuran were put into a 2-neck round bottom flask and stirred. Tetrakis(triphenylphosphine) palladium (0.23 g, 5 mol %), 20 g of potassium carbonate and 80 ml of distilled water were added into the same flask, which was then subjected to reflux at a temperature of 100° C. for 24 hours. After completion of the reaction, the tetrahydrofuran was removed and thusly generated solid was filtered. The filtered solid was recrystallized by dichloromethane and ethanol, thereby synthesizing 1,6-di(4-biphenyl)-3,8-diphenylpyrene (2.18 g, 85%).

Synthesis Example 2

Fabrication of BD-128 of Chemical Formula 7

(1) Fabrication of 1,3,6,8-tetrabromopyrene

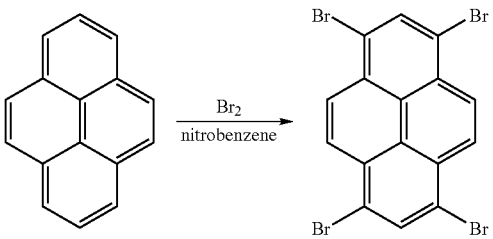

Pyrene (10 g, 50 mmol) and 100 ml of nitrobenzene were put into a 2-neck round bottom flask and stirred, and bromine (35.6 g, 200 mmol) was slowly dropped therein for 30 minutes. The mixture was then refluxed at a temperature of 130□ for 12 hours. After lowering the temperature down to room temperature, 200 ml of distilled water was poured into the refluxed mixture and then stirred, thus generating solid. After filtering off the generated solid, the filtered solid was washed with 100 ml of distilled water and 100 ml of ethanol, thereby fabricating 1,3,6,8-tetrabromopyrene (24 g, 95%).

(2) Fabrication of 1,3,6,8-tetrabiphenylpyrene

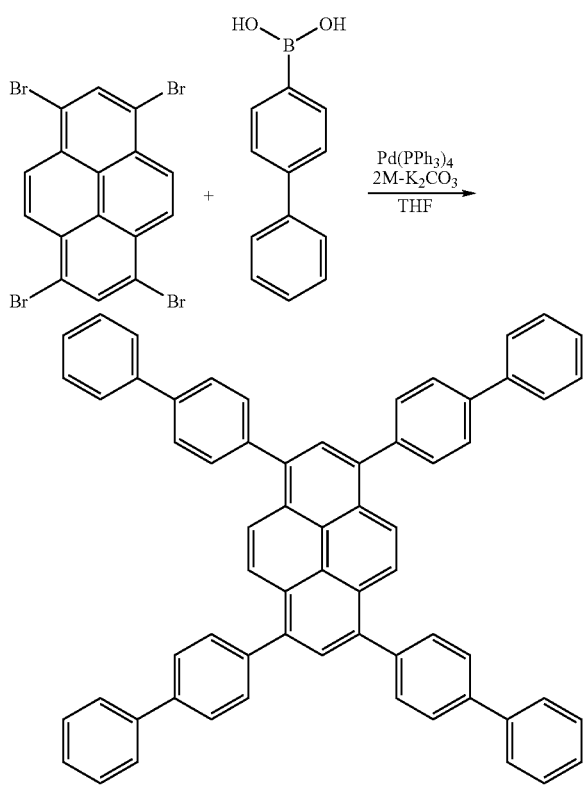

1,3,6,8-tetrabromopyrene (2 g, 3.86 mmol), 4-biphenylboronic acid (3.29 g, 16.60 mmol) and 80 ml of anhydrous tetrahydrofuran were put into a 2-neck round bottom flask and stirred. Tetrakis(triphenylphosphine) palladium (0.23 g, 5 mol %), 20 g of potassium carbonate and 80 ml of distilled water were added into the same flask, which was then subjected to reflux at a temperature of 100° C. for 24 hours. After completion of the reaction, the tetrahydrofuran was removed and thusly generated solid was filtered. The filtered solid was recrystallized by dichloromethane and ethanol, thereby synthesizing 1,3,6,8-tetrabiphenylpyrene (2.63 g, 84%).

An organic light emitting device using the compounds in the structure defined by Chemical Formula 6 and a fabrication method thereof will be described hereinafter. The organic light emitting device fabricated according to the embodiments as follows has the structure expressed in FIG. 1. However, the specific structure of the organic light emitting device may not limit the present invention but help understanding the description of the invention. That is, the following embodiments are merely illustrative for the present invention.

Conditions, for example, a thickness of a layer or the like, illustrated in the following description are merely exemplary to help understanding the description of the present invention.

Embodiment 1 Using Compound with Structure of Chemical Formula 6

ITO was patterned on a substrate in a size of 3×3 mm and washed. The washed substrate was attached onto a vacuum chamber and thereafter the vacuum chamber was made to be in a vacuum state with a 1×10-torr basal pressure. Afterwards, 200 Å of organic light emitting material, 350 Å of $Alq_3$, 5 Å of LiF and 1000 Å of Al were sequentially deposited on the ITO, wherein the organic light emitting material has 5% of BD-2 of Chemical Formula 6 as a dopant added to its host material composed of CuPC (200 Å), NPD (400 Å) and DPVBi, thereby sequentially forming, on an anode, a hole inject layer, a hole transport layer, an organic light emitting layer, an electron transport layer and a cathode.

For the organic light emitting device in this structure, upon applying a current of 0.9 mA, brightness ($cd/m^2$) was 616 $cd/m^2$, a driving voltage (V) was 4.36V, color coordinates (CIE) were x=0.145 and y=0.143.

Embodiment 2 Using Compound with Structure of Chemical Formula 6

An organic light emitting device fabricated according to Embodiment 2 was as same as that in Embodiment 1 excluding that 5% of BD-25 of Chemical Formula 7 was added as a dopant to the host material.

For the organic light emitting device in this structure, upon applying a current of 0.9 mA, brightness ($cd/m^2$) was 482 $cd/m^2$, a driving voltage (V) was 4.38V, color coordinates (CIE) were x=0.146 and y=0.141.

Embodiment 3 Using Compound with Structure of Chemical Formula 6

An organic light emitting device fabricated according to Embodiment 3 was as same as that in Embodiment 1 excluding that 5% of BD-52 of Chemical Formula 7 was added as a dopant to the host material.

For the organic light emitting device in this structure, upon applying a current of 0.9 mA, brightness ($cd/m^2$) was 585 $cd/m^2$, a driving voltage (V) was 4.54V, color coordinates (CIE) were x=0.146 and y=0.141.

Embodiment 4 Using Compound with Structure of Chemical Formula 6

An organic light emitting device fabricated according to Embodiment 4 was as same as that in Embodiment 1 excluding that 5% of BD-58 of Chemical Formula 7 was added as a dopant to the host.

For the organic light emitting device in this structure, upon applying a current of 0.9 mA, brightness ($cd/m^2$) was 572 $cd/m^2$, a driving voltage (V) was 4.63V, color coordinates (CIE) were x=0.151 and y=0.148.

Embodiment 5 Using Compound with Structure of Chemical Formula 6

An organic light emitting device fabricated according to Embodiment 5 was as same as that in Embodiment 1 excluding that 5% of BD-66 of Chemical Formula 7 was added as a dopant to the host material.

For the organic light emitting device in this structure, upon applying a current of 0.9 mA, brightness ($cd/m^2$) was 594 $cd/m^2$, a driving voltage (V) was 4.67V, color coordinates (CIE) were x=0.151 and y=0.149.

Embodiment 6 Using Compound with Structure of Chemical Formula 6

An organic light emitting device fabricated according to Embodiment 6 was as same as that in Embodiment 1 excluding that 5% of BD-68 of Chemical Formula 7 was added as a dopant to the host material.

For the organic light emitting device in this structure, upon applying a current of 0.9 mA, brightness (cd/m$^2$) was 512 cd/m$^2$, a driving voltage (V) was 4.92V, color coordinates (CIE) were x=0.147 and y=0.158.

Embodiment 7 Using Compound with Structure of Chemical Formula 6

An organic light emitting device fabricated according to Embodiment 7 was as same as that in Embodiment 1 excluding that 5% of BD-85 of Chemical Formula 7 was added as a dopant to the host material.

For the organic light emitting device in this structure, upon applying a current of 0.9 mA, brightness (cd/m$^2$) was 623 cd/m$^2$, a driving voltage (V) was 4.41V, color coordinates (CIE) were x=0.147 and y=0.148.

Embodiment 8 Using Compound with Structure of Chemical Formula 6

An organic light emitting device fabricated according to Embodiment 8 was as same as that in Embodiment 1 excluding that 5% of BD-128 of Chemical Formula 7 was added as a dopant to the host material.

For the organic light emitting device in this structure, upon applying a current of 0.9 mA, brightness (cd/m$^2$) was 583 cd/m$^2$, a driving voltage (V) was 4.40V, color coordinates (CIE) were x=0.147 and y=0.150.

Embodiment 9 Using Compound with Structure of Chemical Formula 6

An organic light emitting device fabricated according to Embodiment 9 was as same as that in Embodiment 1 excluding that 5% of BD-173 of Chemical Formula 7 was added as a dopant to the host material.

For the organic light emitting device in this structure, upon applying a current of 0.9 mA, brightness (cd/m$^2$) was 526 cd/m$^2$, a driving voltage (V) was 4.41V, color coordinates (CIE) were x=0.144 and y=0.147.

Comparison Example

An organic light emitting device fabricated according to Comparison Example was as same as that in Embodiment 1 excluding that 1% of the dopant with the structure of Chemical Formula 1 was added to the host material.

For the related art organic light emitting device in this structure, upon applying a current of 0.9 mA, brightness (cd/m$^2$) was 576 cd/m$^2$, a driving voltage (V) was 6.7V, color coordinates (CIE) were x=0.136 and y=0.188.

Device measurement results of the organic light emitting devices fabricated according to Embodiments 1 to 9 and the organic light emitting device fabricated according to Comparison Example were shown in Table 1.

TABLE 1

| Device | Current (mA) | Voltage (V) | Brightness (cd/m2) | CIE (X) | CIE (Y) |
|---|---|---|---|---|---|
| Embodiment 1 | 0.9 | 4.36 | 616 | 0.145 | 0.143 |
| Embodiment 2 | 0.9 | 4.38 | 482 | 0.146 | 0.141 |
| Embodiment 3 | 0.9 | 4.54 | 585 | 0.146 | 0.141 |
| Embodiment 4 | 0.9 | 4.63 | 572 | 0.151 | 0.148 |
| Embodiment 5 | 0.9 | 4.67 | 594 | 0.151 | 0.149 |
| Embodiment 6 | 0.9 | 4.92 | 512 | 0.147 | 0.158 |
| Embodiment 7 | 0.9 | 4.41 | 623 | 0.147 | 0.148 |

TABLE 1-continued

| Device | Current (mA) | Voltage (V) | Brightness (cd/m2) | CIE (X) | CIE (Y) |
|---|---|---|---|---|---|
| Embodiment 8 | 0.9 | 4.40 | 583 | 0.147 | 0.150 |
| Embodiment 9 | 0.9 | 4.41 | 576 | 0.144 | 0.147 |
| Comparison Example | 0.9 | 6.70 | 526 | 0.136 | 0.188 |

As shown in Table 1, it can be noticed that by forming the organic light emitting layer by adding the dopant defined by Chemical Formula 7, the brightness and color purity of the organic light emitting device according to the present invention are enhanced and the driving voltage thereof is lowered (by about 1.5-2.5V), compared to the related art organic light emitting device. That is, it can be exhibited excluding the organic light emitting devices fabricated according to Embodiments 2 and 6 that the brightness was increased and the driving voltage was lowered, compared to the related art organic light emitting device. Also, as shown in Table 1, the color coordinates were changed from x=0.136 and y=0.188 to x=0.144-0.151 and y=0.141-0.158, which indicated enhancement of color purity.

Hereinafter, Synthesis Example and Embodiments of a material in the structure defined by Chemical Formula 8 will be described.

Synthesis Example and Embodiments of Compound of Chemical Formula 8

Synthesis Example 3

Fabrication of BD'-11 of Chemical Formula 9

(1) Synthesis of 1-phenylpyrene

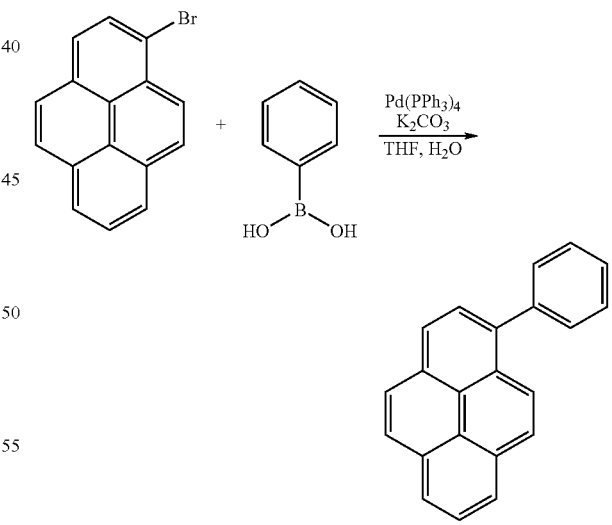

1-bromopyrene (2 g, 7.11 mmol) and phenylboronic acid (1.40 g, 14.30 mmol) were put into a 2-neck round bottom flask filled with 80 ml of anhydrous tetrahydrofuran and stirred. Tetrakis(triphenylphosphine) palladium (0.41 g, 5 mol %), 20 g of potassium carbonate and 80 ml of distilled water were added into the same flask, which was then subjected to reflux at a temperature of 100° C. for 24 hours. After completion of the reaction, the tetrahydrofuran was removed and thusly generated solid was filtered. The filtered solid was recrystallized by dichloromethane and ethanol, thereby synthesizing 1-phenylpyrene (1.84 g, 93%).

(2) Fabrication of 1-phenyl-3,6,8-tribromopyrene

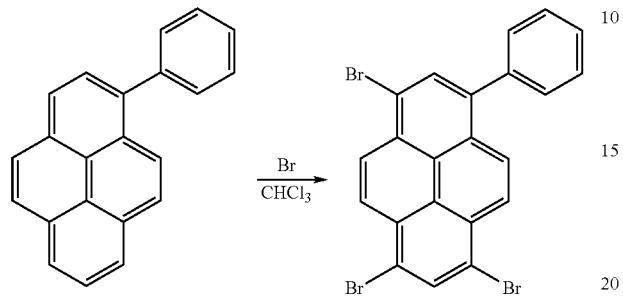

1-phenylpyrene (2 g, 7.19 mmol) and 50 ml of chloroform were put into a 2-neck round bottom flask and stirred. Bromine (4.02 g, 25.17 mmol) was slowly dropped into the flask for 30 minutes and then refluxed at a temperature of 70° C. for 8 hours. After lowering the temperature down to room temperature, 100 ml of distilled water was poured into the refluxed mixture and then stirred. After filtering off a generated solid, the filtered solid was washed with 50 ml of distilled water and 50 ml of ethanol, thereby fabricating 1-phenyl-3,6,8-tribromopyrene (2.96 g, 80%).

(3) Fabrication of 1-phenyl-3,6,8-triphenylpyrene BD'-11

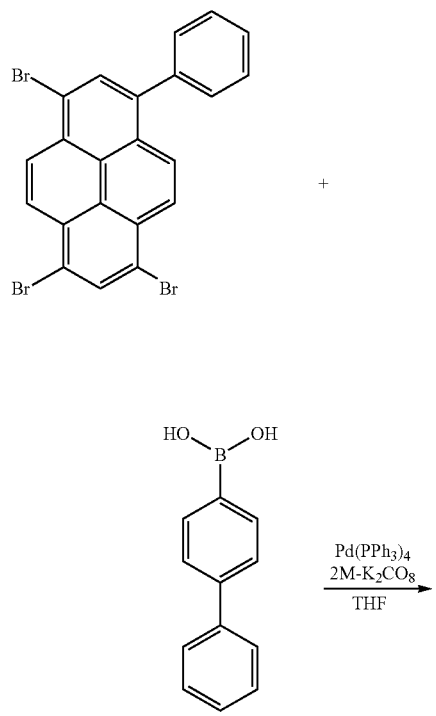

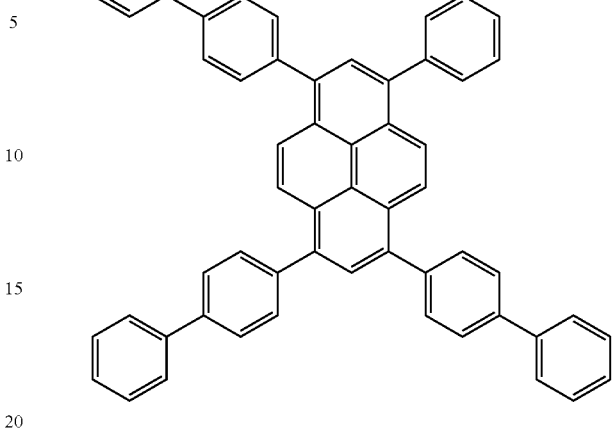

1-phenyl-3,6,8-tribromopyrene (2 g, 3.88 mmol), 4-biphenylboronic acid (2.34 g, 11.83 mmol) and 80 ml of anhydrous tetrahydrofuran were put into a 2-neck round bottom flask and stirred. Tetrakis(triphenylphosphine) palladium (0.22 g, 5 mol %), 20 g of potassium carbonate and 80 ml of distilled water were added into the same flask, which was then subjected to reflux at a temperature of 100° C. for 24 hours. After completion of the reaction, the tetrahydrofuran was removed and thusly generated solid was filtered. The filtered solid was recrystallized by dichloromethane and ethanol, thereby synthesizing 1-phenyl-3,6,8-triphenylpyrene (2.37 g, 83%).

An organic light emitting device using the compound in the structure of Chemical Formula 8 and a fabrication method thereof will now be described. The organic light emitting devices fabricated according to the following embodiments has the structure shown in FIG. 1.

Embodiment 10 Using Compound with Structure of Chemical Formula 8

ITO was patterned on a substrate in a size of 3×3 mm and washed. The washed substrate was attached onto a vacuum chamber and thereafter the vacuum chamber was made to be in a vacuum state with a 1×10-ton basal pressure. Afterwards, 200 Å of organic light emitting materials, 350 Å of Alq$_3$, 5 Å of LiF and 1000 Å of Al were sequentially deposited on the ITO, wherein the organic light emitting material has 5% of BD-1 of Chemical Formula 9 as a dopant added to its host material composed of CuPC (200 Å), NPD (400 Å) and DPVBi, thereby sequentially forming, on an anode, a hole inject layer, a hole transport layer, an organic light emitting layer, an electron transport layer and a cathode.

For the organic light emitting device in this structure, upon applying a current of 0.9 mA, brightness (cd/m$^2$) was 621 cd/m$^2$, a driving voltage (V) was 4.42V, color coordinates (CIE) were x=0.146 and y=0.143.

Embodiment 11 Using Compound with Structure of Chemical Formula 8

An organic light emitting device fabricated according to Embodiment 11 was as same as that in Embodiment 10 excluding that 5% of BD'-34 of Chemical Formula 9 was added as a dopant to the host material For the organic light emitting device in this structure, upon applying a current of 0.9 mA, brightness (cd/m$^2$) was 625 cd/m², a driving voltage (V) was 4.43V, color coordinates (CIE) were x=0.141 and y=0.156.

Embodiment 12 Using Compound with Structure of Chemical Formula 8

An organic light emitting device fabricated according to Embodiment 12 was as same as that in Embodiment 10 excluding that 5% of BD'-75 of Chemical Formula 9 was added as a dopant to the host material.

For the organic light emitting device in this structure, upon applying a current of 0.9 mA, brightness (cd/m²) was 512 cd/m², a driving voltage (V) was 5.20V, color coordinates (CIE) were x=0.148 and y=0.156.

Embodiment 13 Using Compound with Structure of Chemical Formula 8

An organic light emitting device fabricated according to Embodiment 13 was as same as that in Embodiment 10 excluding that 5% of BD'-94 of Chemical Formula 9 was added as a dopant to the host material.

For the organic light emitting device in this structure, upon applying a current of 0.9 mA, brightness (cd/m²) was 675 cd/m², a driving voltage (V) was 4.75V, color coordinates (CIE) were x=0.144 and y=0.161.

Device measurement results of the organic light emitting devices fabricated according to Embodiments 10 to 13 and the organic light emitting device fabricated according to Comparison Example were shown in Table 2.

TABLE 2

| Device | Current (mA) | Voltage (V) | Brightness (cd/m2) | CIE (X) | CIE (Y) |
|---|---|---|---|---|---|
| Embodiment 10 | 0.9 | 4.42 | 621 | 0.146 | 0.143 |
| Embodiment 11 | 0.9 | 4.43 | 625 | 0.141 | 0.156 |
| Embodiment 12 | 0.9 | 5.20 | 512 | 0.148 | 0.156 |
| Embodiment 13 | 0.9 | 4.75 | 675 | 0.144 | 0.161 |
| Comparison Example | 0.9 | 6.7 | 526 | 0.136 | 0.188 |

As shown in Table 2, it can be noticed that by forming the organic light emitting layer by adding the dopant defined by Chemical Formula 9, the brightness and color purity of the organic light emitting device according to the present invention are enhanced and the driving voltage thereof is lowered (by about 1.5-2.5V), compared to the related art organic light emitting device. That is, it can be exhibited excluding the organic light emitting devices fabricated according to Embodiment 12 that the brightness was increased and the driving voltage was lowered, compared to the related art organic light emitting device. Also, as shown in Table 2, the color coordinates were changed from x=0.136 and y=0.188 to x=0.144-0.151 and y=0.141-0.158, which indicated enhancement of color purity.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An organic light emitting material having the following chemical formula,

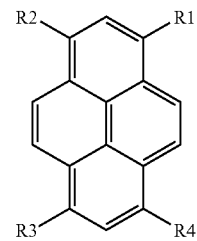

where R1=R3, R2=R4, and R1≠R2, each of R1 and R3 is phenyl substituted with at least one selected from the group consisting of trimethylsilane (TMS), CN, halogen, alkyl group with 1 to 4 carbon atoms (C1-C4) and Phenyl and each of R2 and R4 is anthracene or phenanthrene, each of which is independently substituted or un-substituted.

2. An organic light emitting material having a compound selected from one of the following compounds,

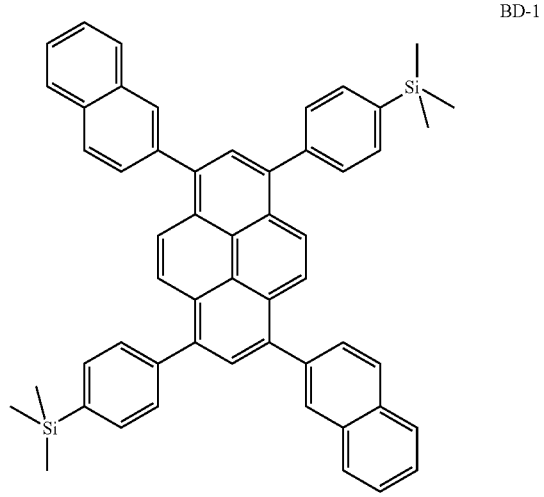

BD-1

BD-2
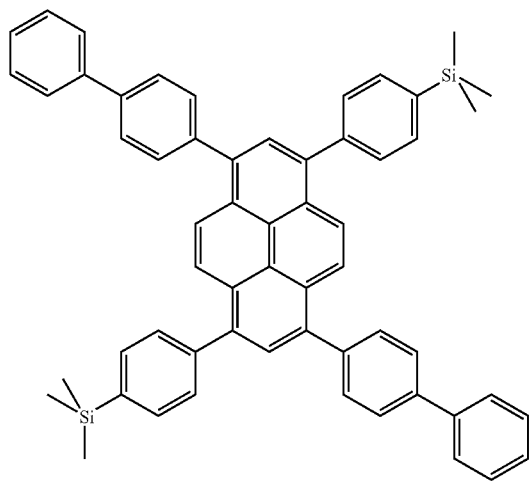
BD-3
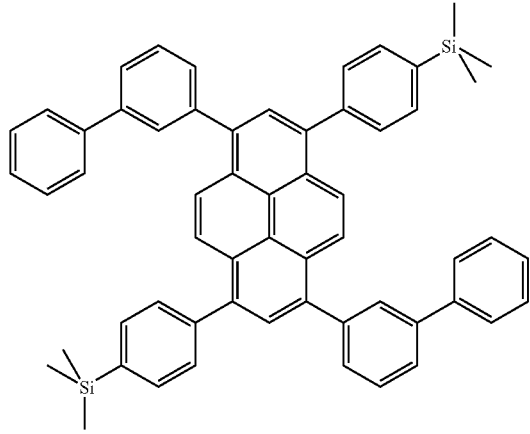
BD-4
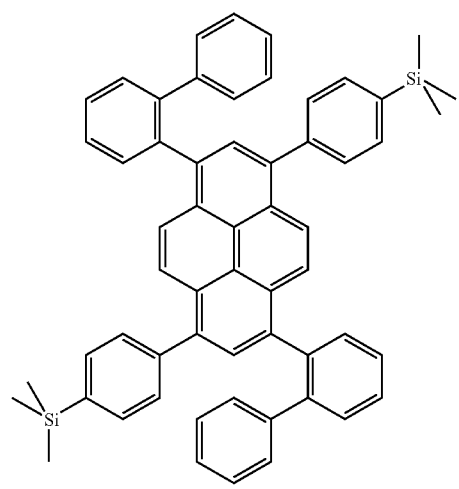
BD-5
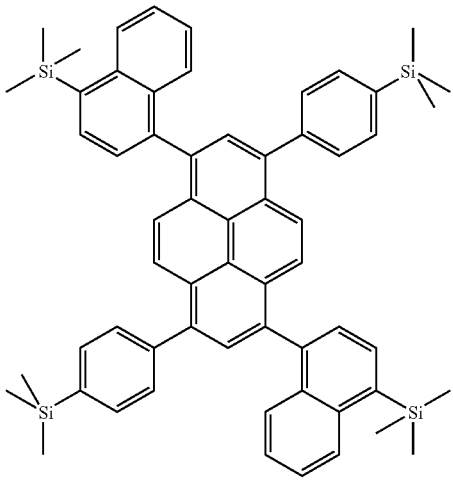
BD-6
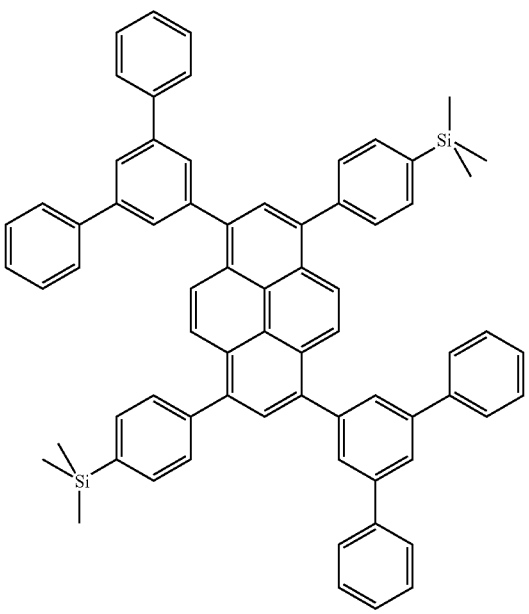
BD-7
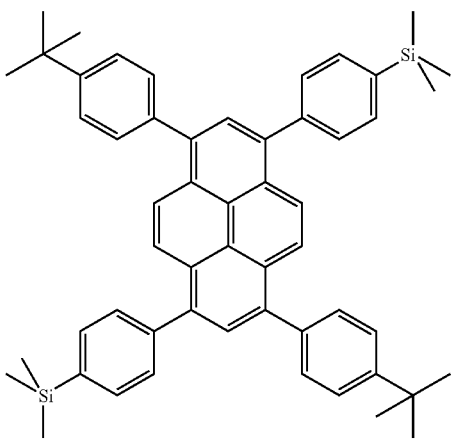

BD-8
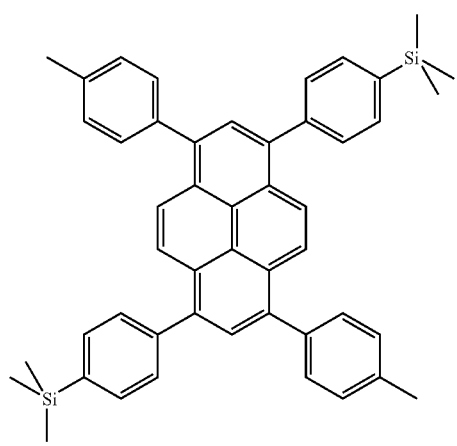
BD-9
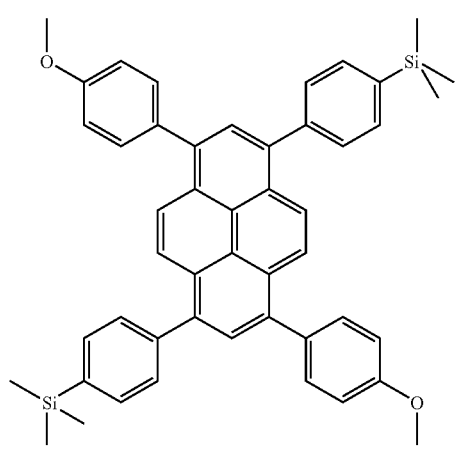
BD-10
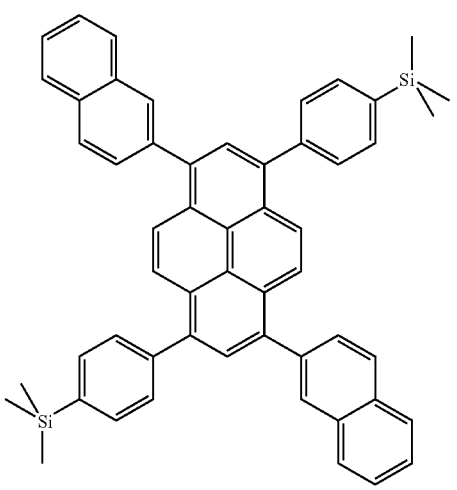
BD-11
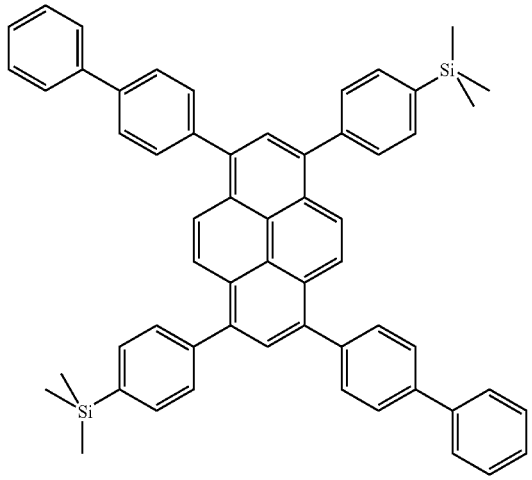
BD-12
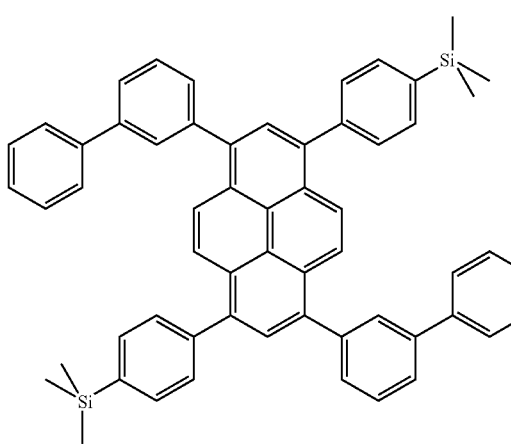
BD-13
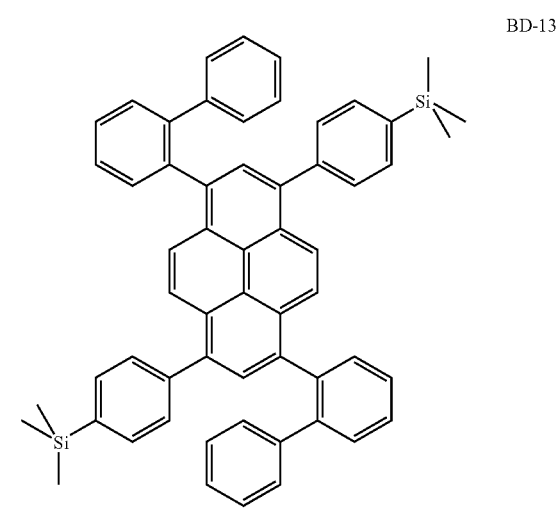

BD-14
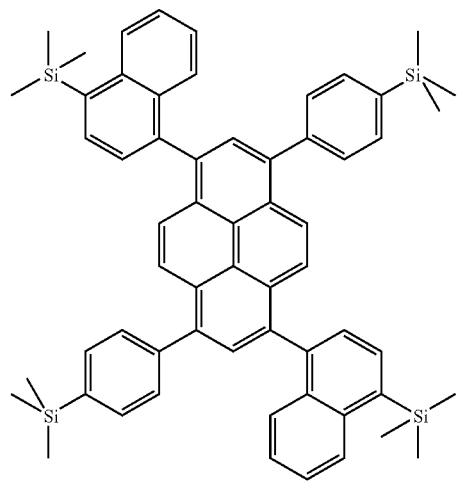
BD-15
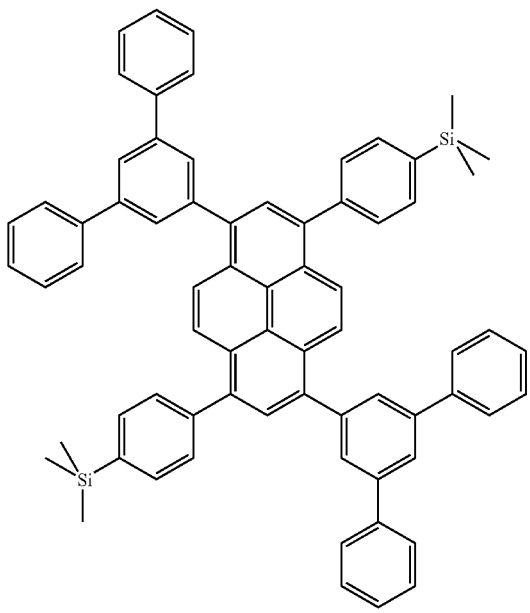
BD-16
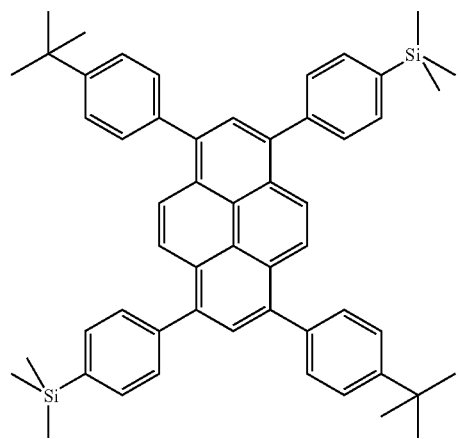
BD-17
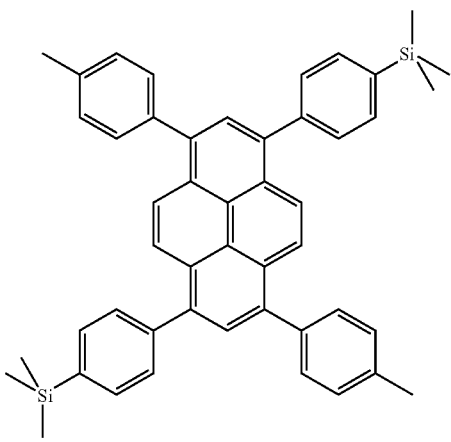
BD-18
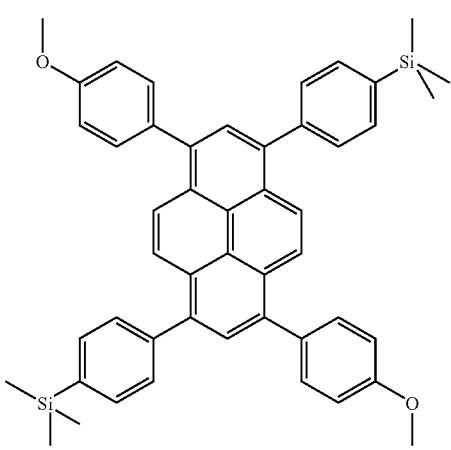
BD-19
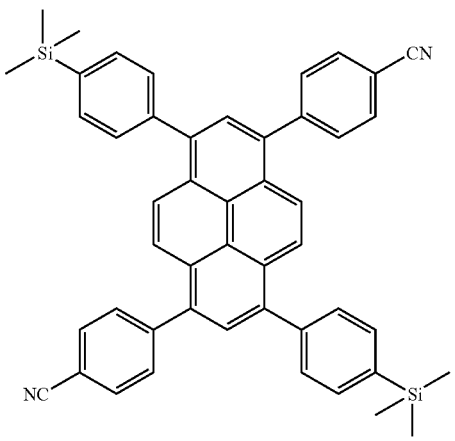

BD-20
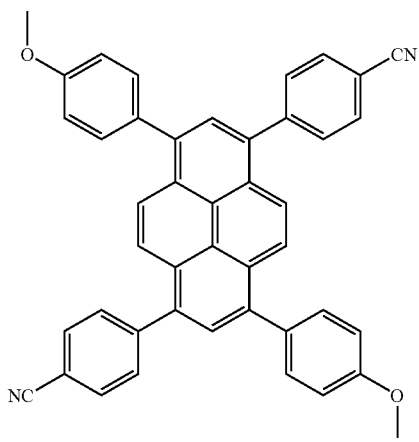
BD-21
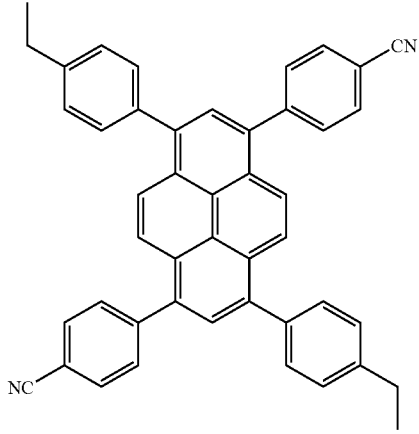
BD-22
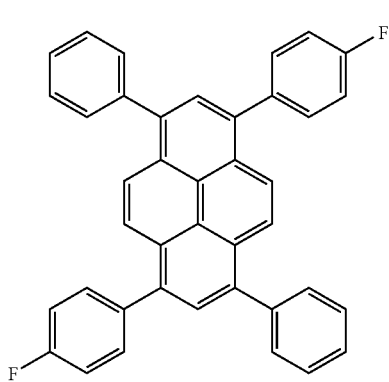
BD-23
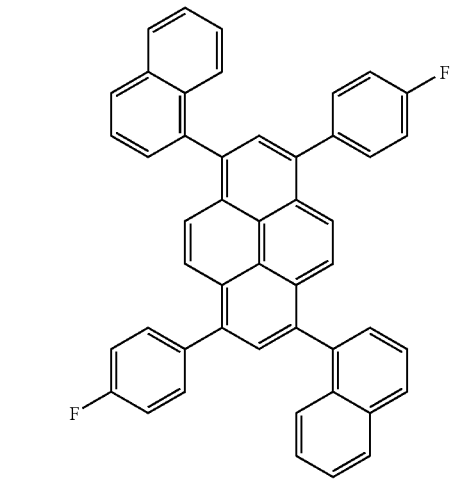
BD-24
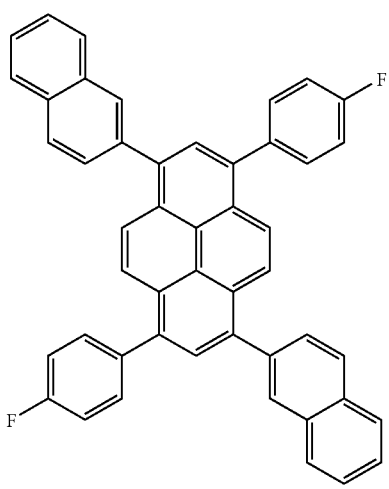
BD-25
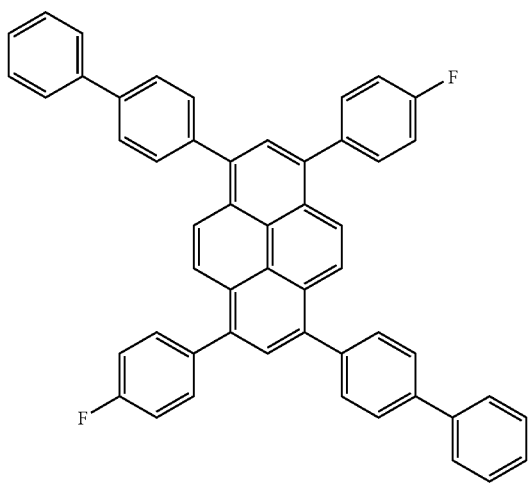

-continued
BD-26
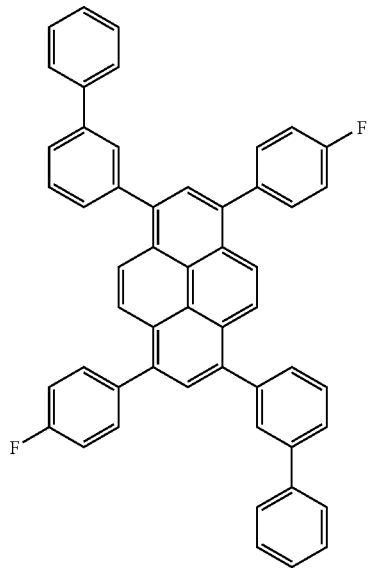
BD-27
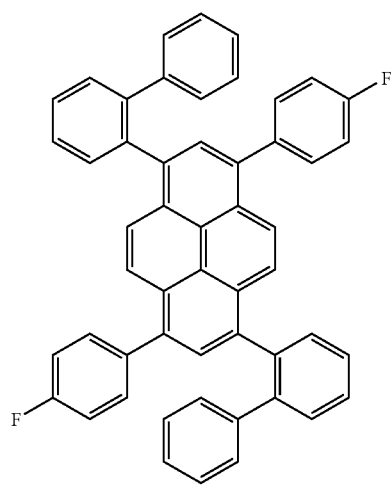
BD-28
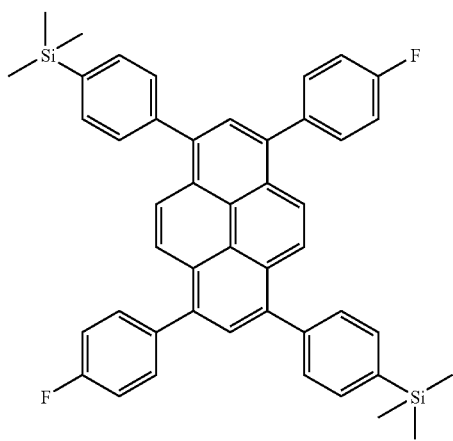
-continued
BD-29
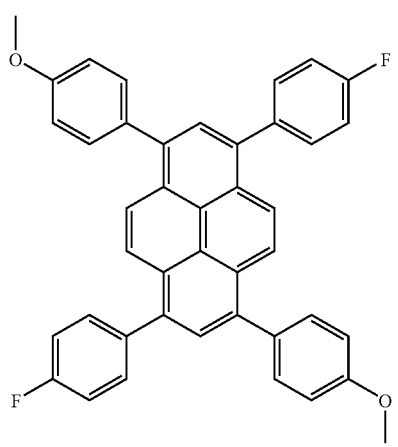
BD-30
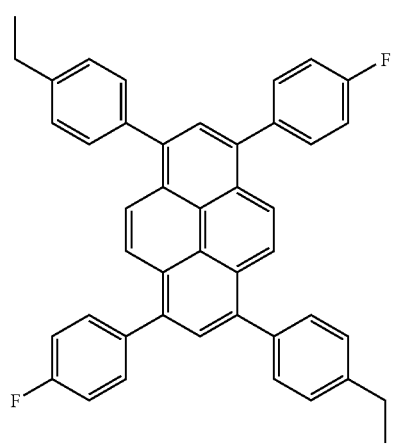
BD-31
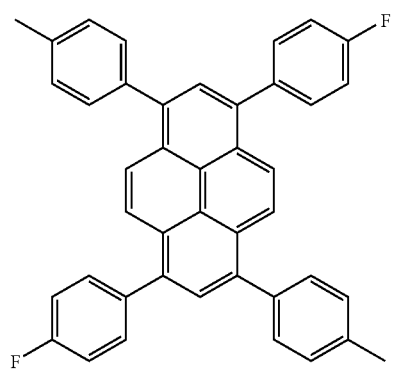

BD-32
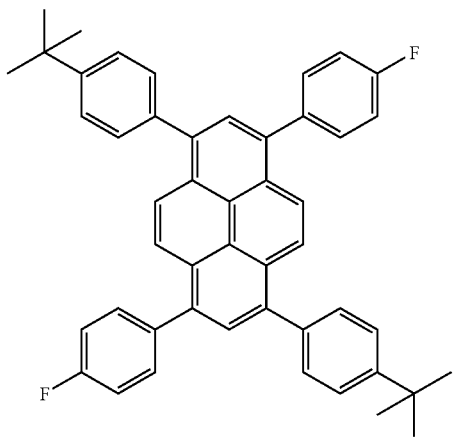
BD-35
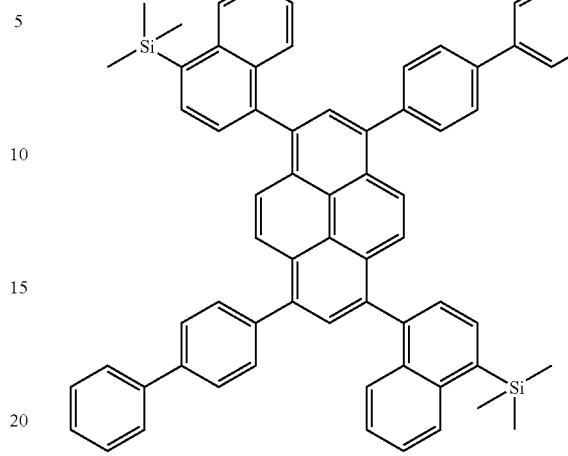
BD-33
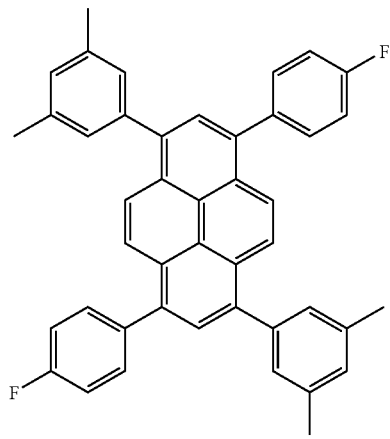
BD-36
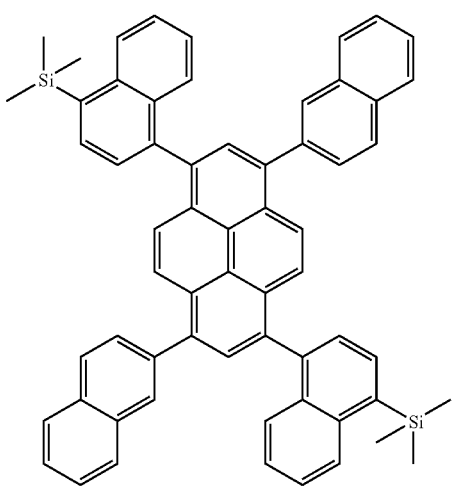
BD-34
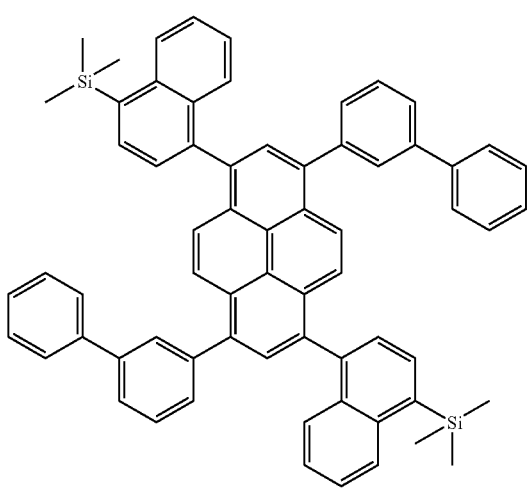
BD-37
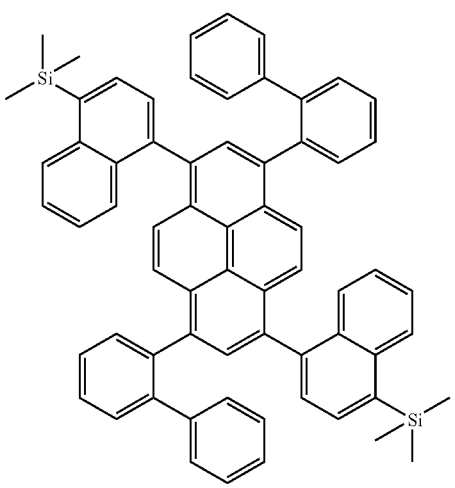

-continued
BD-38
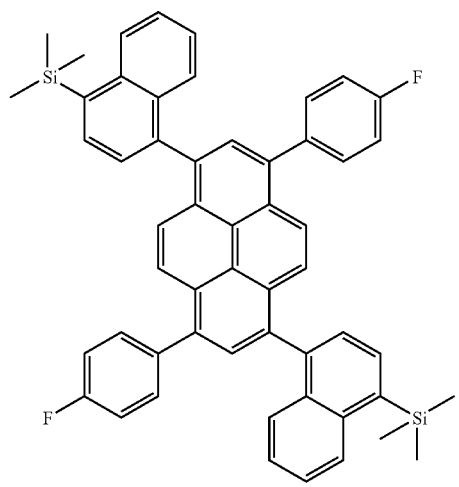
BD-41
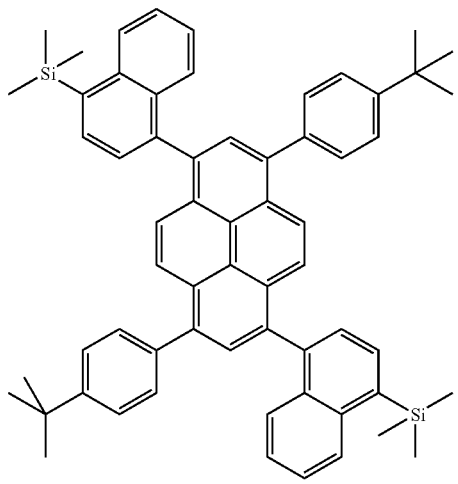
BD-39
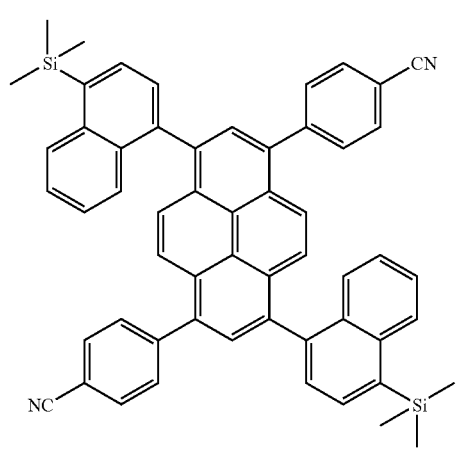
BD-42
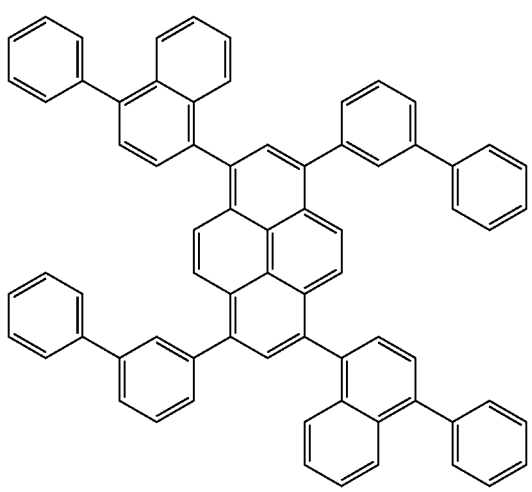
BD-40
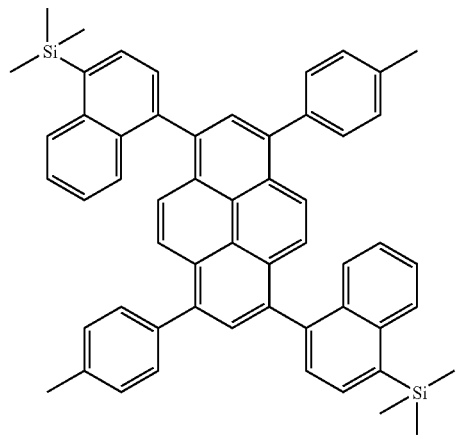
BD-43

BD-44
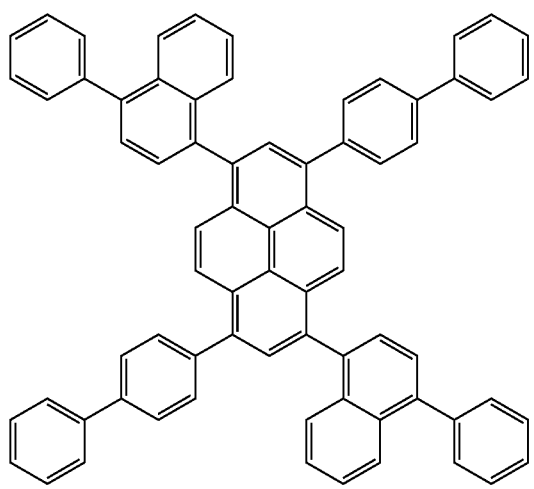
BD-47
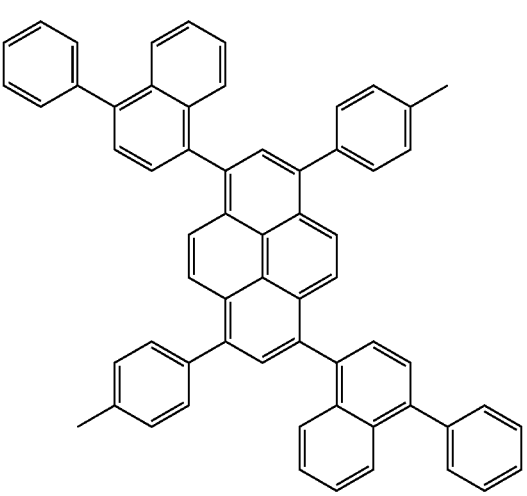
BD-45
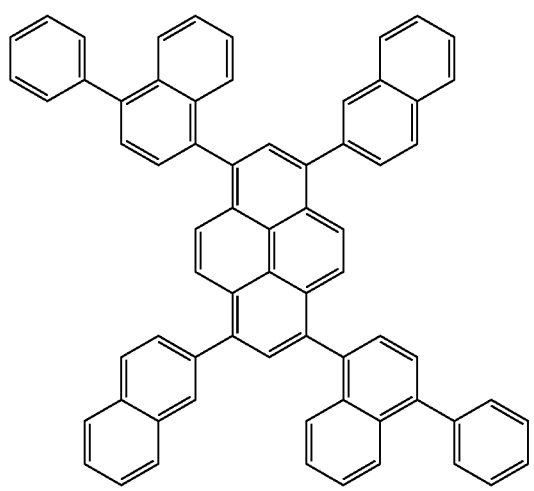
BD-48
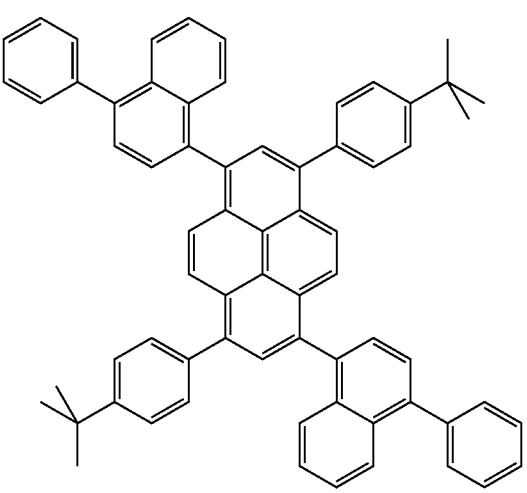
BD-46
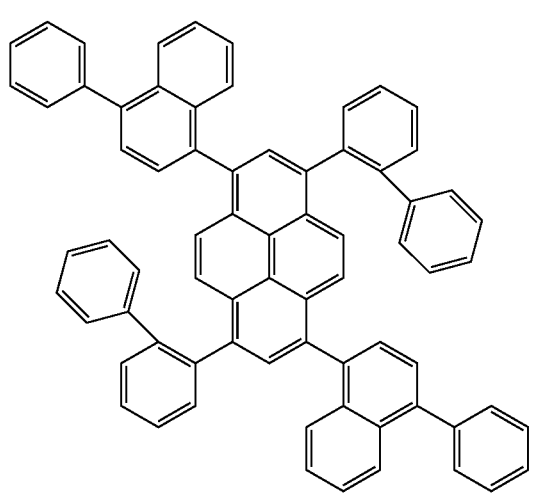
BD-49
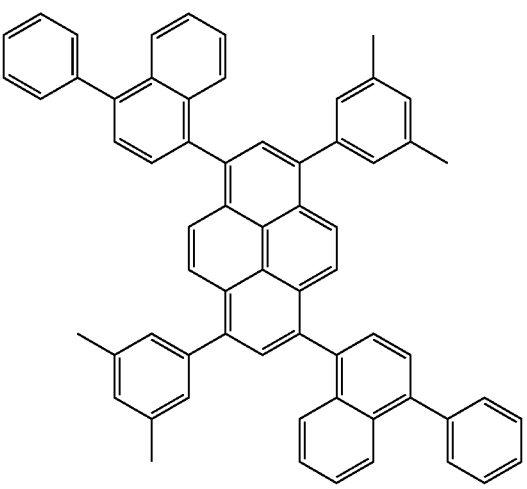

BD-50
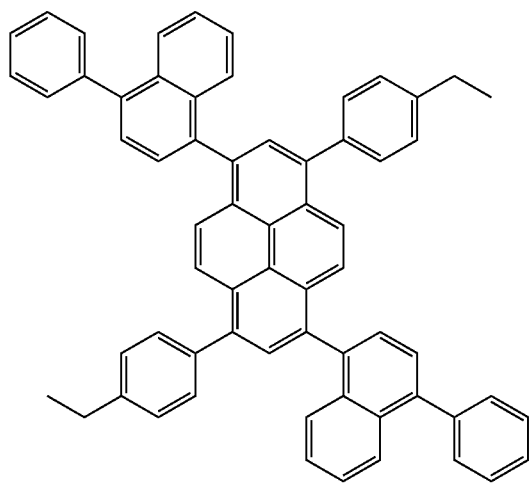
BD-53
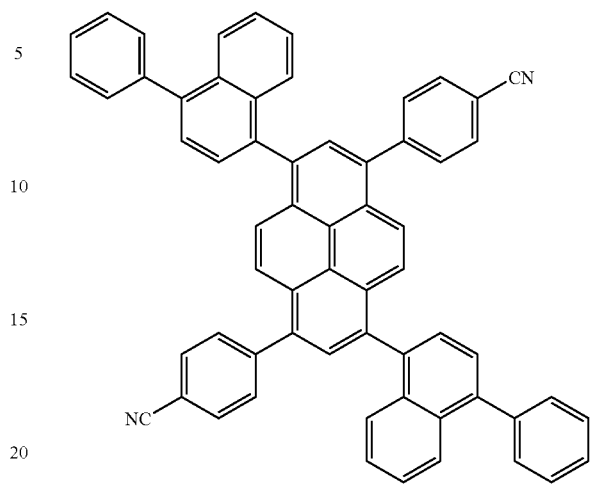
BD-51
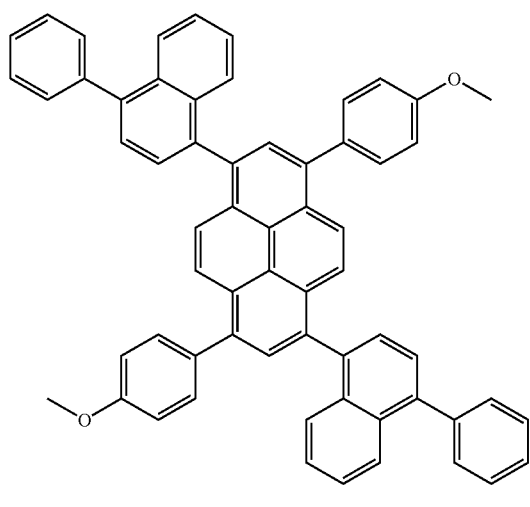
BD-54
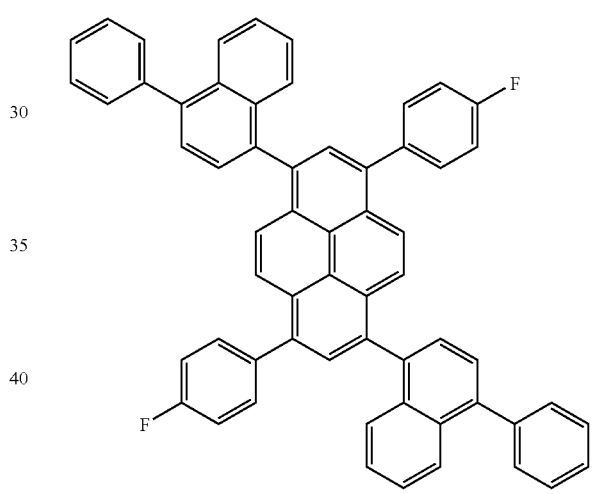
BD-52
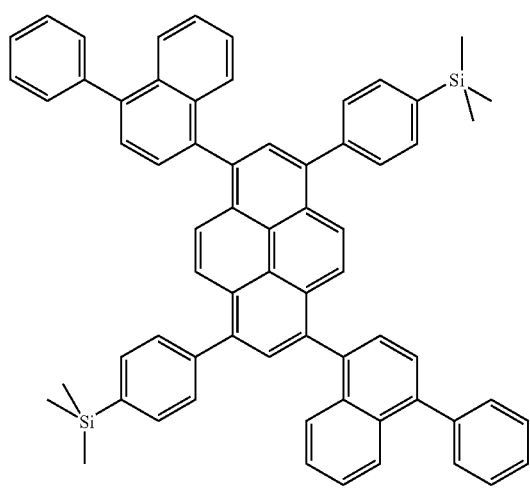
BD-55
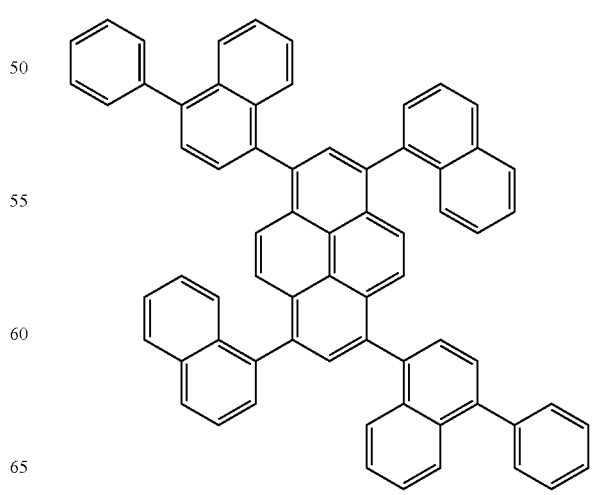

-continued
BD-56
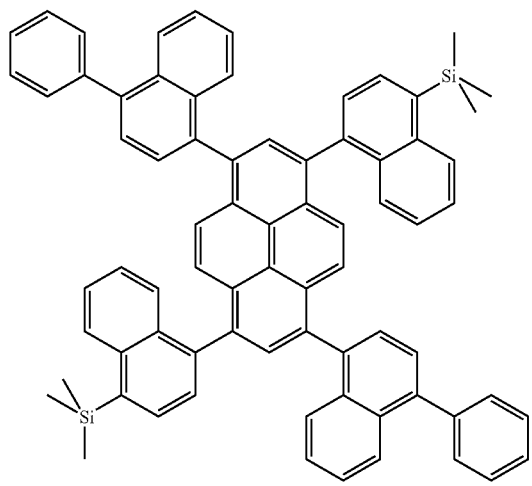
BD-59
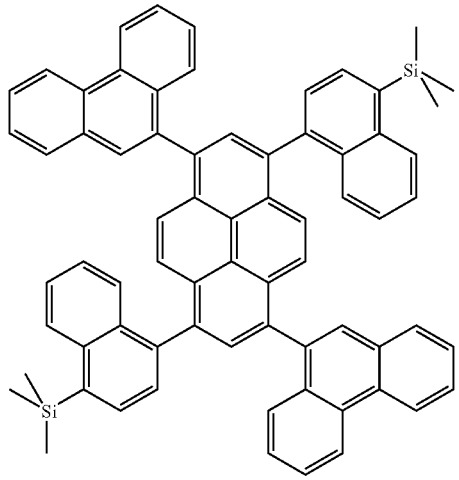
BD-57
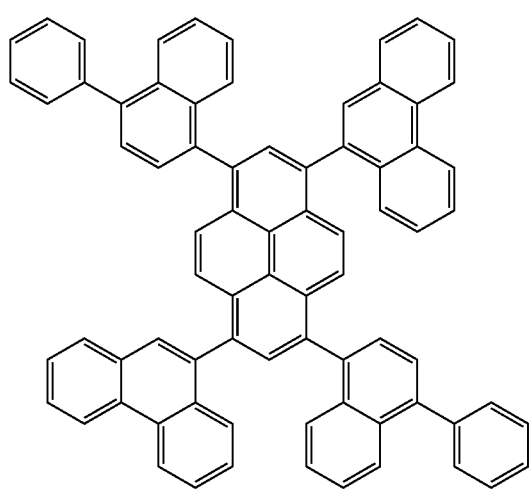
BD-60
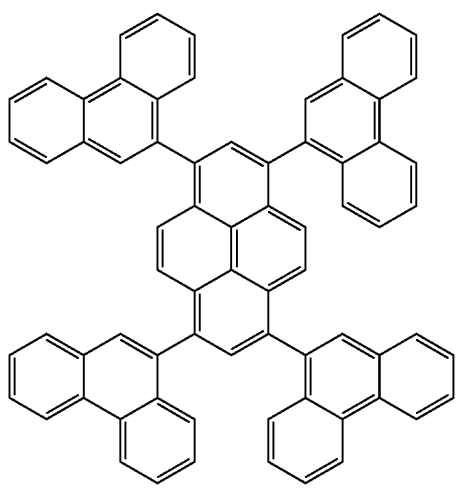
BD-58
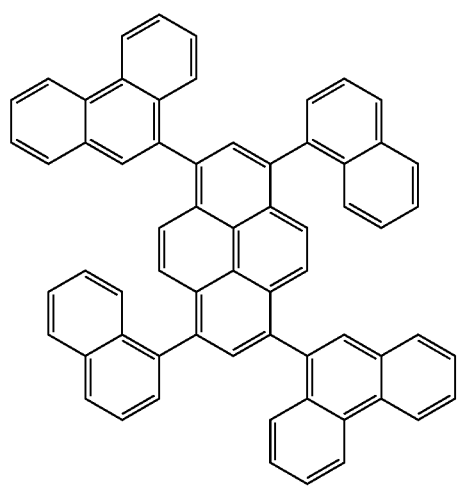
BD-61
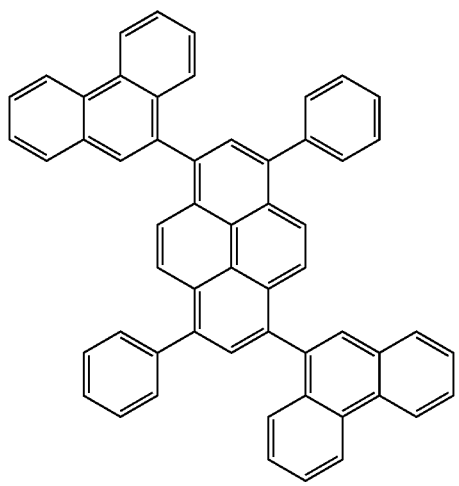

-continued
BD-62
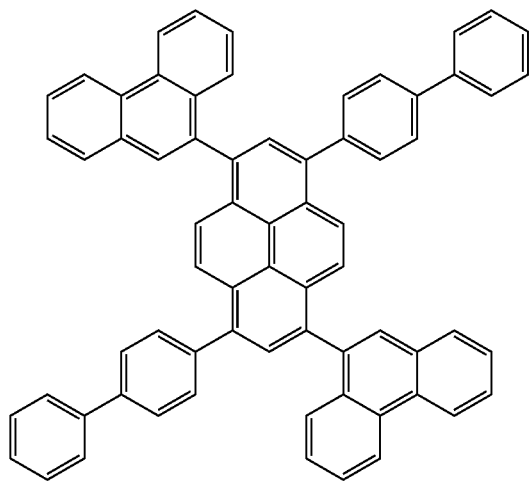
BD-63
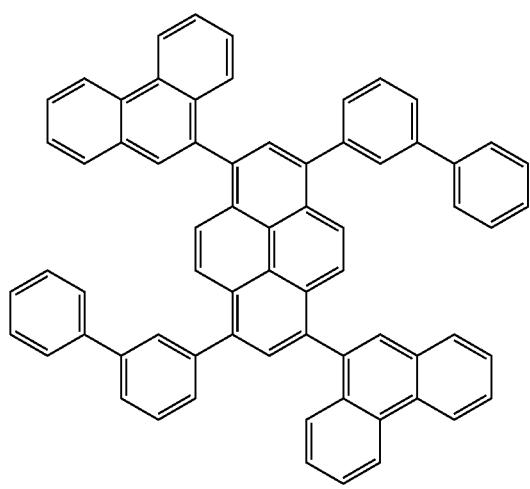
BD-64
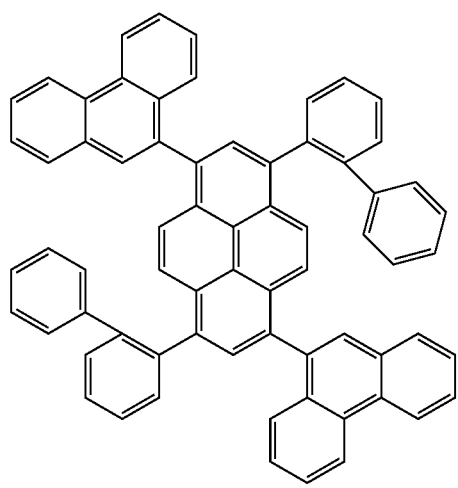
-continued
BD-65
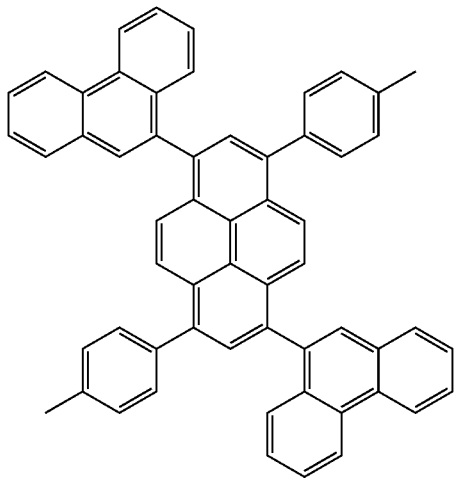
BD-66
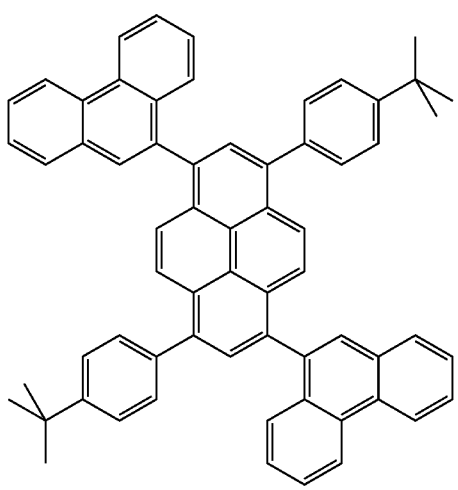
BD-67
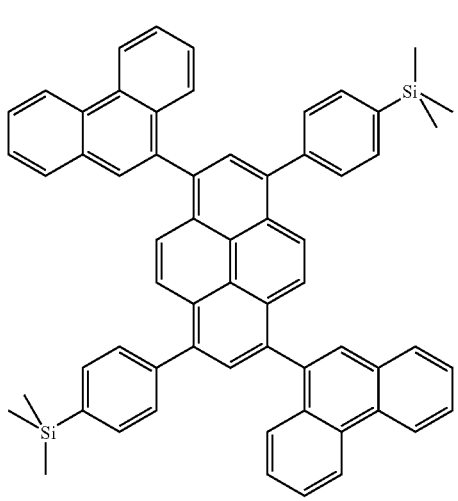

BD-68
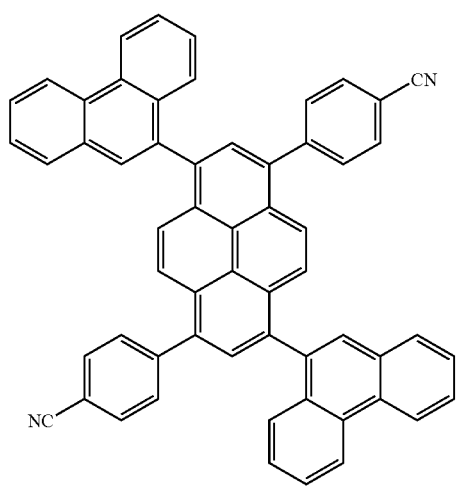
BD-71
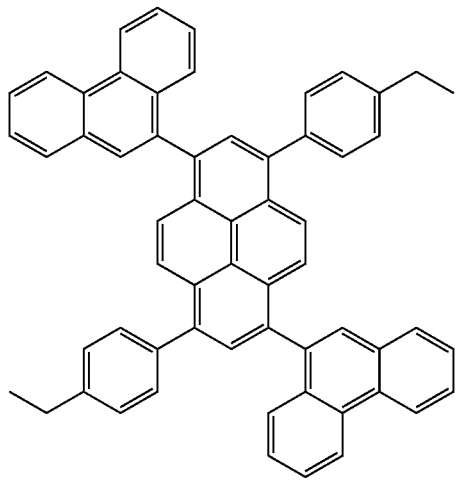
BD-69
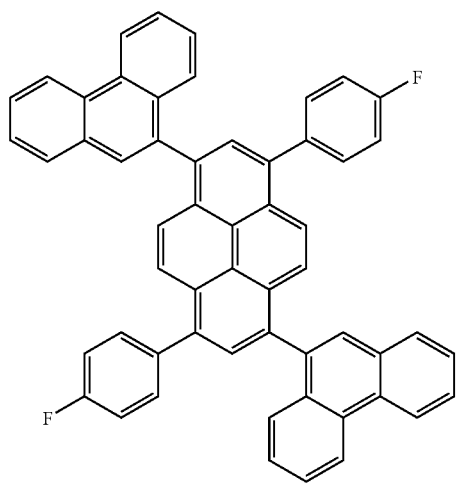
BD-72
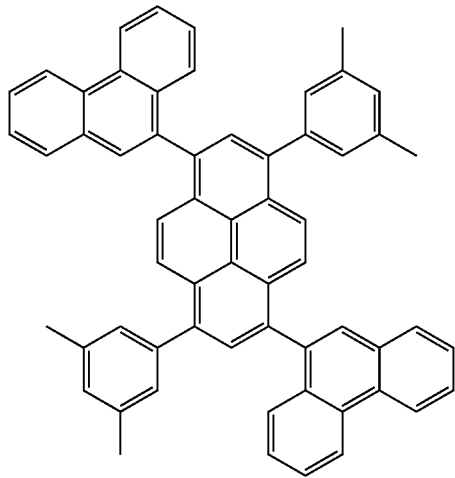
BD-70
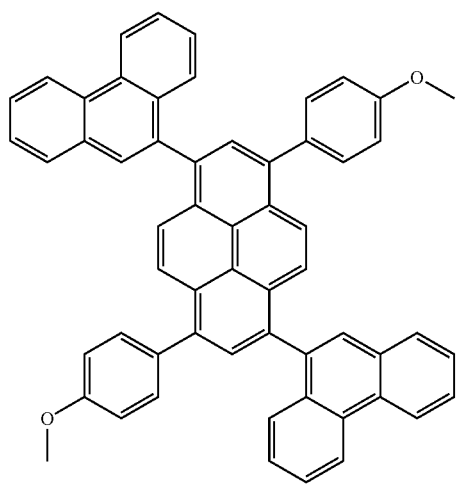
BD-73
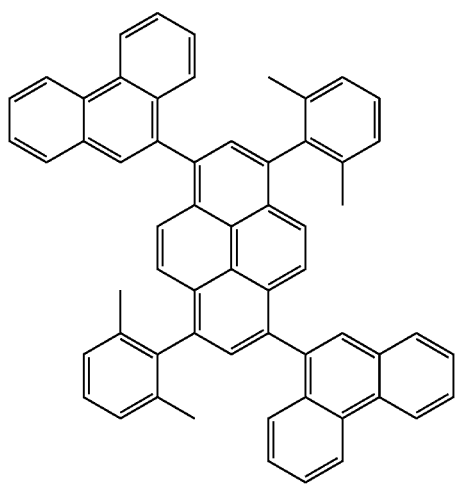

BD-74
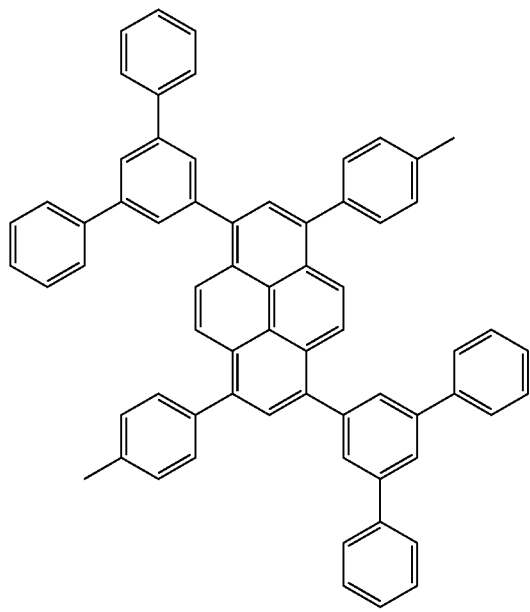
BD-76
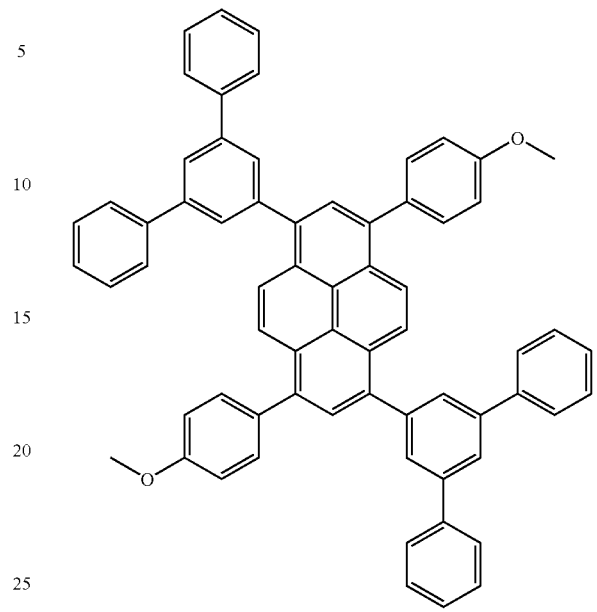
BD-75
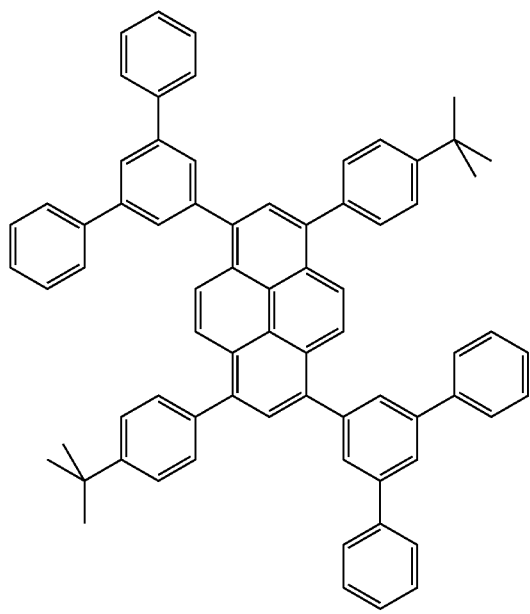
BD-77
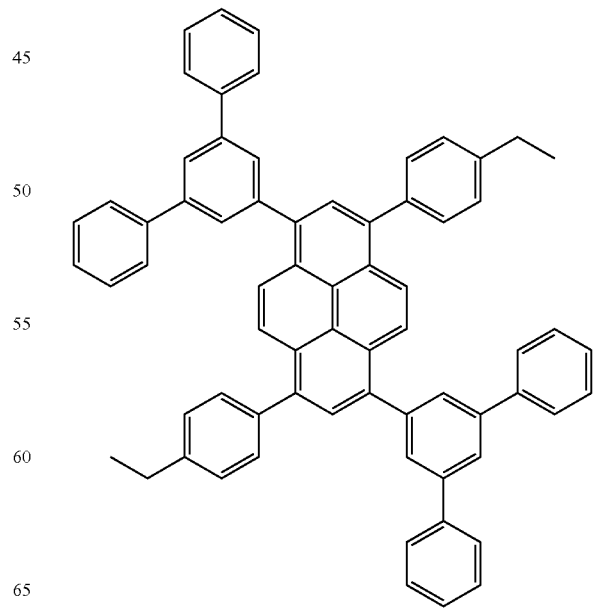

BD-78
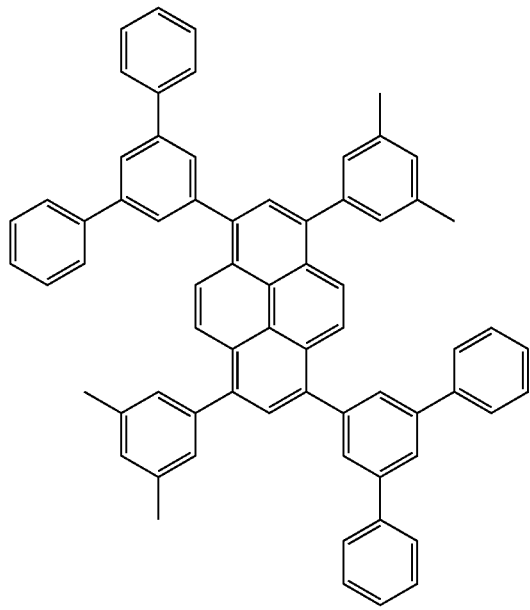
BD-80
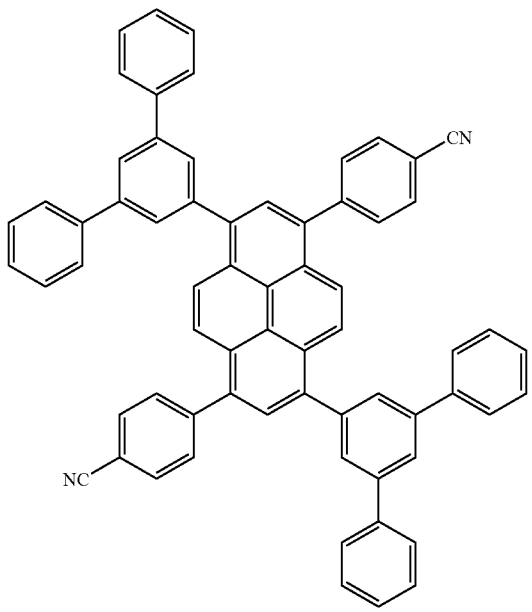
BD-79
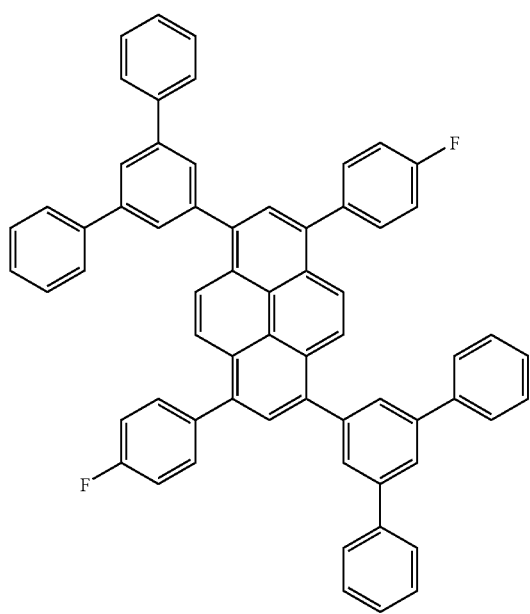
BD-81
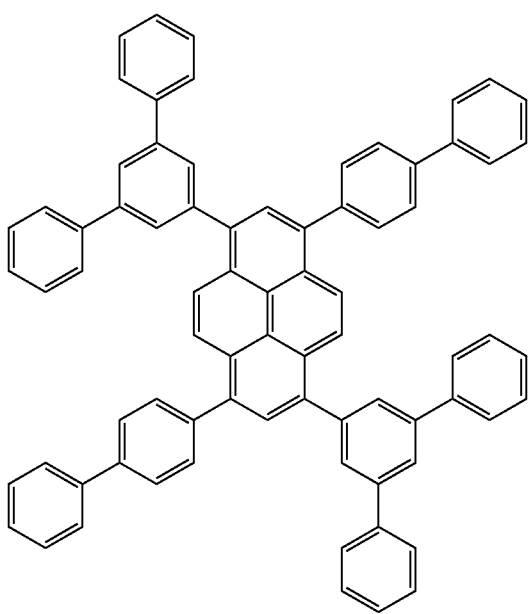

BD-82
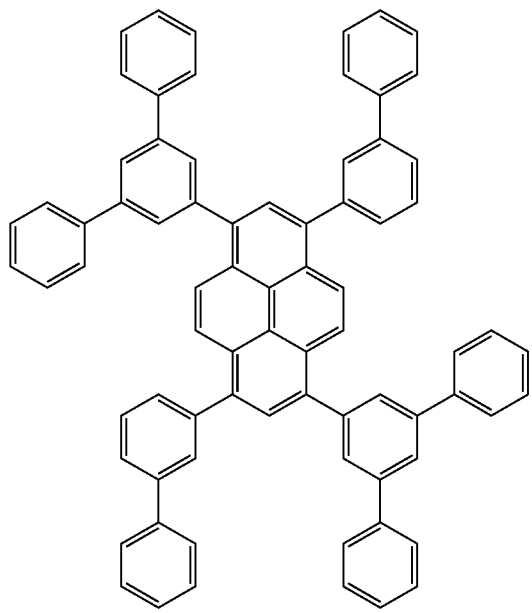
BD-84
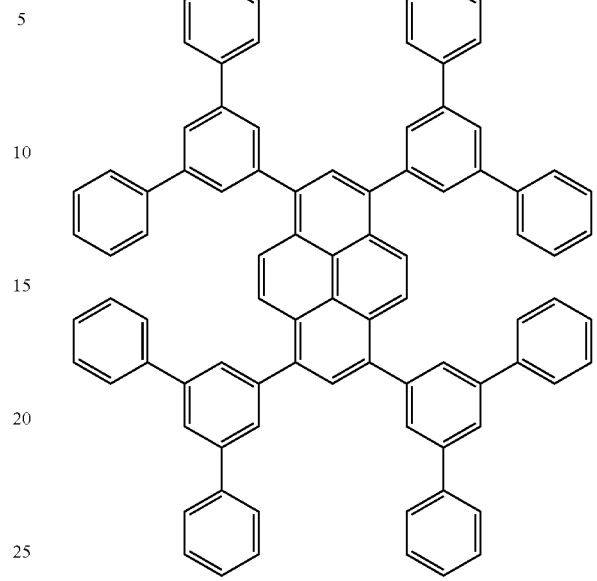
BD-83
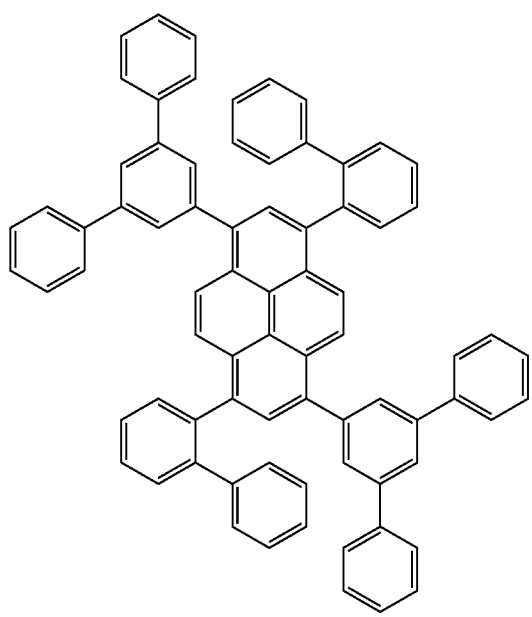
BD-85
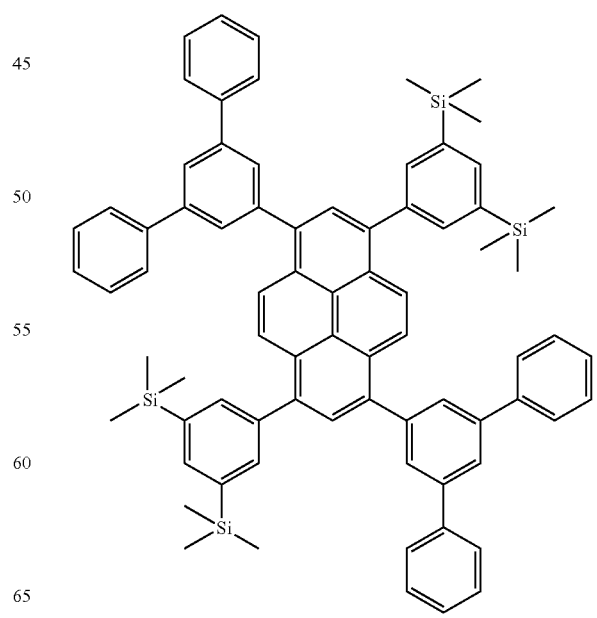

-continued
BD-86
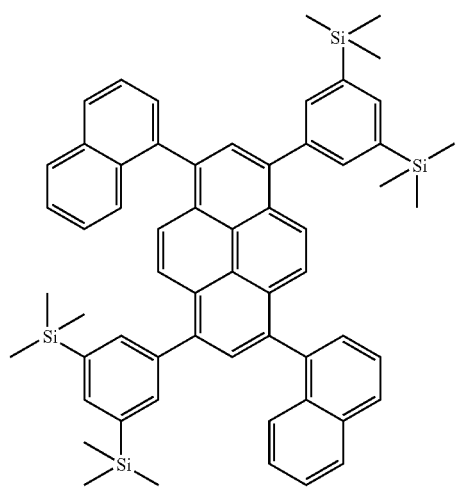
BD-85
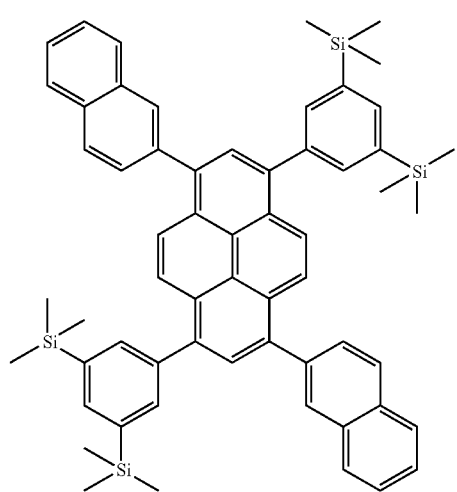
BD-86
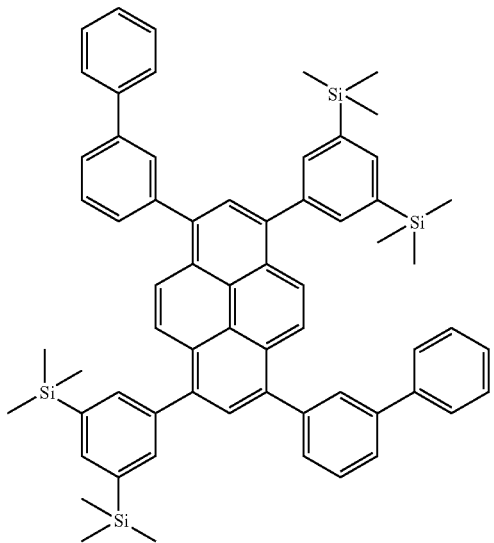
-continued
BD-87
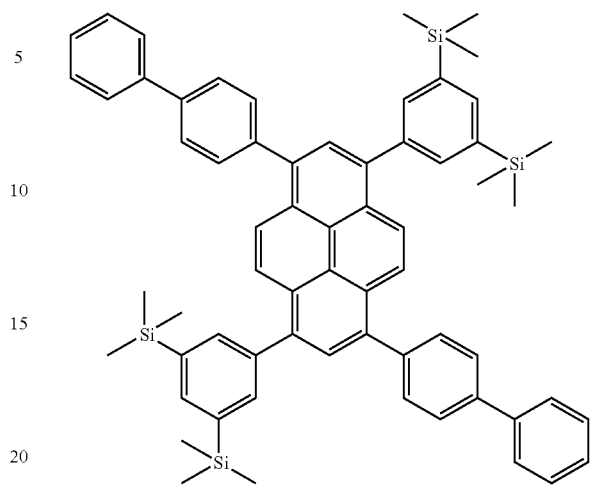
BD-88
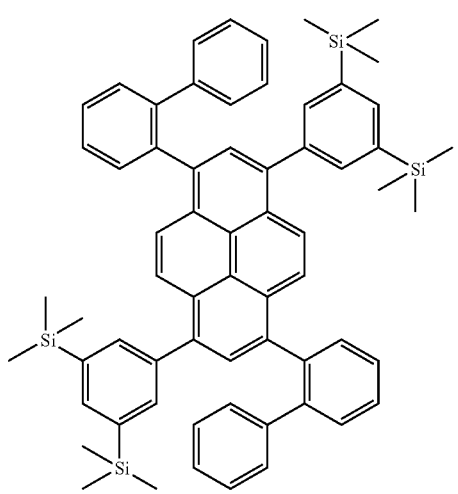
BD-89
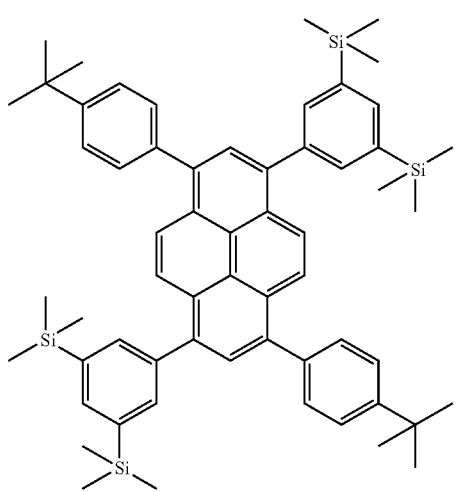

BD-90
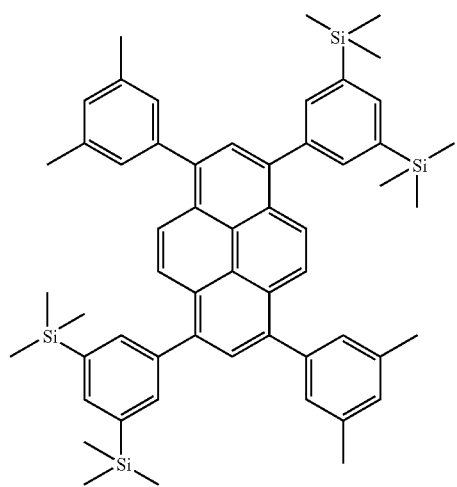
BD-91
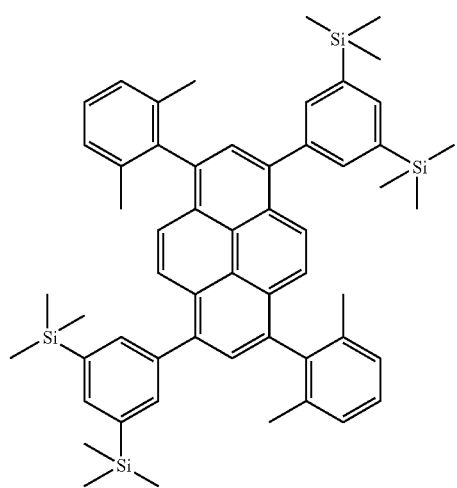
BD-92
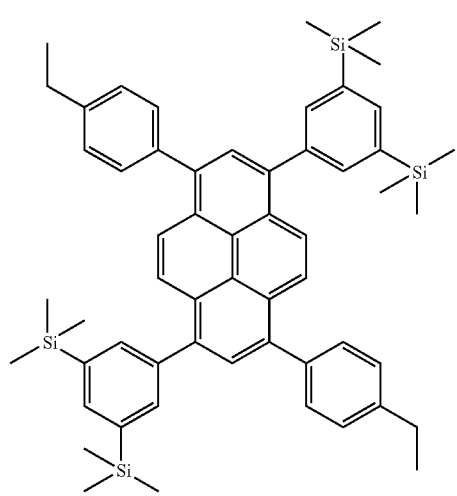
BD-93
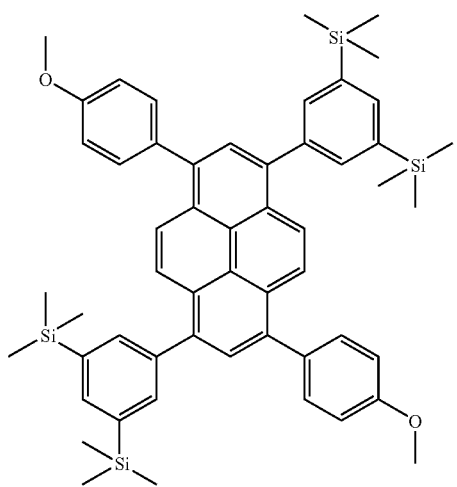
BD-94
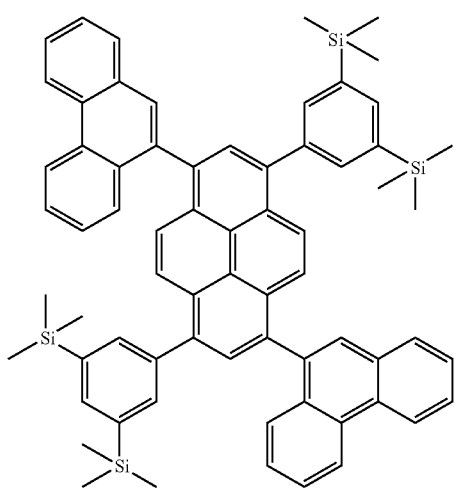
BD-94
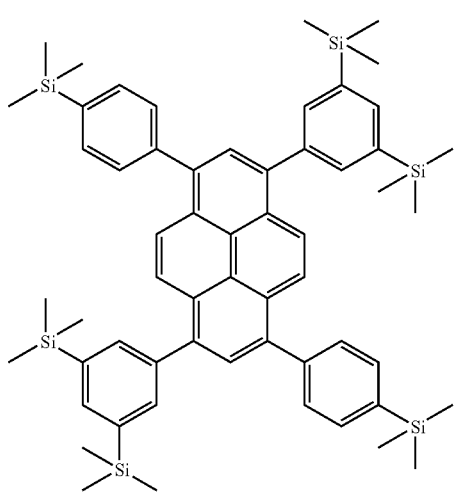

-continued
BD-95
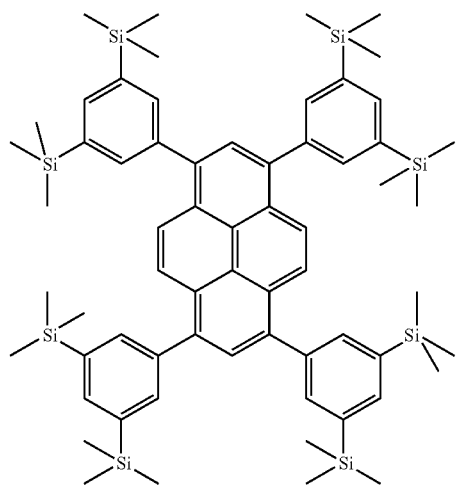
BD-96
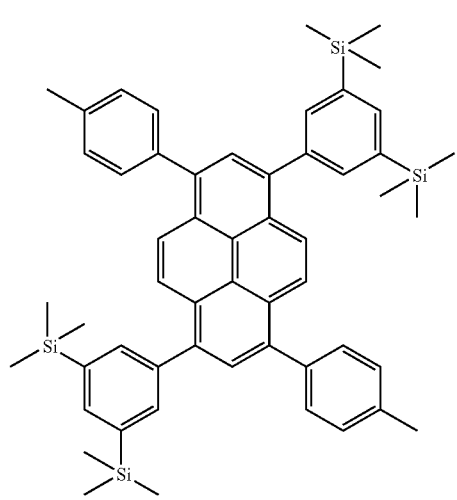
BD-97
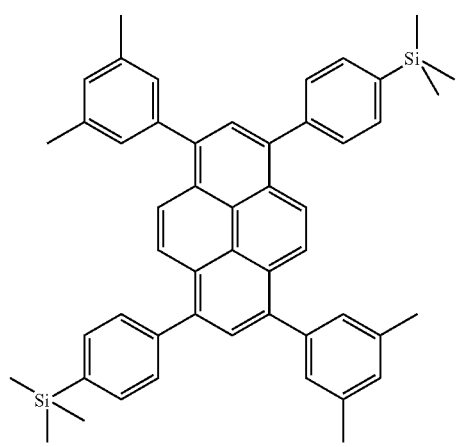
-continued
BD-98
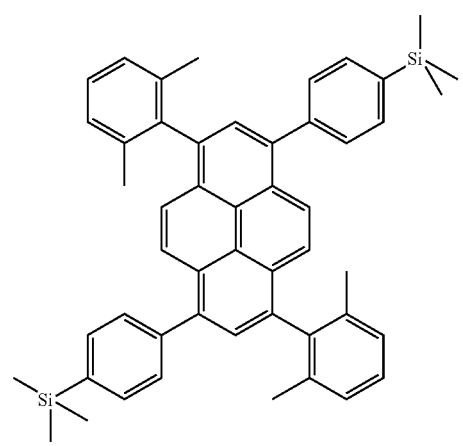
BD-99
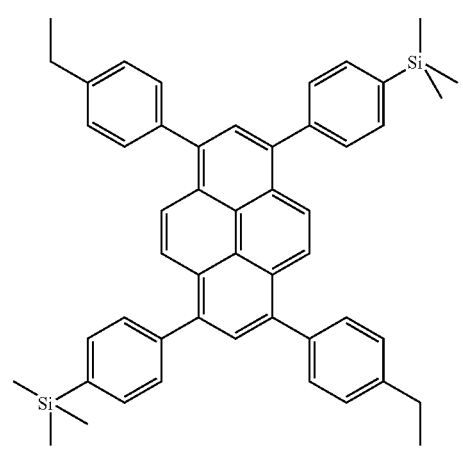
BD-100
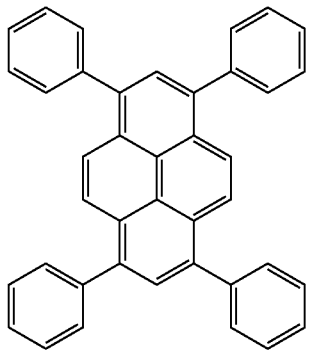

BD-101
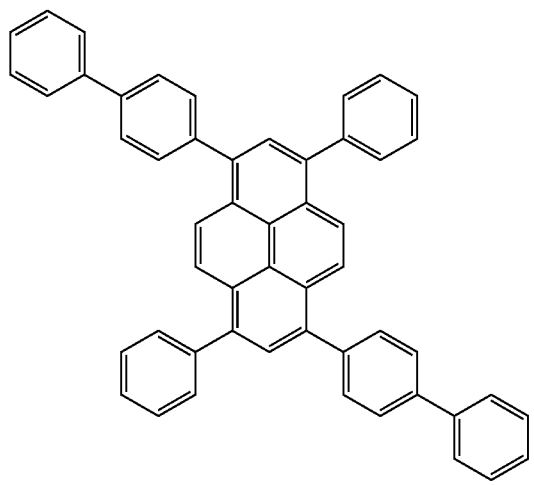
BD-104
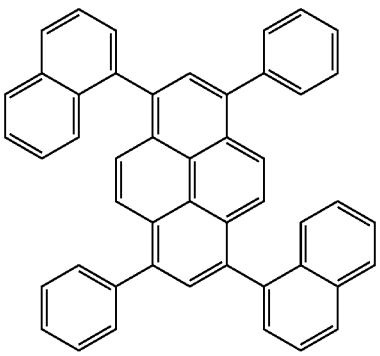
BD-102
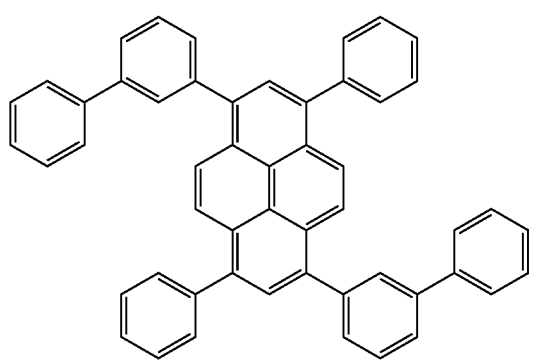
BD-105
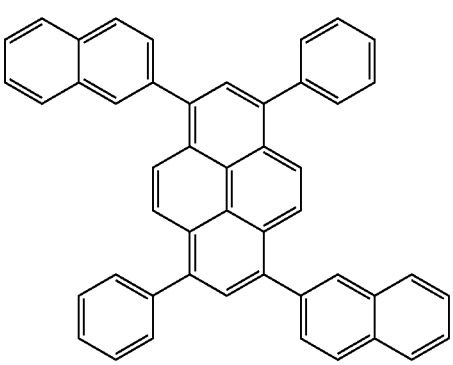
BD-103
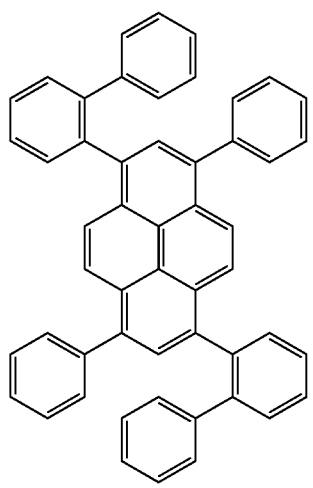
BD-106
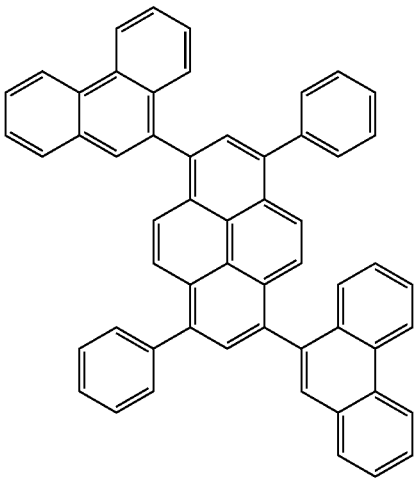

BD-107
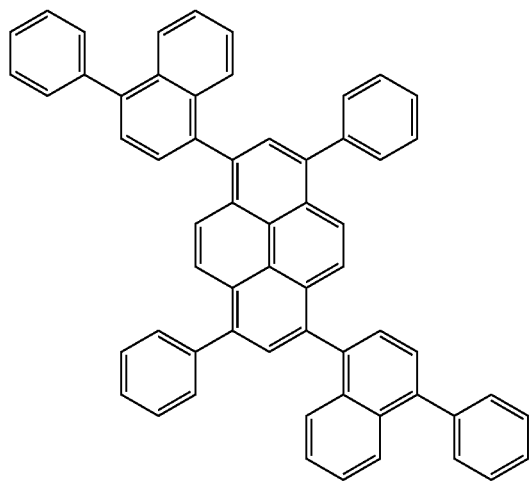
BD-110
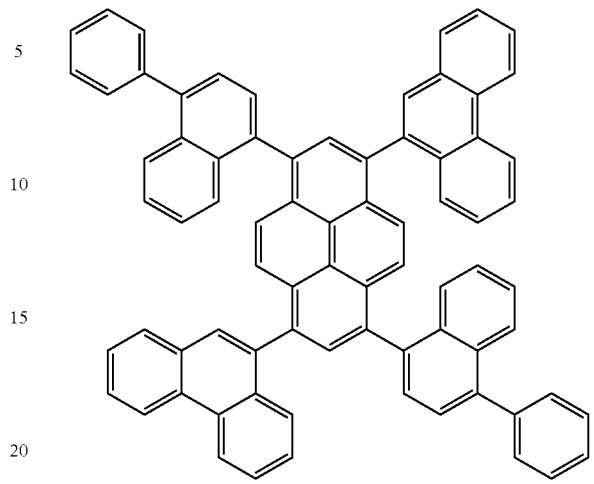
BD-108
BD-111
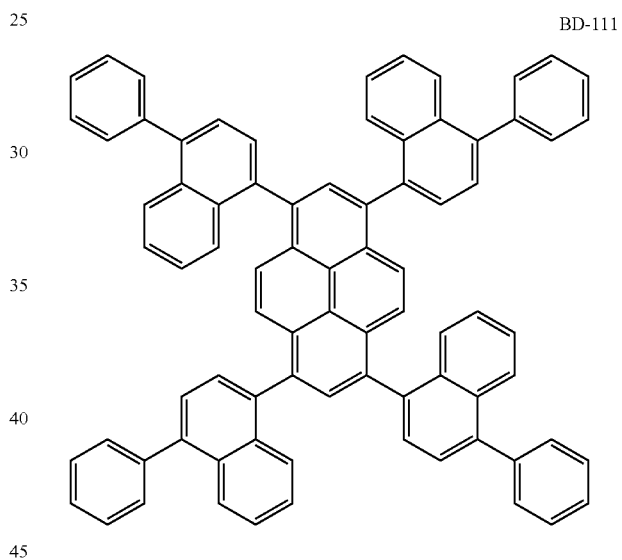
BD-109
BD-112
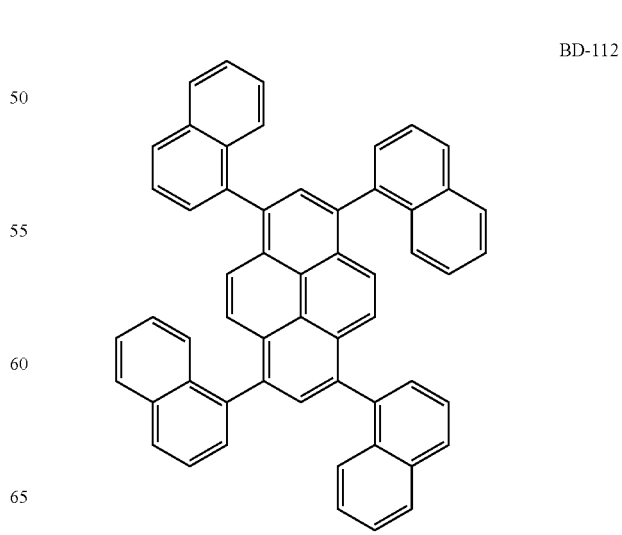

BD-113
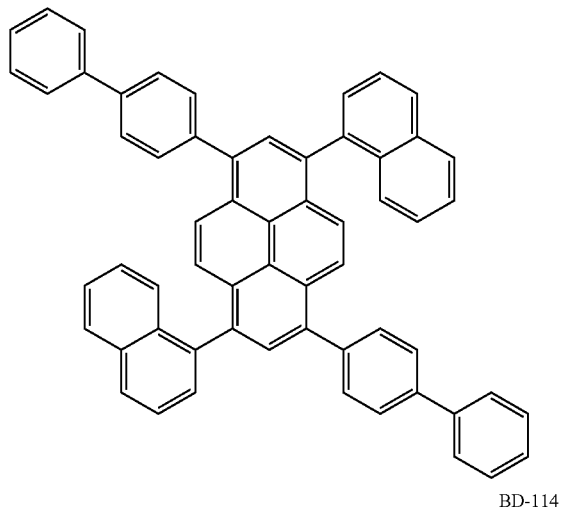
BD-114
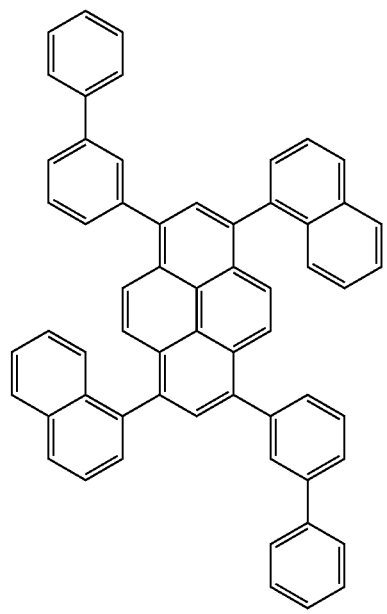
BD-115
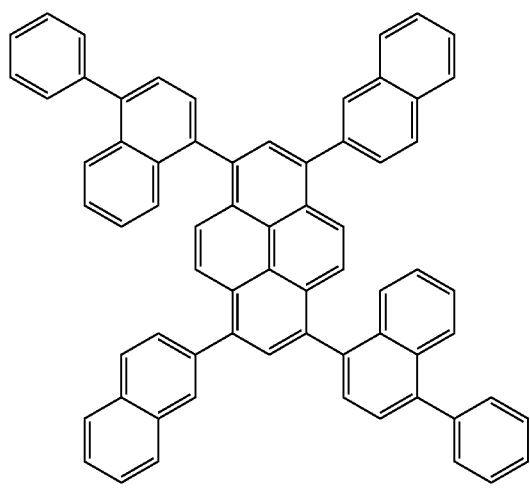
BD-116
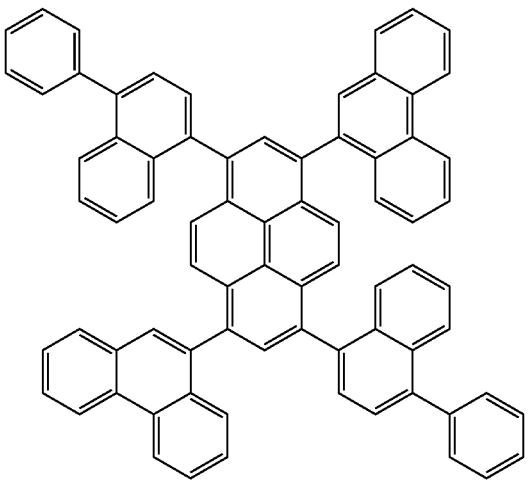
BD-117
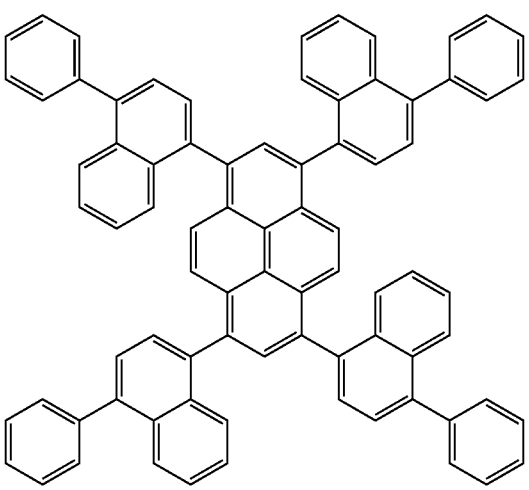
BD-118
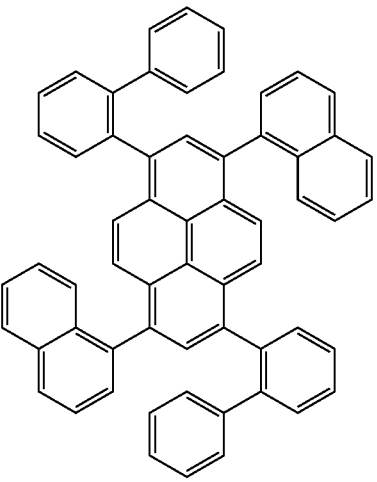

BD-119
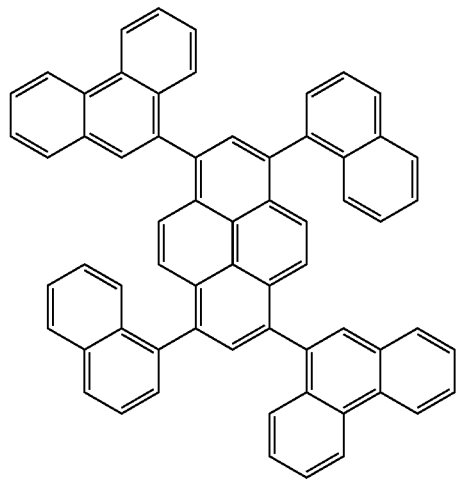
BD-120
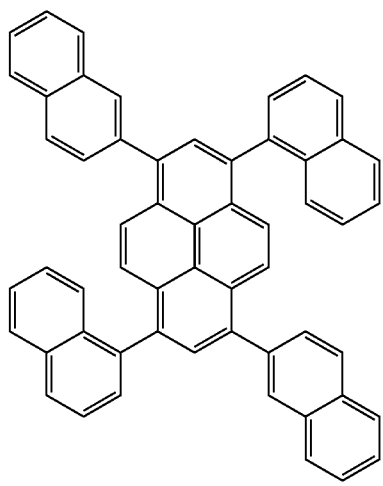
BD-121
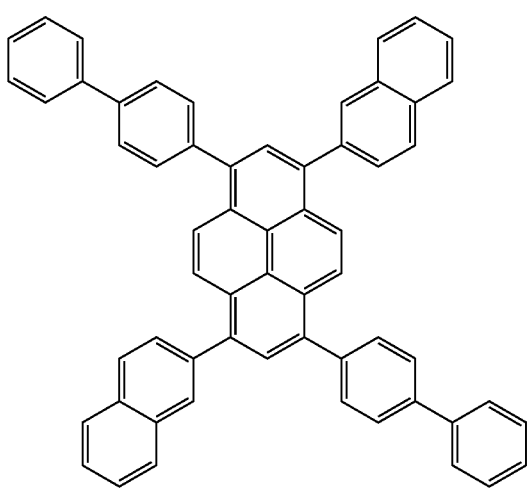
BD-122
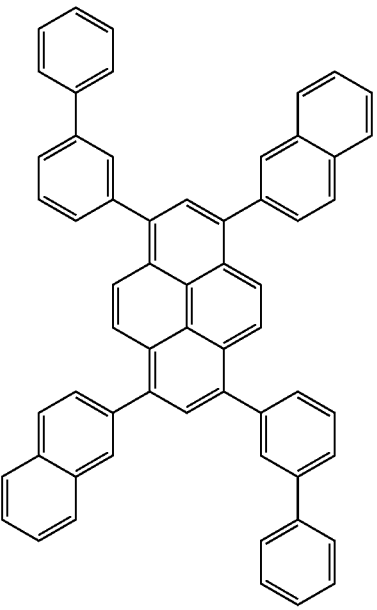
BD-123
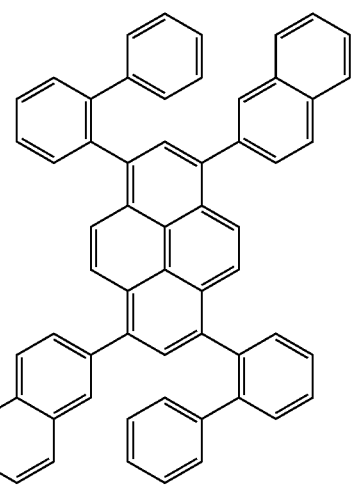
BD-124
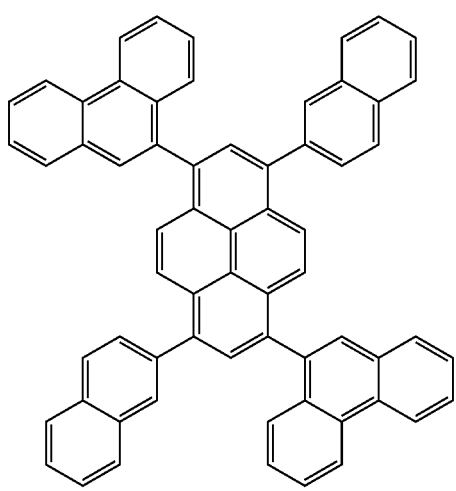

BD-125
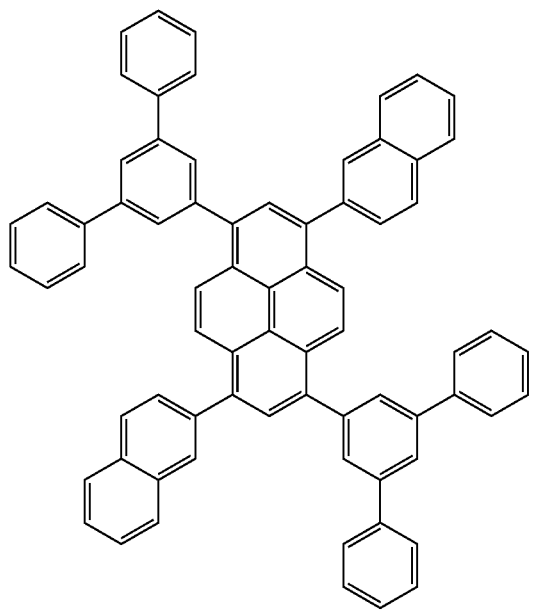
BD-128
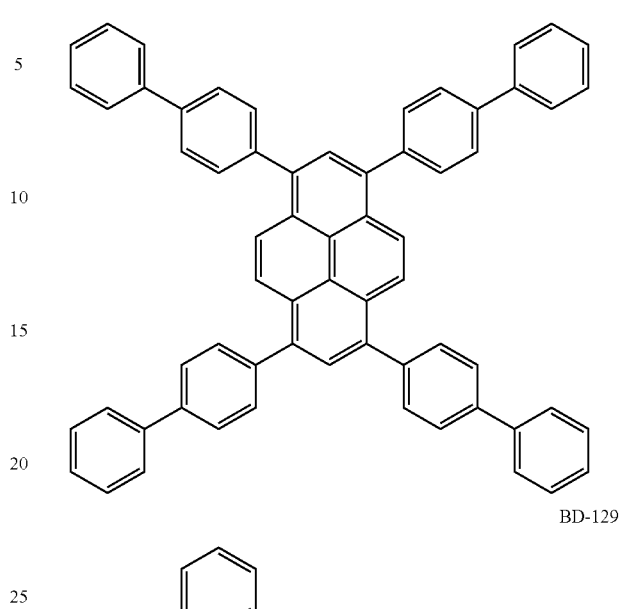
BD-126
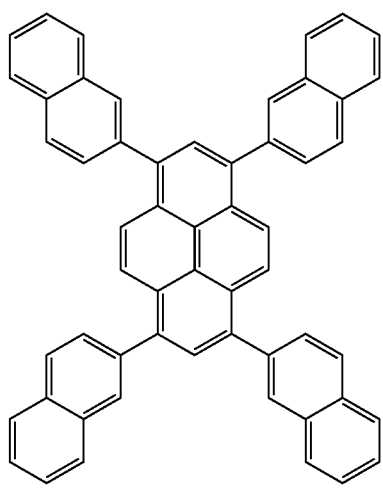
BD-129
BD-127
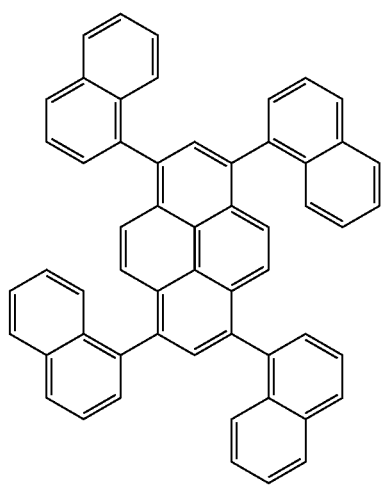
BD-130
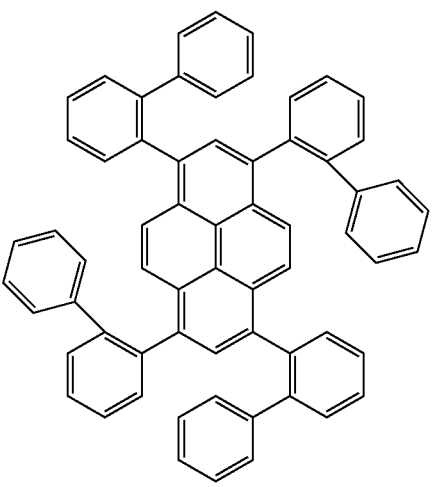

-continued
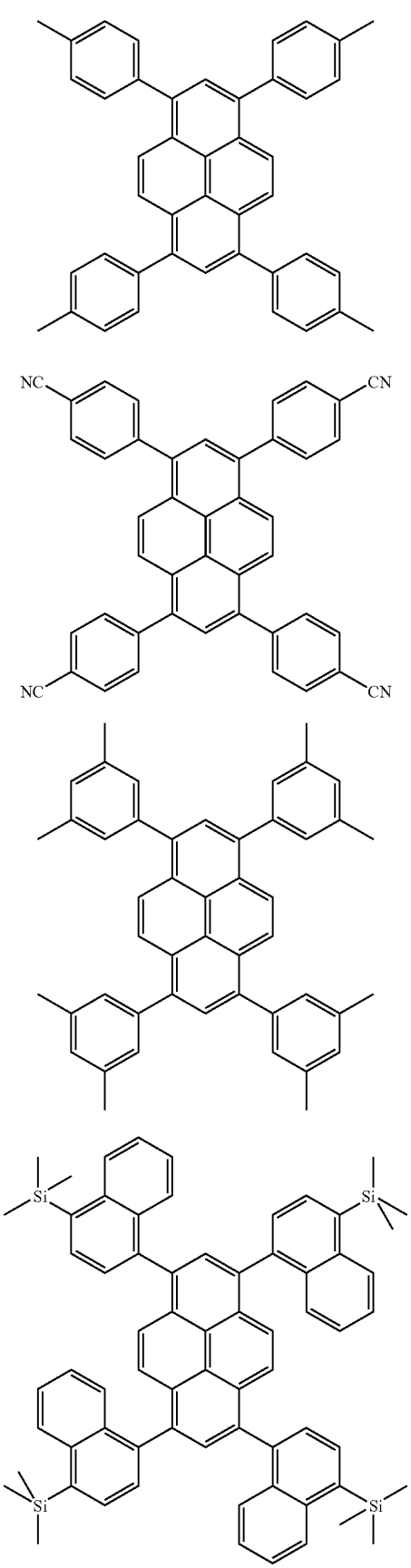
BD-131
BD-132
BD-133
BD-134
-continued
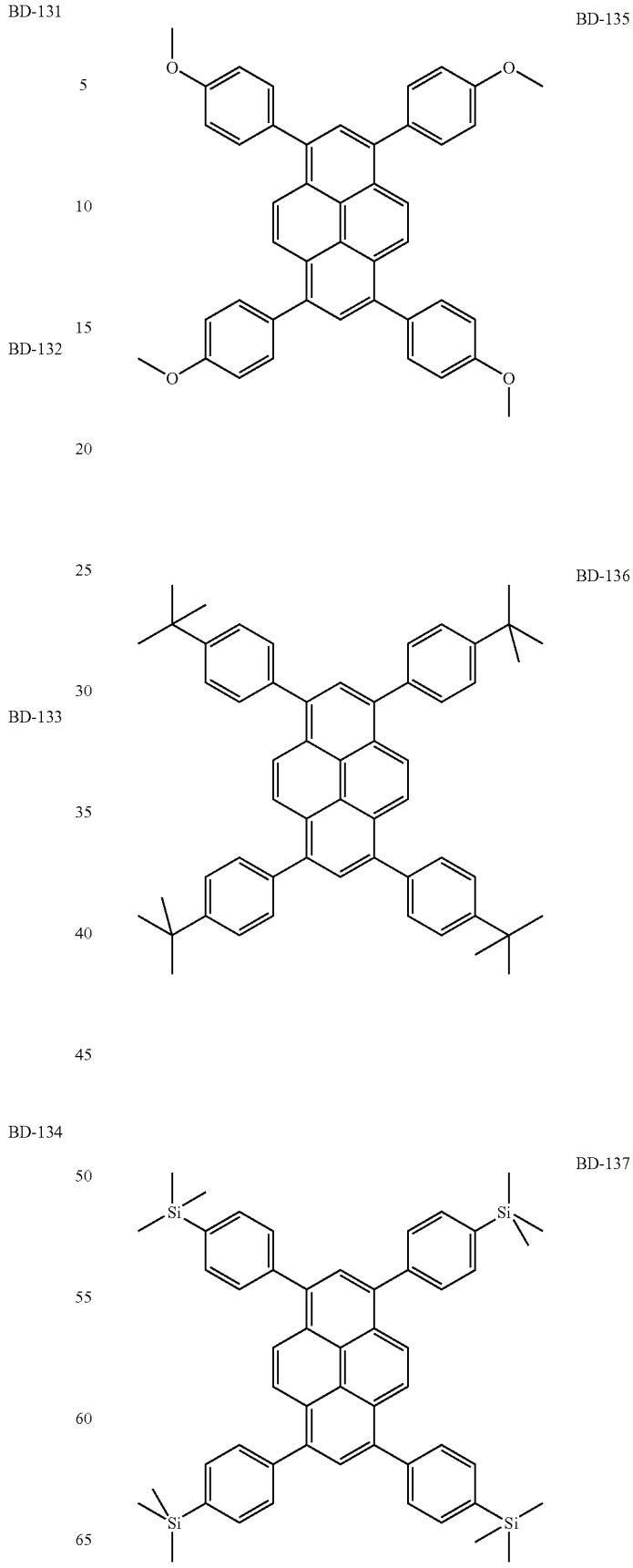
BD-135
BD-136
BD-137

BD-138
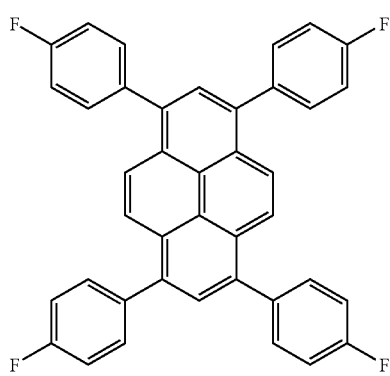
BD-141
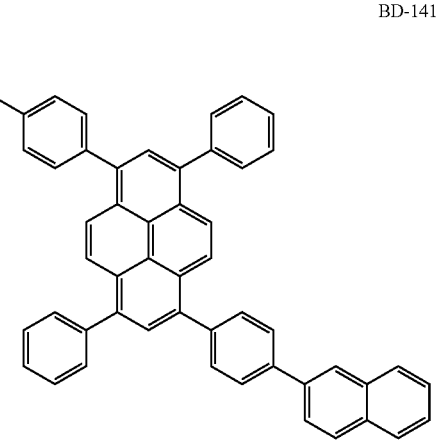
BD-139
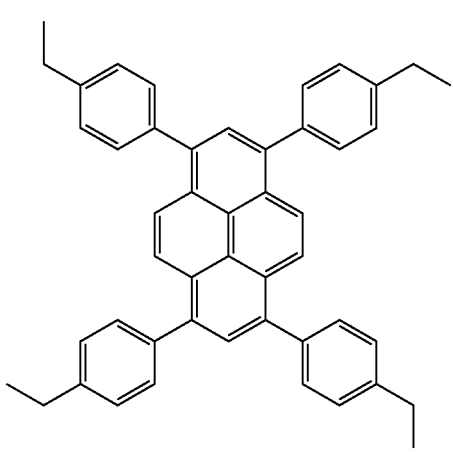
BD-140
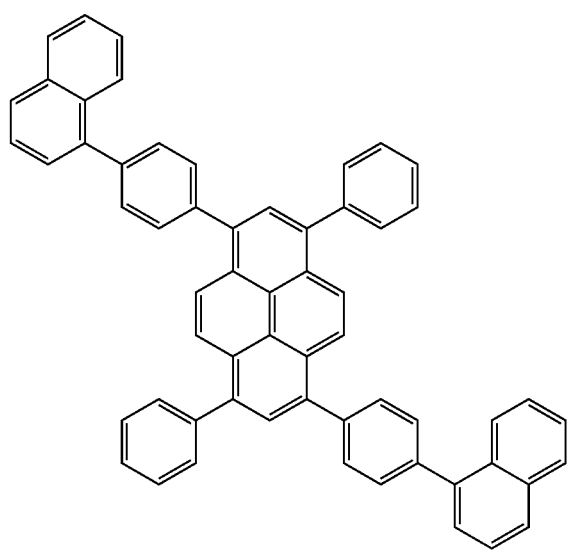
BD-142
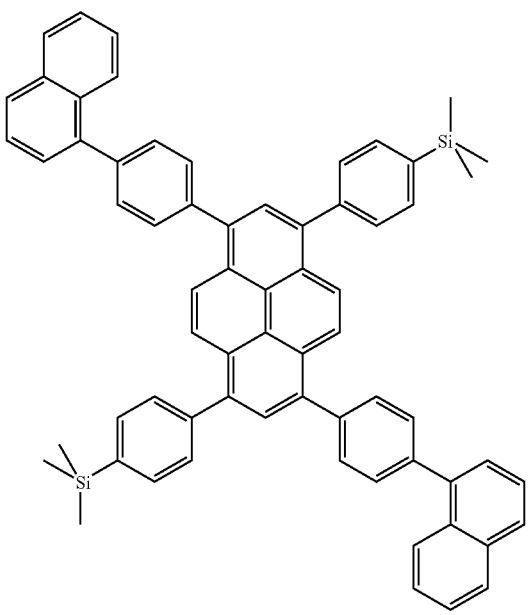

BD-143
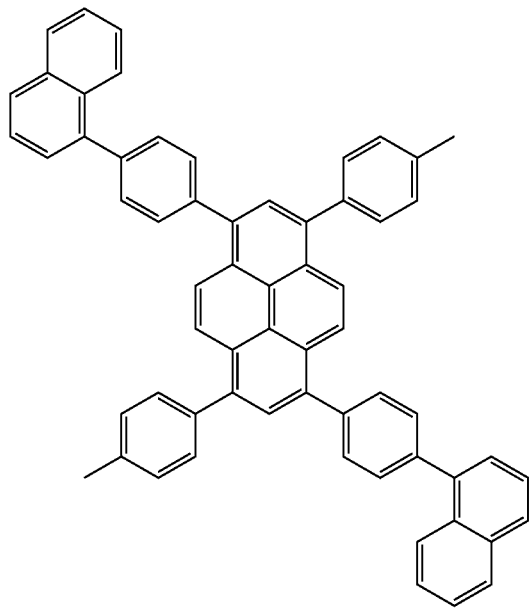
BD-145
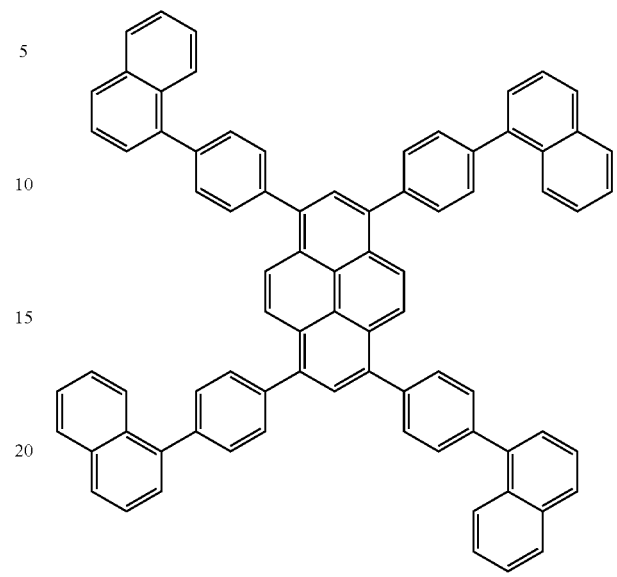
BD-144
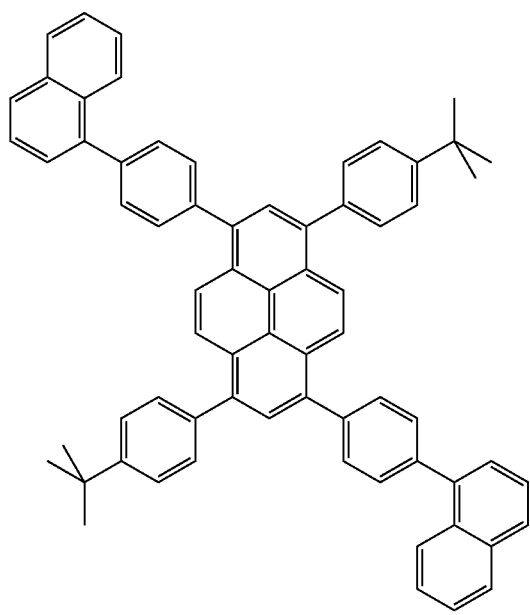
BD-146
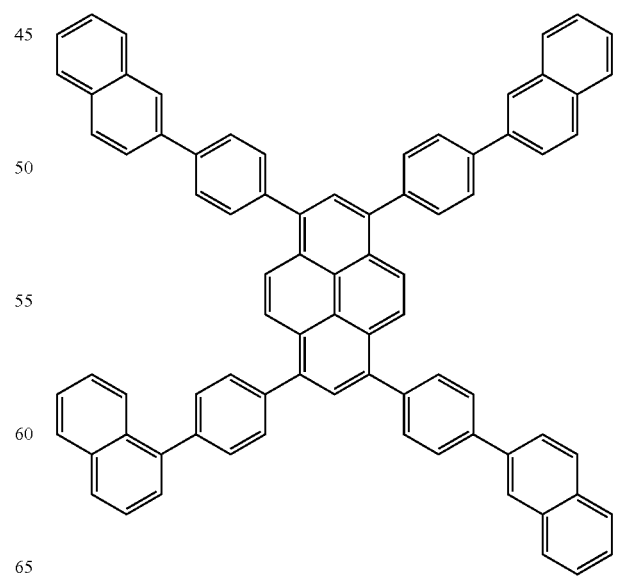

BD-147
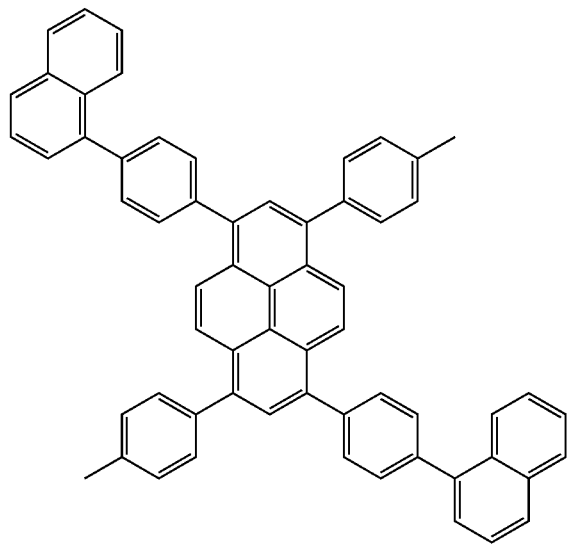
BD-149
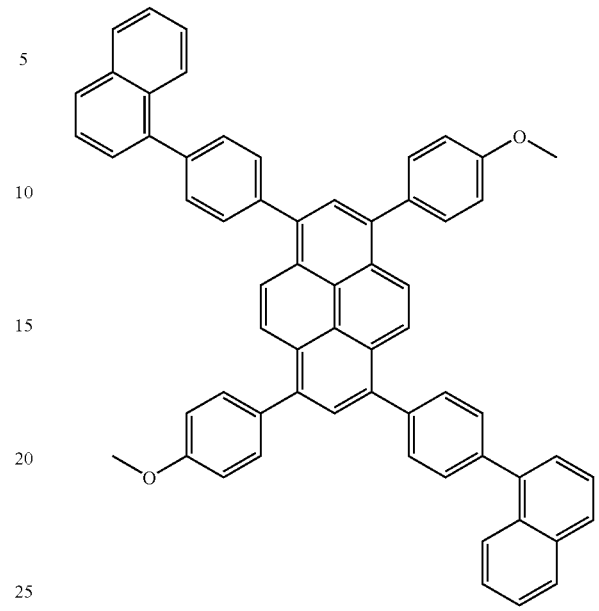
BD-148
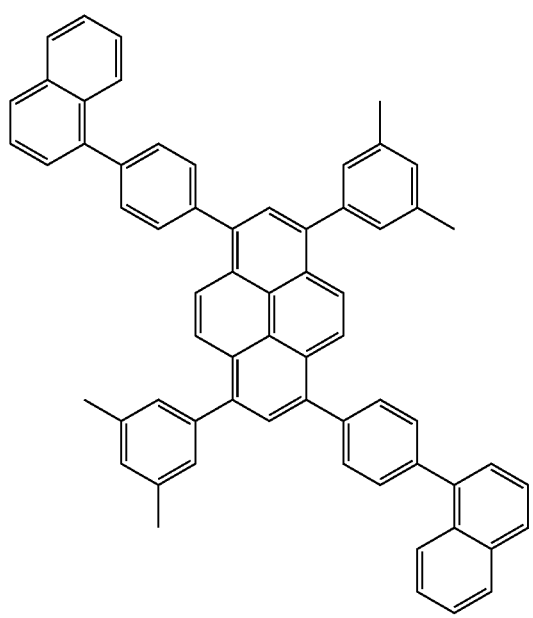
BD-150
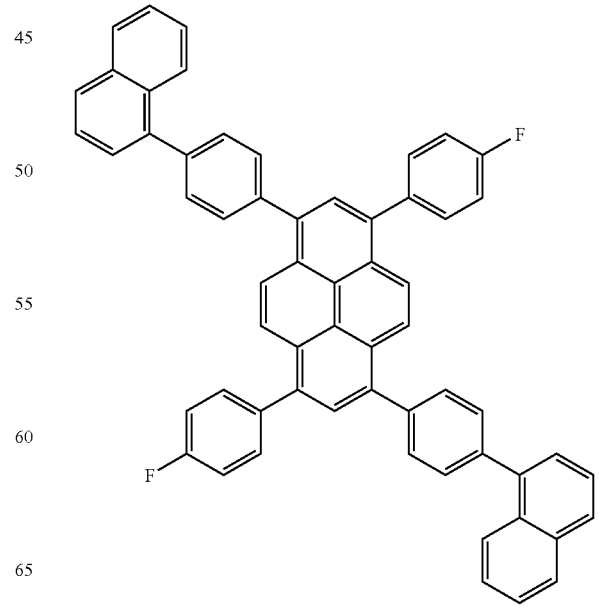

BD-151
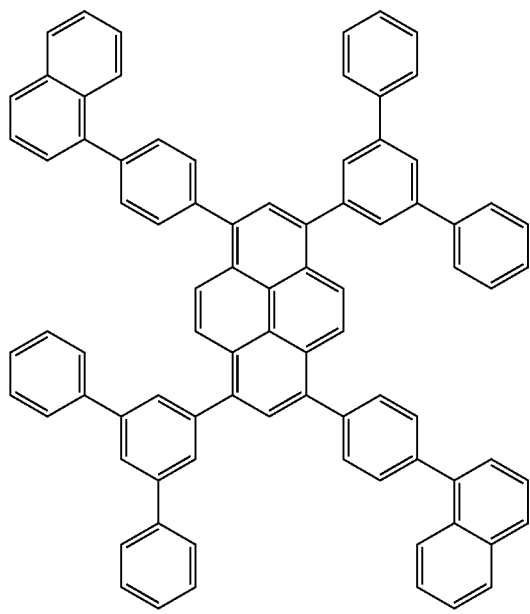
BD-153
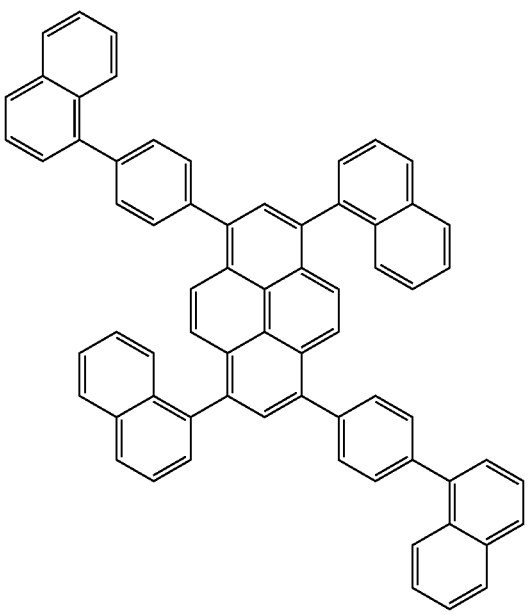
BD-152
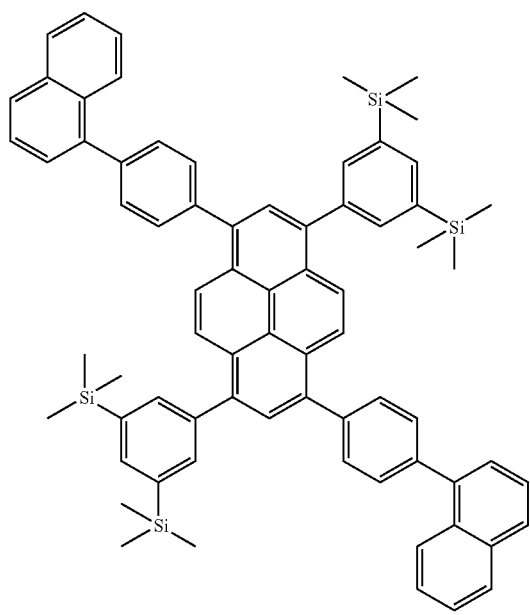
BD-154
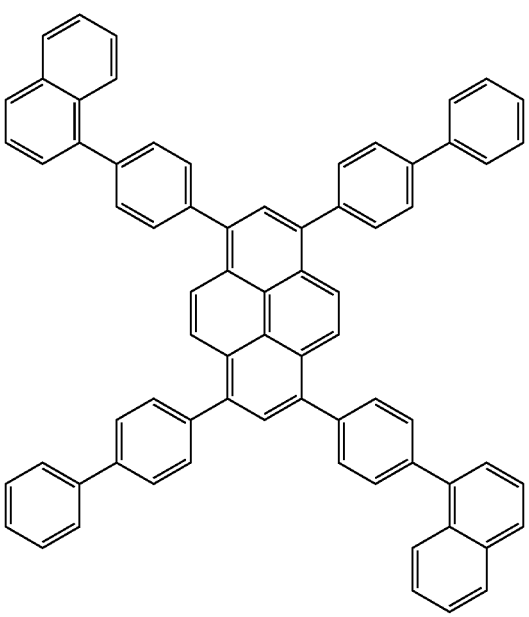

BD-155
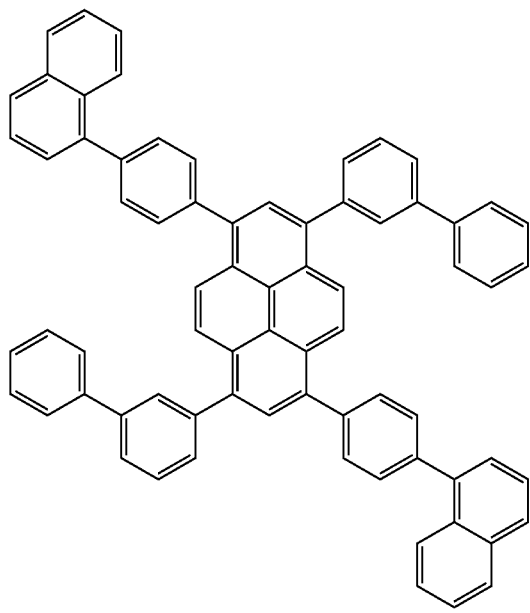
BD-157
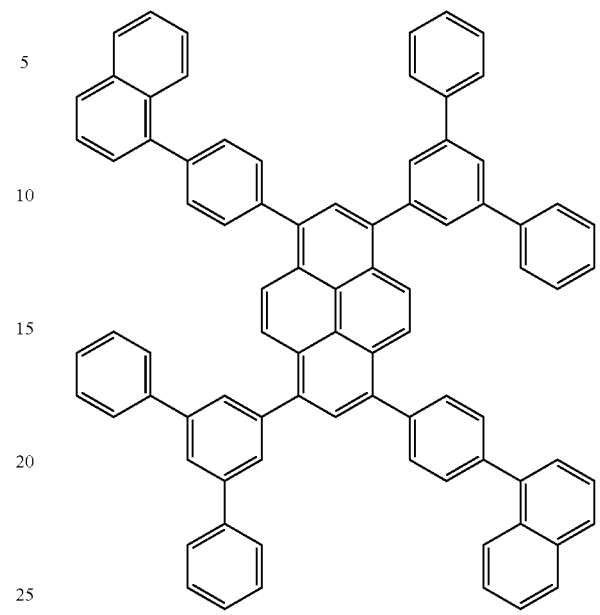
BD-156
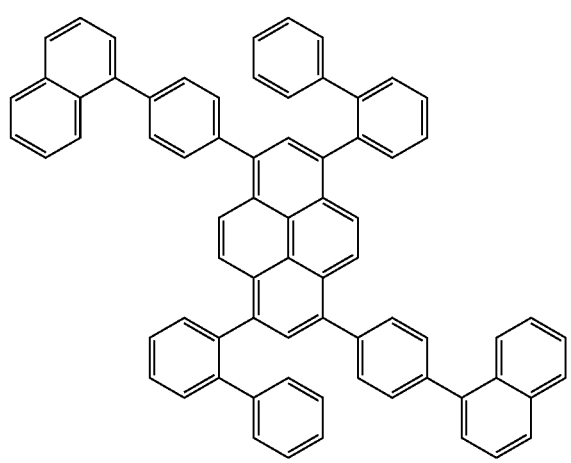
BD-158
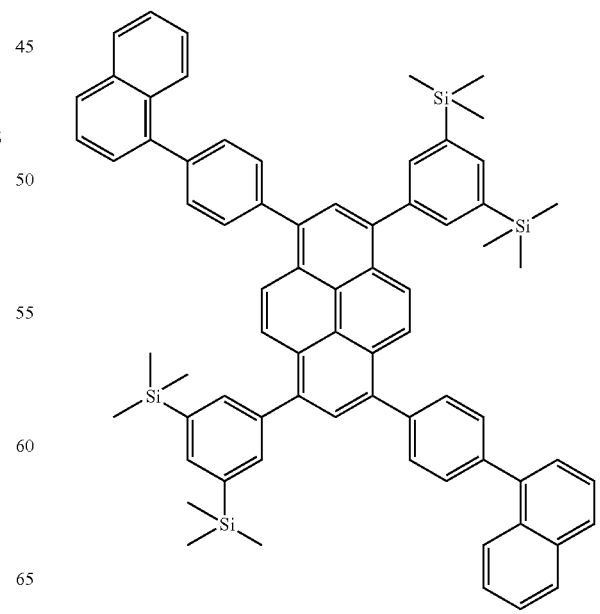

BD-159
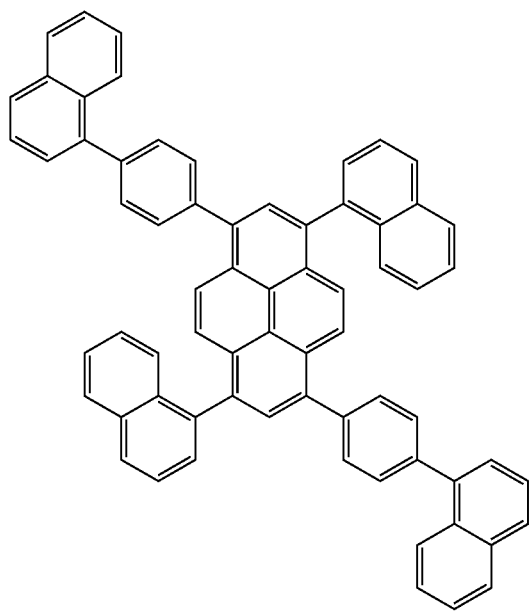
BD-161
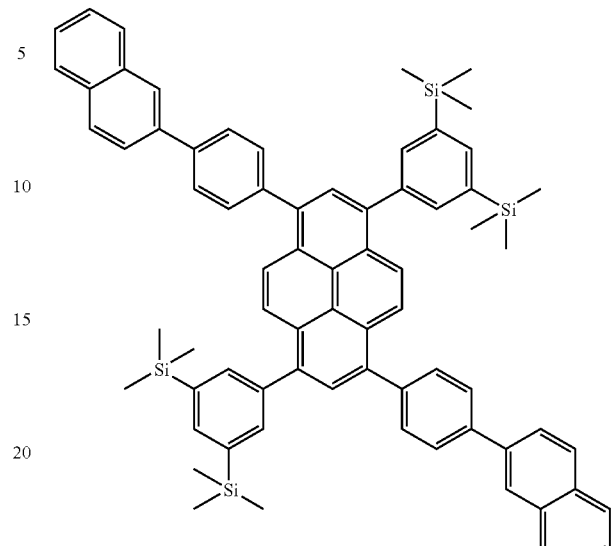
BD-160
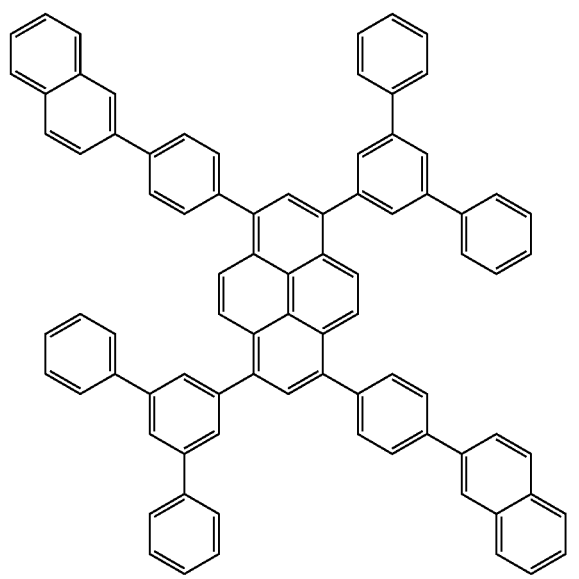
BD-162
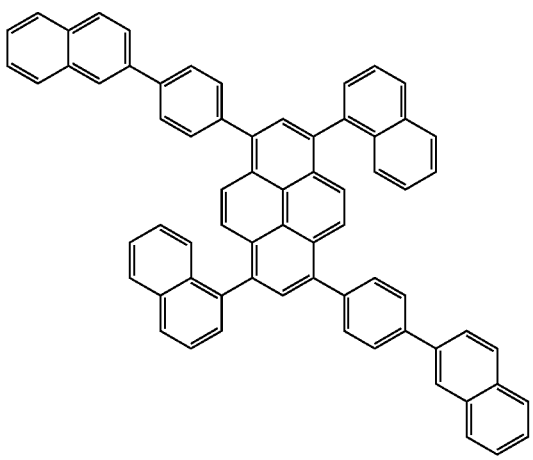

BD-163
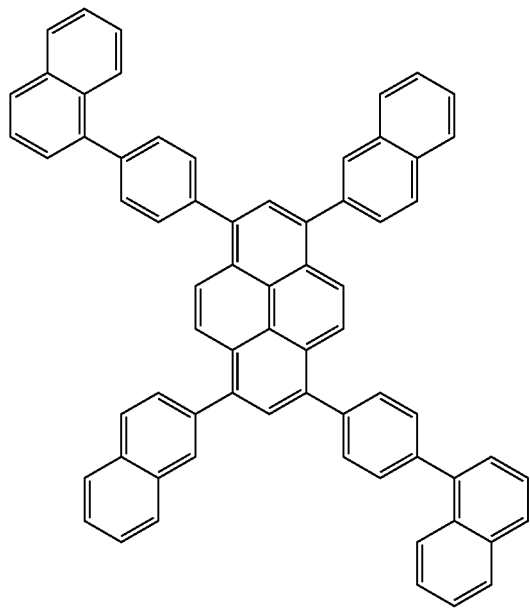
BD-164
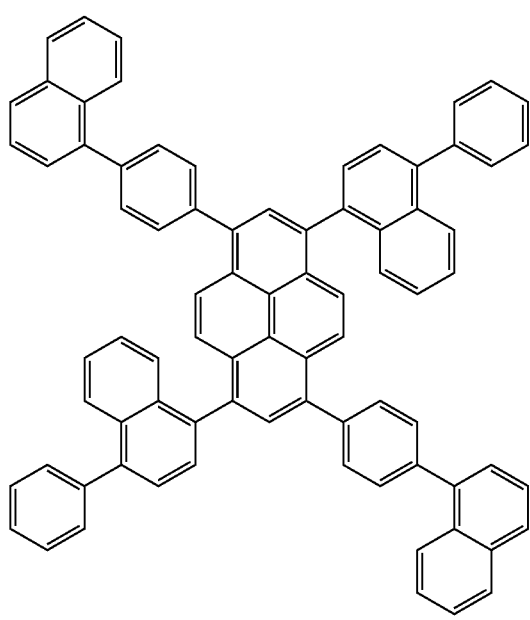
BD-165
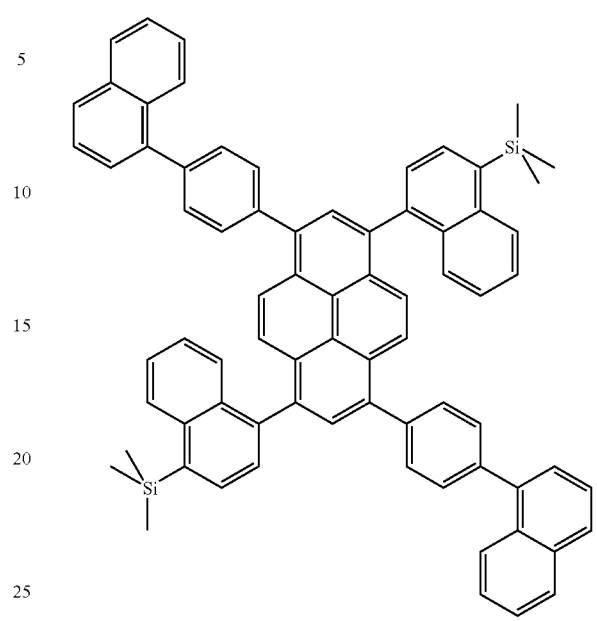
BD-166
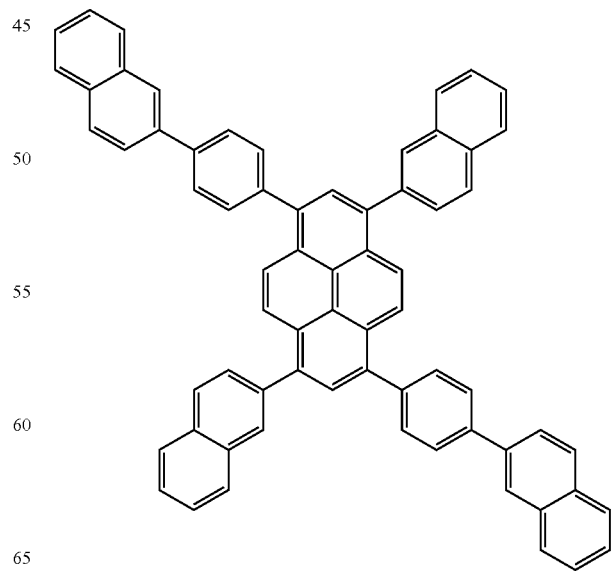

BD-167
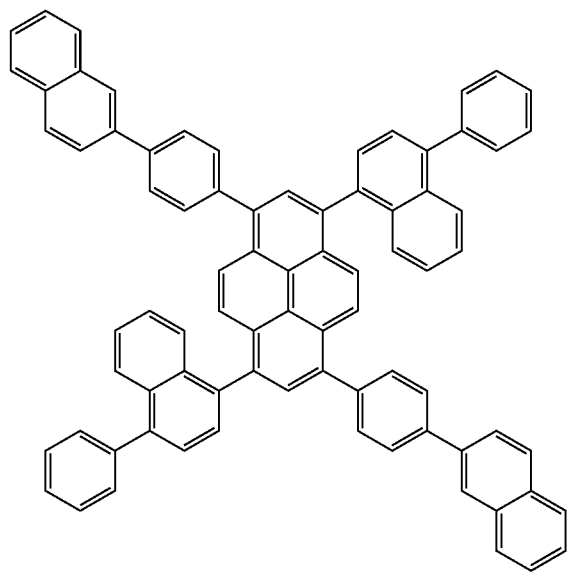
BD-169
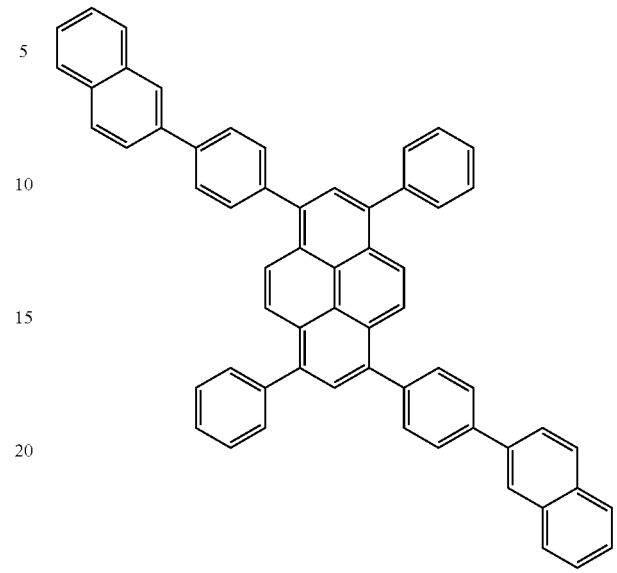
BD-168
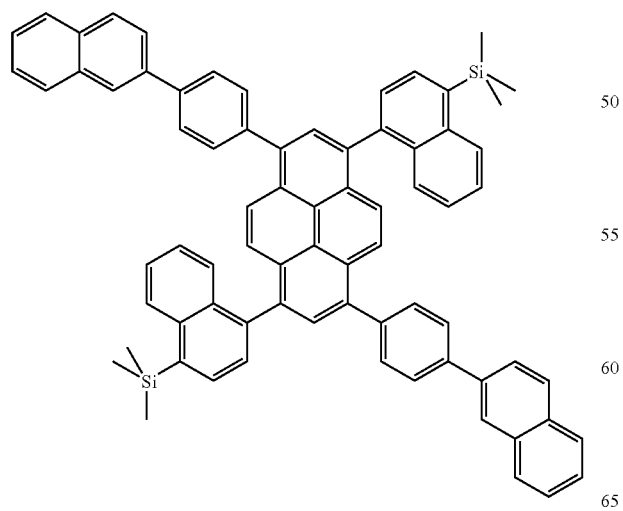
BD-170
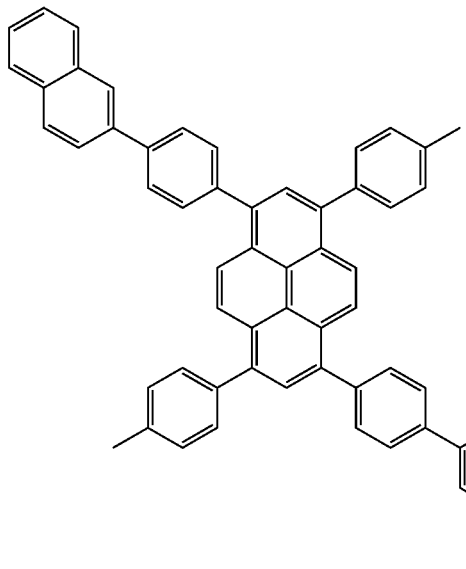

BD-171
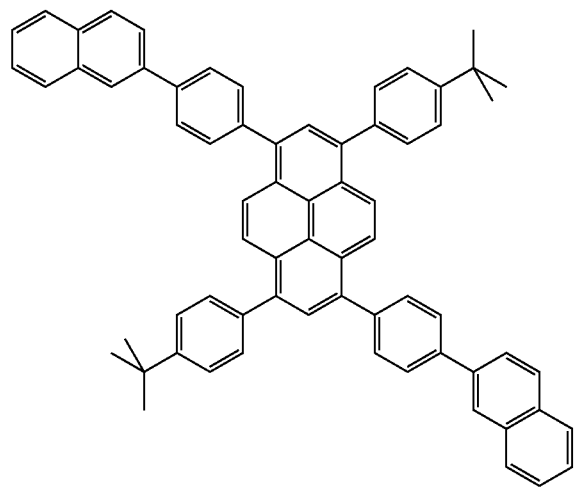
BD-173
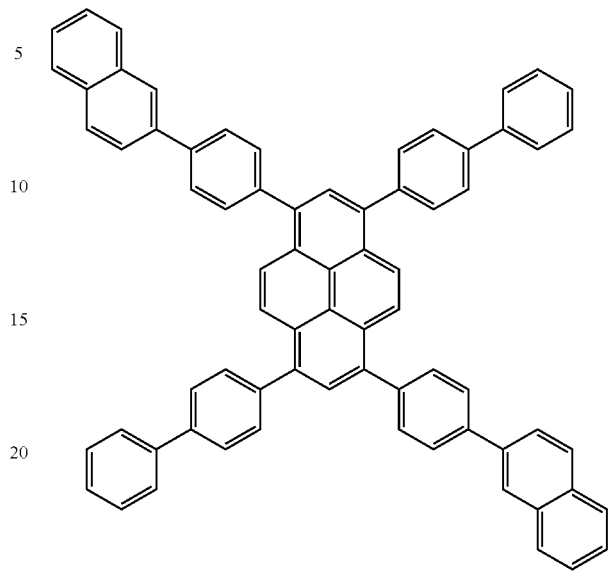
BD-172
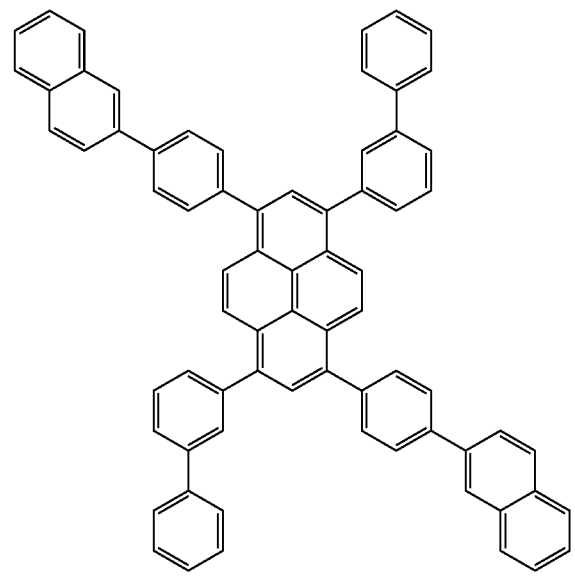
BD-174
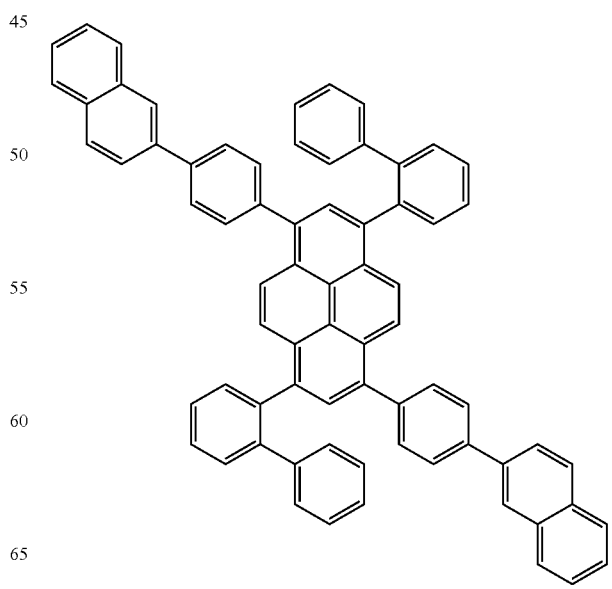

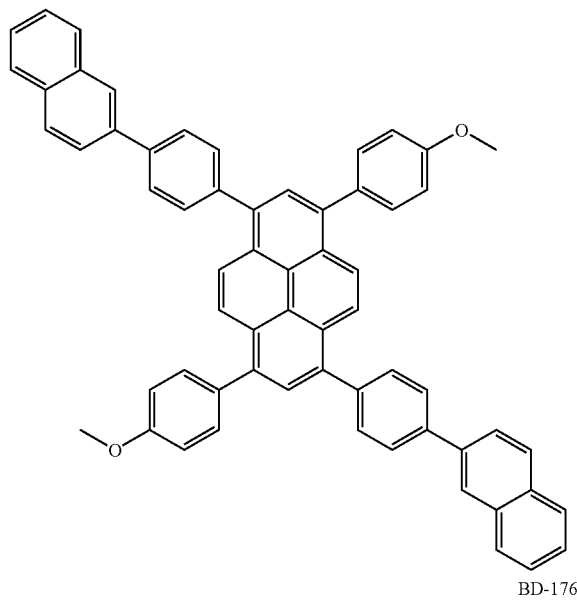
BD-175
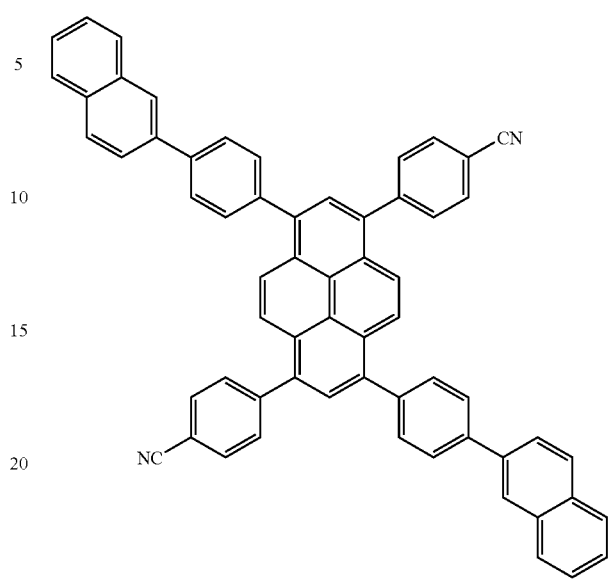
BD-178
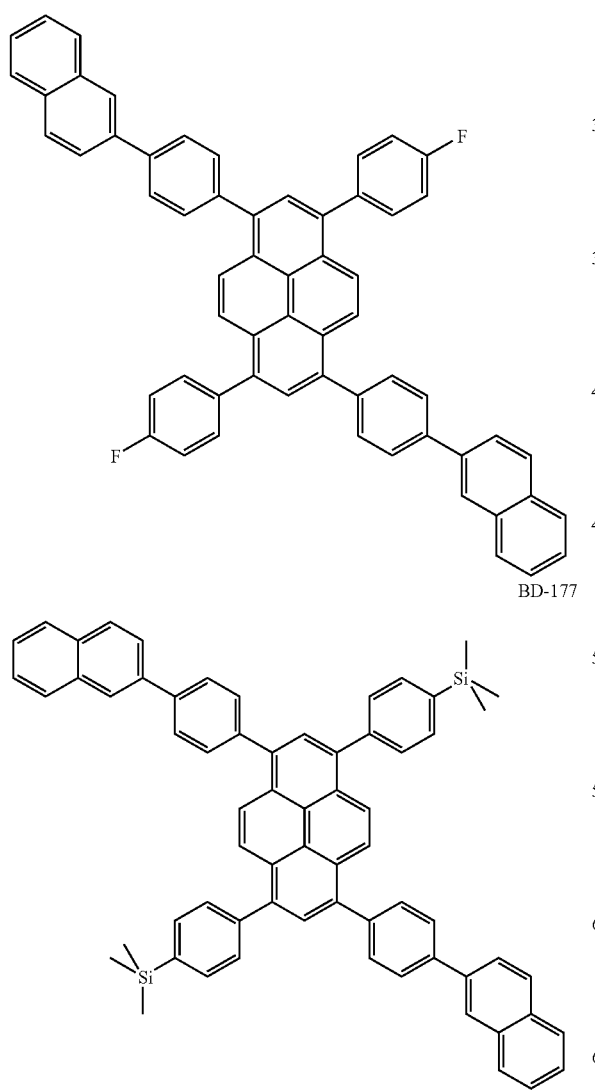
BD-176
BD-177
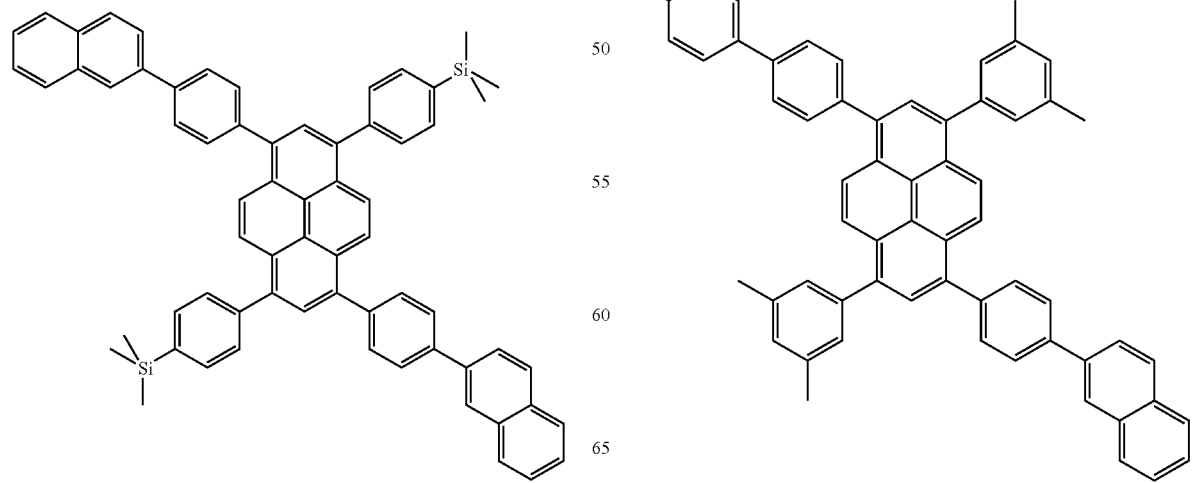
BD-179

-continued

BD-180

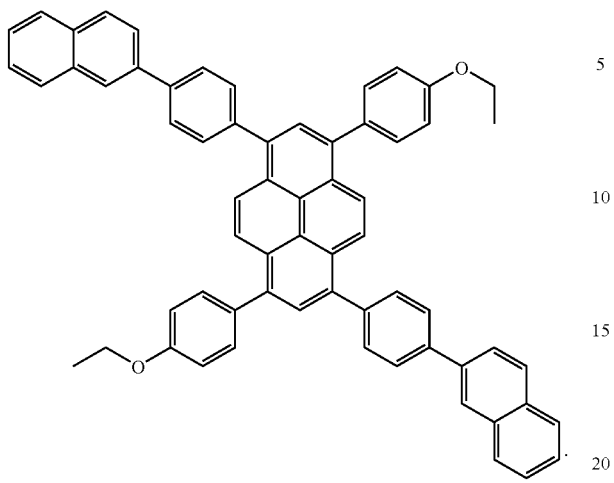

3. An organic light emitting device comprising:
an anode on a substrate;
a hole inject layer on the anode;
a hole transport layer on the hole inject layer;
an organic light emitting layer having a host material composed of 4,4'-bis(2,2-diphenylvinyl)-1,1'-iphenyl (DPVBi) and a dopant defined by the following chemical formula, 5% of the dopant being added to the host material,

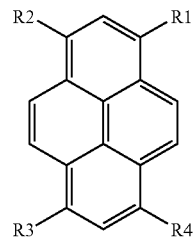

where R1=R3, R2=R4, and R1≠R2, each of R1 and R3 is phenyl substituted with at least one selected from the group consisting of trimethylsilane (TMS), CN, halogen, alkyl group with 1 to 4 carbon atoms (C1-C4) and Phenyl and each of R2 and R4 is anthracene or phenanthrene, each of which is independently substituted or un-substituted;

an electron transport layer formed on the organic light emitting layer; and a cathode formed on the electron transport layer.

* * * * *